United States Patent
Sun et al.

(10) Patent No.: US 9,801,962 B2
(45) Date of Patent: Oct. 31, 2017

(54) RADIOACTIVE NANOPARTICLES AND METHODS OF MAKING AND USING THE SAME

(71) Applicant: BOARD OF REGENTS, THE UNIVERSITY OF TEXAS SYSTEM, Austin, TX (US)

(72) Inventors: Xiankai Sun, Coppell, TX (US); Yaowu Hao, Southlake, TX (US); Sina Moeendarbari, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/719,921

(22) Filed: May 22, 2015

(65) Prior Publication Data

US 2015/0320895 A1    Nov. 12, 2015

Related U.S. Application Data

(63) Continuation-in-part of application No. 13/161,251, filed on Jun. 15, 2011, now Pat. No. 9,040,157.
(Continued)

(51) Int. Cl.
*A61K 51/12* (2006.01)
*A61N 5/10* (2006.01)
(Continued)

(52) U.S. Cl.
CPC ...... *A61K 51/1251* (2013.01); *A61K 49/0065* (2013.01); *A61K 49/0093* (2013.01);
(Continued)

(58) Field of Classification Search
None
See application file for complete search history.

(56) References Cited

U.S. PATENT DOCUMENTS

2005/0056118 A1    3/2005    Xia et al.
2008/0021212 A1    1/2008    Whiteford et al.
(Continued)

FOREIGN PATENT DOCUMENTS

WO    2008018707 A1    2/2008

OTHER PUBLICATIONS

Feng, K., Yan, J., Li, X., Xia, F., Ma, K., Wang, S., Bie, P., and Dong, J. (2012). A randomized controlled trial of radiofrequency ablation and surgical resection in the treatment of small hepatocellular carcinoma. Journal of hepatology 57, 794-802.
(Continued)

*Primary Examiner* — Jeffrey Washville
(74) *Attorney, Agent, or Firm* — John P. Zimmer; Smith Moore Leatherwood LLP

(57) ABSTRACT

In one aspect, radioactive nanoparticles are described herein. In some embodiments, a radioactive nanoparticle described herein comprises a metal nanoparticle core, an outer metal shell disposed over the metal nanoparticle core, and a metallic radioisotope disposed within the metal nanoparticle core or within the outer metal shell. In some cases, the radioactive nanoparticle has a size of about 30-500 nm in three dimensions. In addition, in some embodiments, the radioactive nanoparticle further comprises an inner metal shell disposed between the metal nanoparticle core and the outer metal shell. The metal nanoparticle core, outer metal shell, and inner metal shell of the radioactive nanoparticle can have various metallic compositions.

17 Claims, 30 Drawing Sheets

Related U.S. Application Data

(60) Provisional application No. 61/355,364, filed on Jun. 16, 2010.

(51) Int. Cl.

| | | |
|---|---|---|
| *A61K 51/02* | (2006.01) | |
| *A61K 49/00* | (2006.01) | |
| *A61K 49/18* | (2006.01) | |
| *B01J 13/02* | (2006.01) | |
| *B22F 1/00* | (2006.01) | |
| *B22F 1/02* | (2006.01) | |
| *B82Y 30/00* | (2011.01) | |
| *B01J 13/22* | (2006.01) | |
| *G21G 4/08* | (2006.01) | |
| *A61K 9/00* | (2006.01) | |
| *A61K 9/51* | (2006.01) | |
| *B82Y 20/00* | (2011.01) | |
| *B22F 9/14* | (2006.01) | |

(52) U.S. Cl.
CPC .......... *A61K 49/183* (2013.01); *A61K 51/025* (2013.01); *A61N 5/1014* (2013.01); *A61N 5/1077* (2013.01); *B01J 13/02* (2013.01); *B01J 13/22* (2013.01); *B22F 1/0018* (2013.01); *B22F 1/025* (2013.01); *B82Y 30/00* (2013.01); *G21G 4/08* (2013.01); *A61K 9/0002* (2013.01); *A61K 9/5115* (2013.01); *A61N 2005/1024* (2013.01); *A61N 2005/1089* (2013.01); *B22F 9/14* (2013.01); *B22F 2001/0029* (2013.01); *B82Y 20/00* (2013.01); *Y10T 428/2982* (2015.01); *Y10T 428/2984* (2015.01); *Y10T 428/2989* (2015.01)

(56) References Cited

U.S. PATENT DOCUMENTS

| | | | |
|---|---|---|---|
| 2008/0305489 A1 | 12/2008 | Thomas et al. | |
| 2009/0186060 A1* | 7/2009 | Hainfeld ............ | A61K 41/0038 424/422 |
| 2010/0228237 A1 | 9/2010 | Chung et al. | |
| 2011/0311822 A1 | 12/2011 | Hao et al. | |
| 2013/0004417 A1 | 1/2013 | Robertson et al. | |
| 2013/0195979 A1* | 8/2013 | Tersigni ............ | A61K 41/0052 424/490 |

OTHER PUBLICATIONS

Livraghi, T., Meloni, F., Di Stasi, M., Rolle, E., Solbiati, L., Tinelli, C., and Rossi, S. (2008). Sustained complete response and complications rates after radiofrequency ablation of very early hepatocellular carcinoma in cirrhosis: Is resection still the treatment of choice? Hepatology 47, 82-89.

Nijsen, J.F., van het Schip, A.D., Hennink, W.E., Rook, D.W., van Rijk, P.P., and de Klerk, J.M. (2002). Advances in nuclear oncology: microspheres for internal radionuclide therapy of liver tumours. Current medicinal chemistry 9, 73-82.

Popperl, G., Helmberger, T., Munzing, W., Schmid, R., Jacobs, T.F., and Tatsch, K. (2005). Selective internal radiation therapy with SIR-Spheres in patients with nonresectable liver tumors. Cancer biotherapy & radiopharmaceuticals 20, 200-208.

Connell, P.P., and Hellman, S. (2009). Advances in Radiotherapy and Implications for the Next Century: A Historical Perspective. Cancer Res 69, 383-392.

Lertsanguansinchai, P., Lertbutsayanukul, C., Shotelersuk, K., Khorprasert, C., Rojpornpradit, P., Chottetanaprasith, T., Srisuthep, A., Suriyapee, S., Jumpangern, C., Tresukosol, D., and Charoonsantikul, C. (2004). Phase III randomized trial comparing LDR and HDR brachytherapy in treatment of cervical carcinoma. International Journal of Radiation Oncology Biology Physics 59, 1424-1431.

Hsu, C.J., Huang, C.W., Hao, Y.W., and Liu, F.Q. (2012). Synthesis of highly active and stable Au-PtCu core-shell nanoparticles for oxygen reduction reaction. Phys Chem Chem Phys 14, 14696-14701.

Hsu, C.J., Huang, C.W., Hao, Y.W., and Liu, F.Q. (2012). Au/Pd core-shell nanoparticles for enhanced electrocatalytic activity and durability. Electrochemistry Communications 23, 133-136.

Hsu, C., Huang, C., Hao, Y., and Liu, F. (2013). Au/Pd Core-Shell Nanoparticles with Varied Hollow Au Cores for Enhanced Formic Acid Oxidation. Nanoscale Res Lett 8, 113.

Sangro, B., Bilbao, J.I., Boan, J., Martinez-Cuesta, A., Benito, A., Rodriguez, J., Panizo, A., Gil, B., Inarrairaegui, M., Herrero, I., Quiroga, J., and Prieto, J. (2006). Radioembolization using 90Y-resin microspheres for patients with advanced hepatocellular carcinoma. International journal of radiation oncology, biology, physics 66, 792-800.

Inarrairaegui, M., Thurston, K.G., Bilbao, J.I., D'Avola, D., Rodriguez, M., Arbizu, J., Martinez-Cuesta, A., and Sangro, B. (2010). Radioembolization with use of yttrium-90 resin microspheres in patients with hepatocellular carcinoma and portal vein thrombosis. Journal of vascular and interventional radiology : JVIR 21, 1205-1212.

Burdio, F., Navarro, A., Berjano, E.J., Burdio, J.M., Gonzalez, A., Guemes, A., Sousa, R., Rufas, M., Cruz, I., Castiella, T., Lozano, R., Lequerica, J.L., and Grande, L. (2008). Radiofrequency hepatic ablation with internally cooled electrodes and hybrid applicators with distant saline infusion using an in vivo porcine model. European journal of surgical oncology : the journal of the European Society of Surgical Oncology and the British Association of Surgical Oncology 34, 822-830.

Vente, M.A., de Wit, T.C., van den Bosch, M.A., Bult, W., Seevinck, P.R., Zonnenberg, B.A., de Jong, H.W., Krijger, G. C., Bakker, C.J., van het Schip, A.D., and Nijsen, J.F. (2010). Holmium-166 poly(L-lactic acid) microsphere radioembolisation of the liver: technical aspects studied in a large animal model. European radiology 20, 862-869.

Yue, G.H., Yan, P.X., Fan, X.Y., Wang, M.X., Qu, D.M., Yan, D., and Liu, J.Z. (2006). Characterization of the single crystalline iron sulfide nanowire array synthesis by pulsed electrodeposition. J Appl Phys 100.

European Patent Office. PCT International Search Report and Written Opinion dated Nov. 2, 2016. International Application No. PCT/US2016/033432. International Filing Date: May 20, 2016. Name of Applicant: Board of Regents, The University of Texas System. English Language. 13 pages.

Zhou, You-Fu et al. "Preparation and Evaluation of a Radioisotope-Incorporated Iron Oxide Core/Au Shell Nanoplatform for Dual Modality Imaging." Journal of Biomedical Nonotechnology. vol. 4, pp. 474-481. 2008. English Language.

Axiak-Bechtel, Sandra M. et al. "Gum arabic-coated radioactive gold nanoparticles cause no short-term local or systemic toxicity in the clinically relevant canine model of prostate cancer." International Journal of Nanomedicine. vol. 2014.9. pp. 5001-5011. English Language.

Moeendarbari, Sina et al. "Theranostic Nanoseeds for Efficacious Internal Radiation Therapy of Unresectable Solid Tumors." Scientific Reports. 6:20614/DOI: 10.1038/srep20614. pp. 1-9. English Language. Feb. 8, 2016.

Tyrrell, James W.G. et al., "Images of Nanobubbles on Hydrophobie Surfaces and Their Interactions," copyright 2001, The American Physical Society, Physical Review Letters, vol. 87, No. 17, pp. 176104-1-176104-4.

Agrawal, Abhinandan et al., "Controlling the Location and Spatial Extent of Nanobubbles Using Hydrophobically Nanopatterned Surfaces," copyright 2005, American Chemical Society, NANO Letters 2005, vol. 5, No. 9, pp. 1751-1756.

Averitt, R.D. et al., "Plasmon Resonance Shifts of Au-Coated Au2S Nanoshells: Insight Into Multicomponent Nanoparticle Growth," copyright 1997, The American Physical Society, Physical Review Letters, vol. 78, No. 22, Jun. 2, 1997, pp. 4217-4220.

(56) References Cited

OTHER PUBLICATIONS

Averitt, Richard D. et al., "Linear Optical Properties of Gold Nanoshells," copyright 1999, Optical Society of America, J. Opt. Soc. Am. B., vol. 16, No. 10, Oct. 1999, pp. 1824-1832.
Banholzer, Matthew J. et al., "Electrochemical Approach to and the Physical Consequences of Preparing Nanostructures from Gold Nanorods With Smooth Ends," copyright 2008, American Chemical Society, J. Phys. Chem., vol. 112, pp. 15729-15734.
Boisselier, Elodie et al., "Gold Nanoparticles in Nanomedicine: Preparations, Imaging, Diagnostics, Therapies and Toxicity," copyright 2009, The Royal Society fo Chemistry, Chem. Soc. Rev., vol. 38, pp. 1759-1782.
Borkent, Bram M. et al., "Superstability of Surface Nanobubbles," copyright 2007, The American Physical Society, PRL, vol. 98, pp. 204502-1-204502-4.
Brenner, Michael P. et al., "Dynamic Equilibrium Mechanism for Surface Nanobubble Stabilization," copyright 2008, The American Physical Society, PRL, vol. 101, pp. 214505-1-214505-4.
Cao, Huaqiang et al., "Generation and Growth Mechanism of Metal (Fe, Co, Ni) Nanotube Arrays," copyright 2006, Wiley-VCH Verlag GmbH & Co. KgaA, Winheim, ChemPhysChem, vol. 7, pp. 1500-1504.
Chen, Jingyi et al., "Gold Nanocages: Bioconjugation and Their Potential Use as Optical Imaging Contrast Agents," copyright 2005, American Chemical Society, Nano Letters 2005, vol. 5, No. 3, pp. 473-477.
Chiang, 1-Chen et al., "Synthesis of Monodisperse FeAu Nanoparticles with Tunable Magnetic and Optical Properties," copyright 2007, Wiley-VCH Verlag GmbH & Co. KgaA, Weinheim, Advanced Functional Materials, vol. 17, pp. 1311-1316.
Choi, Jin-sil et al., "A Hybrid Nanoparticle Probe for Dual-Modality Positron Emission Tomography and Magnetic Resonance Imaging," copyright 2008, Wiley-VCH Verlag GmbH & Co. KgaA, Weinheim, Angew. Chem. Int. Ed., vol. 47, pp. 6259-6262.
Cole, Joseph R. et al., "Photothermal Efficiencies of Nanoshells and Nanorods for Clinical Therapeutic Applications," copyright 2009, American Chemical Society, J. Phys. Chem., vol. 113, pp. 12090-12094.
Cuenca, Alex G. et al., "Emerging Implications of Nanotechnology on Cancer Diagnostics and Therapeutics," copyright 2006, American Cancer Society, Wiley InterScience; pp. 459-466.
Daniel, Marie-Christine et al., "Gold Nanoparticles: Assembly, Supramolecular Chemistry, Quantum-Size-Related Properties, and Applications Toward Biology, Catalysis, and Nanotechnology," copyright 2004, American Chemical Society, Chem. Rev., vol. 104, pp. 293-346.
Davis, Mark E. et al., "Nanoparticle Therapeutics: An Emerging Treatment Modality for Cancer," copyright 2008 Macmillan Publishers Limited, Nature Reviews, vol. 7, pp. 771-782.
Devoisselle, Jean-Marie et al., "Magnetic Nanoparticles and Their Applications in Medicine," copyright 2006, Nanomedicine, 1.2, pp. 1-17.
Ferrari, Mauro, "Cancer Nanotechnology: Opportunities and Challenges," copyright 2005, Nature Publishing Group, Nature Reviews, vol. 5, pp. 161-171.
Fu, Kun et al., "Measurement of Immunotargeted Plasmonic Nanoparticles' Cellular Binding: A Key Factor in Optimizing Diagnostic Efficacy," copyright 2008, IOP Publishing Ltd., Nanotechnology, vol. 19, pp. 1-6.
Gabe, D.R., "The Role of Hydrogen in Metal Electrodeposition Processes," copyright 1997, Chapman & Hall, Journal of Applied Electrochemistry, vol. 27, pp. 908-915.
Gobin, Andre M. et al., "Near-Infrared Resonant Nanoshells for Combined Optical Imaging and Photothermal Cancer Therapy," copyright 2007, American Chemical Society, Nano Letters 2007, vol. 7, No. 7, pp. 1929-1934.
Groman, Ernest V. et al., "Ultrasmall Mixed Ferrite Colloids as Multidimensional Magnetic Resonance Imaging, Cell Labeling, and Cell Sorting Agents," copyright 2007, American Chemical Society, Bioconjugate Chem., vol. 18, pp. 1763-1771.
Grzelczak, Marek et al., "Shape Control in Gold Nanoparticle Synthesis," copyright 2008, The Royal Socity of Chemistry, Chem. Soc. Rev., vol. 37, pp. 1783-1791.
Hirsch, L.R. et al., "Nanoshell-Mediated Near-Infrared Thermal Therapy of Tumors Under Magnetic Resonance Guidance," copyright 2003, The National Academy of Sciences of the USA, PNAS, vol. 100, No. 23, pp. 13549-13554.
Issa, Nader A. et al., "Optical Nanofocusing on Tapered Metallic Waveguides," copyright 2006, Springer Science, Plasmonics, vol. 2, pp. 31-37.
Jain, Prashant K. et al, Erratum re: Fig. 6, copyright 2007, Nanotoday, Apr. 2007, vol. 2, No. 2, p. 16.
Jana, Nikhil R. et al., "Wet Chemical Synthesis of High Aspect Ratio Cylindrical Gold Nanorods," copyright 2001, American Chemical Society, J. Phys. Chem. B, vol. 105, pp. 4065-4067.
Johnson, P.B. et al., "Optical Constants of the Noble Metals," copyright 1972, Physical Review, vol. 6, No. 12., pp. 4370-4379.
Keren, S. et al., "Noninvasive Molecular Imaging of Small Living Subjects Using Raman Spectroscopy," copyright 2008, The National Academy of Science, PNAS, vol. 105, No. 15, pp. 5844-5849.
Lal, Surbhi et al., "Nanoshell-Enabled Photothermal Cancer Therapy: Impending Clinical Impact," copyright 2008, Accounts of Chemical Research, vol. 41, No. 12, pp. 1842-1851.
Lal, Surbhi et al., "Tailoring Plasmonic Substrates for Surface Enhanced Spectroscopies," copyright 2008, Chem. Soc. Rev., vol. 37, pp. 898-911.
Lee, Ha-Young et al., "PET/MRI Dual-Modality Tumor Imaging Using Arginine-Glycerine-Aspartic (RGD)—Conjugated Radiolabeled Iron Oxide Nanoparticles," copyright 2008, Society of Nuclear Medicine, The Journal of Nuclear Medicine, vol. 49, No. 8, pp. 1371-1379.
Levin, Carly S. et al., "Magnetic-Plasmonic Core-Shell Nanoparticles," copyright 2009, American Chemical Society, ACS Nano, vol. 3, No. 6, pp. 1379-1388.
Merchant, B., "Gold, the Noble Metal and the Paradoxes of Its Toxicology," copyright 1998, The International Association of Biological Standardization, Biologicals, vol. 26, pp. 49-59.
Merrill, E.W. et al., "Platelet-Compatible Hydrophilic Segmented Polyurethanes From Polyethylene Glycols and Coclohexane Diisocyanate," copyright 1982, Trans. Am. Soc. Artif, Intern. Organs, vol. 28, pp. 482-487.
Millstone, Jill E. et al., "Observation of a Quadruple Plasmon Mode for a Colloidal Solution of Gold Nanoprisms," copyright 2005, J. Am. Chem. Soc., vol. 127, pp. 5312-5313.
Moghimi, S.M. et al., "Coating Particles With a Block Co-Polymer (Poloxamine-908) Suppresses Opsonization but Permits the Activity of Dysopsonins in the Serum," copyright 1993, Elsevier Science Publishers B.V., Biochimica et Biophysica Acta, vol. 1179, pp. 157-165.
Neeves, A.E. et al., "Composite Structures for the Enhancement of Nonlinear-Optical Susceptibility," copyright 1989, Optical Society of America, J. Opt. Soc. Am. B, vol. 6, No. 4, pp. 787-796.
Nie, Shuming et al., "Nanotechnology Applications in Cancer," copyright 2007, The Annual Review of Biomedical Engineering, vol. 9, pp. 257-288.
O'Donoghue, Meghan B. et al., "Nanoparticles for Multiplex Diagnostics and Imaging," copyright 2006, Nanomedicine, 1.4, pp. 1-17.
Paciotti, Giulio F. et al., "Colloidal Gold Nanoparticles: A Novel Nanoparticle Platform for Developing Multifunctional Tumor-Targeted Drug Delivery Vectors," copyright 2006, Wiley-Liss, Inc., Drug Development Research, vol. 67, pp. 47-54.
Paciotti, Giulio F. et al., "Colloidal Gold: A Novel Nanoparticle Vactor for Tumor Directed Drug Delivery," copyright 2004, Taylor & Francis, Inc., Drug Delivery, vol. 11, pp. 169-183.
Papahadjopoulos, D. et al., "Sterically Stabilized Liposomes: Improvements in Pharmacokinetics and Antitumor Therapeutic Efficacy," copyright 1991, Proc. Nati. Acad. Sei. USA, vol. 88, pp. 11460-11464.
Perrault, Steven D. et al., "Mediating Tumor Targeting Efficiency of Nanoparticles Through Design," copyright 2009, American Chemical Society, Nano Letters 2009, vol. 9, No. 5, pp. 1909-1915.

(56) References Cited

OTHER PUBLICATIONS

Porter, Marc D. et al., "SERS as a Bioassay Platform: Fundamentals, Design, and Applications," copyright 2008, The Royal Society of Chemistry, Chem. Soc. Review, vol. 37, pp. 1001-1011.
Prodan, E. et al., "A Hybridization Model for the Plasmon Response of Complex Nanostructures," copyright 2003, Science, vol. 302, pp. 419-422.
Qian, Ximei et al., "In Vivo Tumor Targeting and Spectroscopic Detection With Surface-Enhanced Raman Nanoparticle Tags," copyright 2008, Nature Biotechnology, vol. 26, No. 1, pp. 83-90.
Radloff, Corey et al., "Plasmonic Properties of Concentric Nanoshells," copyright 2004, American Chemical Society, Nano Letters 2004, vol. 4, No. 7, pp. 1323-1327.
Rauscher, M. et al., "Wetting Phenomena in Nanofluids," copyright 2008, The Annual Review of Materials Research, vol. 38, pp. 143-172.
Rodriguez-Fernandez, Jessica et al., "The Effect of Surface Roughness on the Plasmonic Response of Individual Sub-Micron Gold Spheres," copyright 2009, The Owner Societies, Physical Chemistry Chemical Physics, vol. 11, pp. 5909-5914.
Chen et al., Facile Synthesis of Gold-Silver Nanocages with Controllable Pores on the Surface, Oct. 28, 2006, JACS, pp. 14776-14777.
Wang, H. et al., "Light Scattering From Spherical Plasmonic Nanoantennas: Effects of Nanoscale Roughness," copyright 2006, Springer-Verlag, Appl. Phys. B, vol. 84, pp. 191-195.
Wang, Hui et al,. "Mesoscopic Au 'Meatball' Particles," copyright 2008, Wiley-VCH Verlag GmbH & Co. KgaA, Adv. Mater., vol. 20, pp. 820-825.
Wang, Qingtao et al., "Controllable Template Synthesis of Ni/Cu Nanocable and Ni Nanotube Arrays: A One-Step Coelectrodeposition and Electrochemical Etching Method," copyright 2005, American Chemical Society, J. Phys. Chem. B, vol. 109, pp. 23326-23329.
Wu, Yanpeng et al., "Plasmon Hybridization in Nanoshells With a Nonconentric Core," copyright 2006, American Institute of Physics, The Journal of American Physics, vol. 125, pp. 144708-1-124708-10.
Xiao, Ming et al., "Gold Nanotags for Combined Multi-Colored Raman Spectroscopy and X-Ray Computed Tomography," copyright 2010, IOP Publishing Ltd., Nanotechnology, vol. 21, pp. 1-8.
Xu, Zhichuan et al., "Magnetic Core/Shell Fe3O4/Au/Ag Nanoparticles With Tunable Plasmonic Properties," copyright 2007, J. Am. Chem. Soc., vol. 129, pp. 8698-8699.
Yang, Shangjiong et al., "Characterization of Nanobubbles on Hydroponic Surfaces in Water," copyright 2007, American Chemical Society, Langmuir, vol. 23, pp. 7072-7077.
Yavuz, Mustafa S. et al., "Gold Nanocages Covered by Smart Polymers for Controlled Release With Near-Infrared Light," copyright 2009, Nature Materials, vol. 8, pp. 935-939.
Yu, Kefeng et al., "Morphologies and Surface Plasmon Resonance Properties of Monodisperse Bumpy Gold Nanoparticles," copyright 2008, American Chemical Society, Langmuir, vol. 24, pp. 5849-5854.
Yu, Kyeong Nam et al., "Multiplex Targeting, Tracking, and Imaging of Apoptosis by Fluorescent Surface Enhanced Raman Spectroscopic Dots," copyright 2007, American Chemical Society, Bioconjugate Chem., vol. 18, pp. 1155-1162.
Zhang, Lijuan et al., "Electrochemically Controlled Formation and Growth of Hydrogen Nanobubbles," copyright 2006, American Chemical Society, Langmuir, vol. 22, pp. 8109-8113.

* cited by examiner

Figure 1A
Cell
Figure 1B
Enlargement
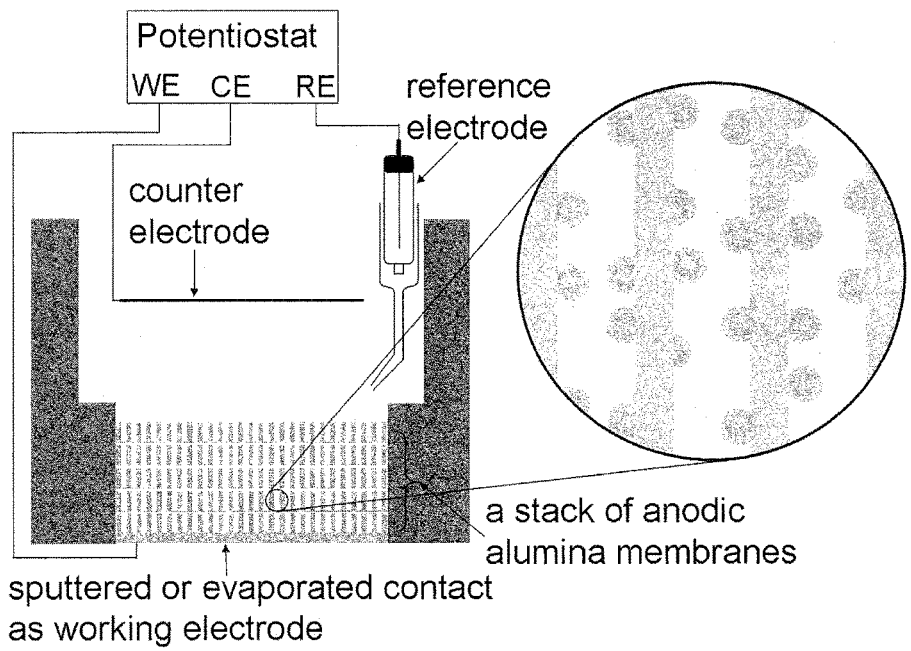
Figure 8A
Cell
Figure 8B
Enlargement
Figure 8C
SEM
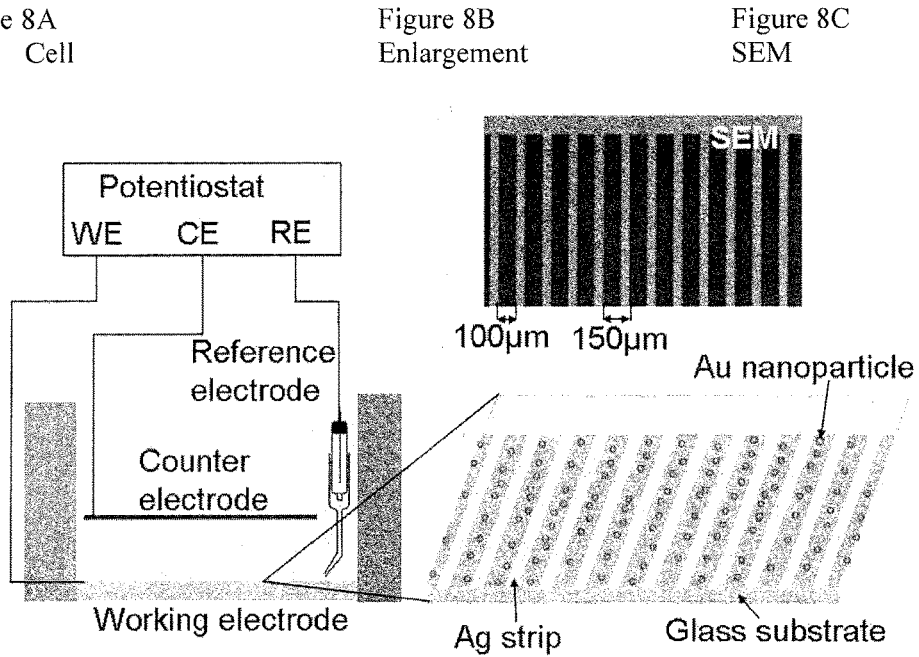

Figure 2A  Figure 2B
Top  Cross Section
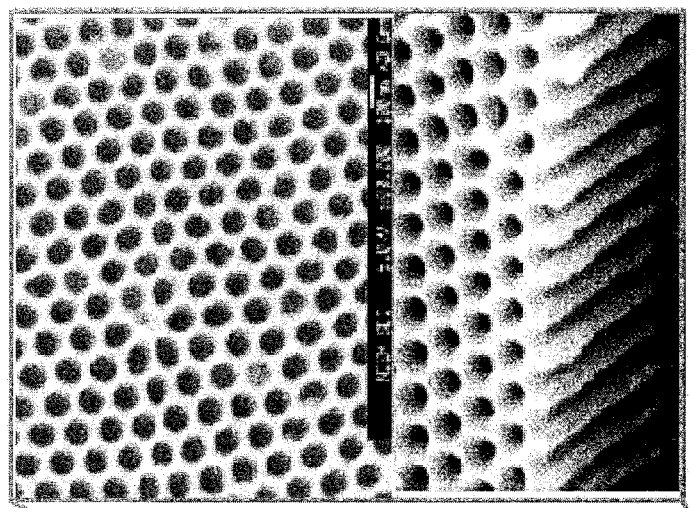
Figure 3A
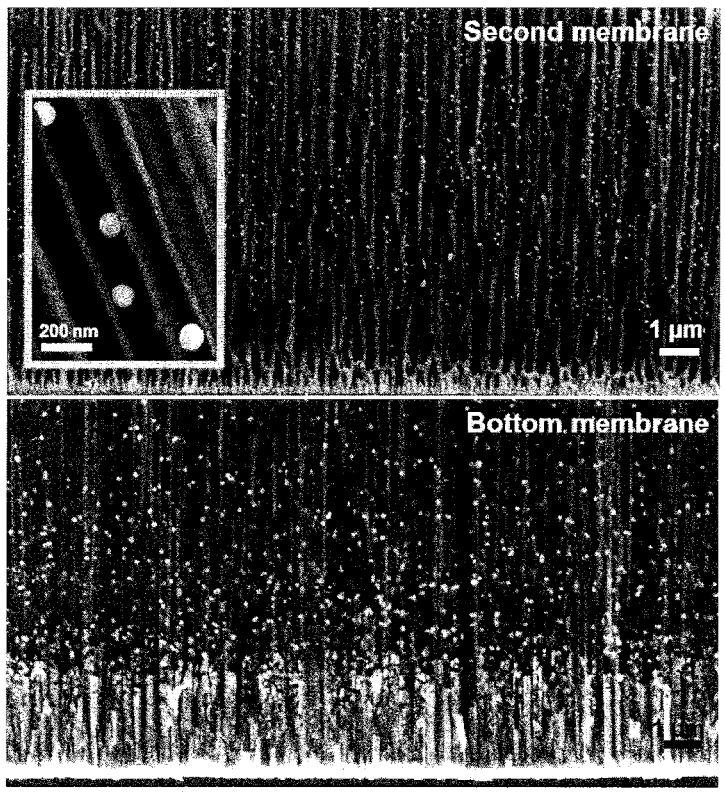
Branches
Figure 3B
Branches Mask Patterned Substrate Figure 11A
Figure 11B
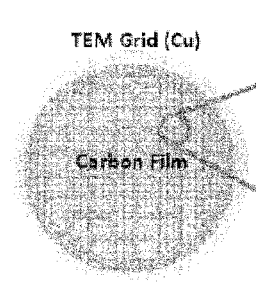
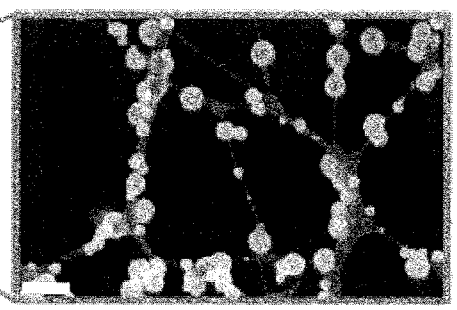
Figure 12A
Figure 12B
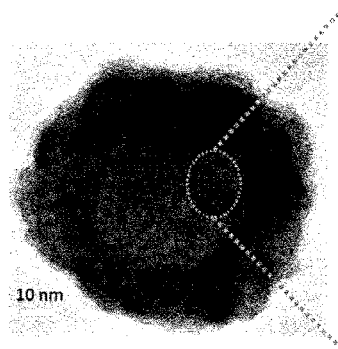
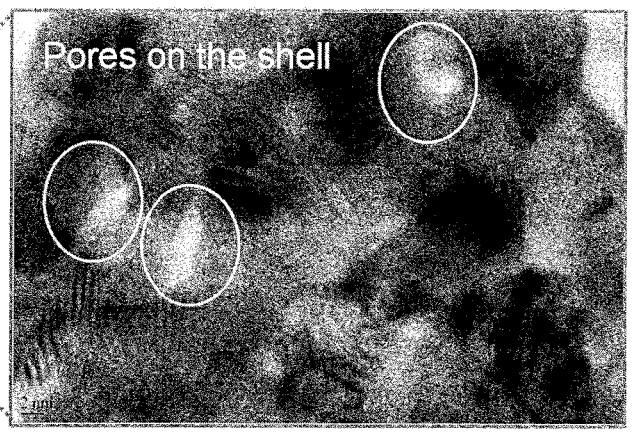

Figure 14C
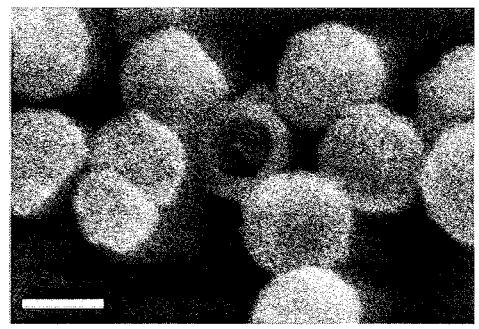
Figure 14D
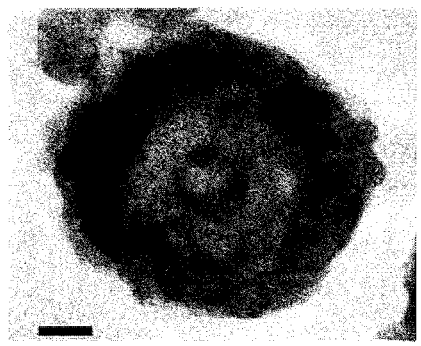
Figure 15A
Figure 15B
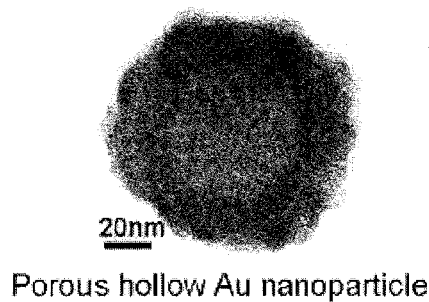
Porous hollow Au nanoparticle
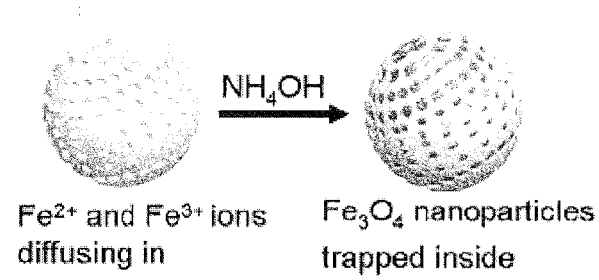
Fe²⁺ and Fe³⁺ ions diffusing in
Fe₃O₄ nanoparticles trapped inside Figure 26A
Figure 26B
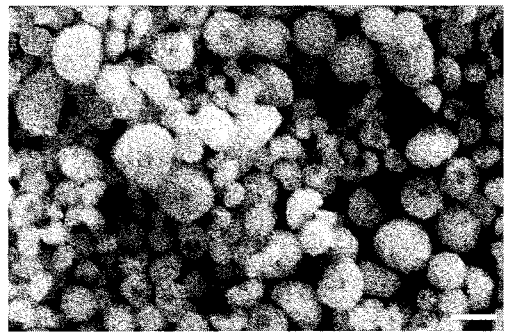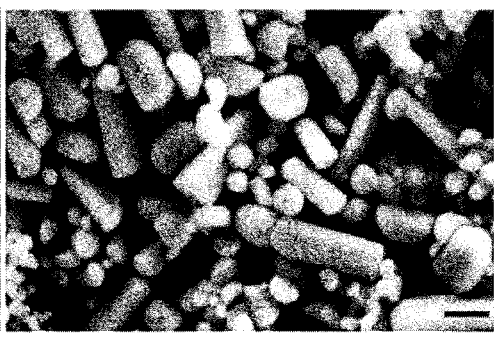
Figure 27
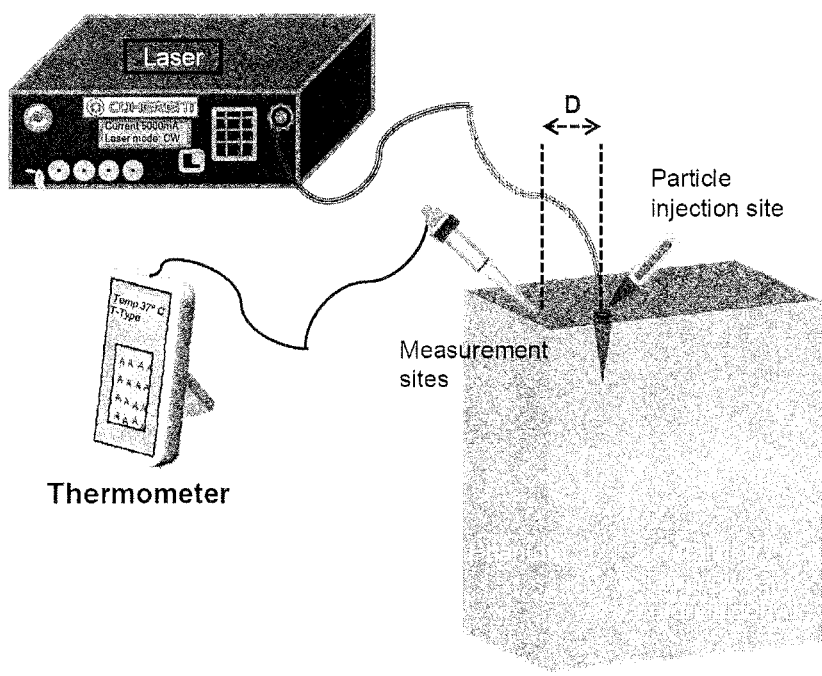

Figure 36
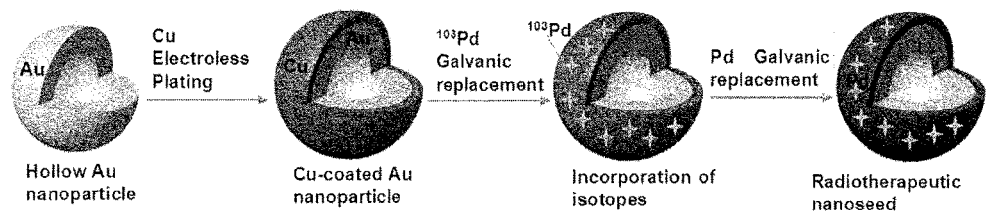
Figure 37
Figure 38
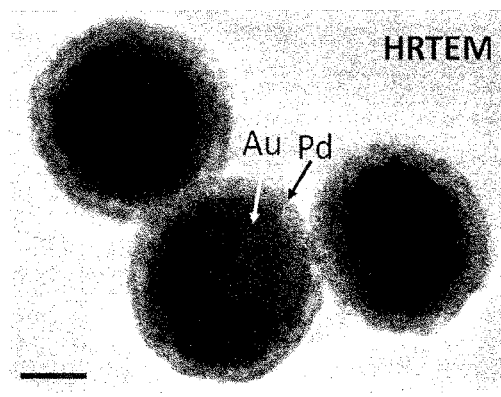
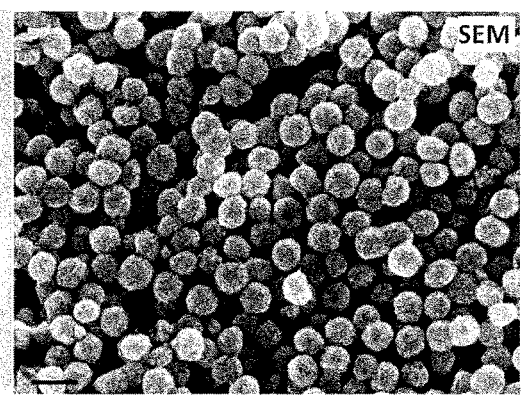

RADIOACTIVE NANOPARTICLES AND METHODS OF MAKING AND USING THE SAME

CROSS-REFERENCE TO RELATED APPLICATIONS

This application is a continuation-in-part of U.S. patent application Ser. No. 13/161,251, filed on Jun. 15, 2011, which claims priority pursuant to 35 U.S.C. §119(e) to U.S. Provisional Patent Application Ser. No. 61/355,364, filed on Jun. 16, 2010, each of which is hereby incorporated by reference in its entirety.

STATEMENT REGARDING FEDERALLY SPONSORED RESEARCH

This invention was made with government support under contract ECCS-0901849 awarded by the National Science Foundation. The government has certain rights in the invention.

FIELD OF THE INVENTION

The present invention relates to radioactive nanoparticles and methods of making and using radioactive nanoparticles, including for brachytherapy.

BACKGROUND

The use of radioisotopes for the treatment of disease such as cancer dates back to the beginning of the 20th century. In particular, localized radiotherapy has become a standard treatment option for many cancers. To confine the radiation to tumor sites, two general approaches are currently used in clinical practice: (1) systemic radioisotope therapy using radiopharmaceuticals and (2) "sealed source" radiotherapy or brachytherapy. In the first approach, radioactive constructs are administered to a patient systemically. The administered constructs then target tumors through metabolism or specific biological events. Radionuclides emitting β-particle, α-particle, or Auger electrons have been used in this approach. Unfortunately, the targeting efficacy and retention rate of many radioactive drugs inside tumor sites remain major challenges. The undesired uptake of radiopharmaceuticals by normal tissue also remains a problem with the systemic radiotherapy approach.

In brachytherapy, radioactive sources are placed into or next to the tumor volume. In previous brachytherapy methods, radioisotopes are encapsulated in a millimeter sized metal container or capsule to ensure the radiation sources remain in a desired location, such as the implantation site. In addition, gamma or X-ray emitting radioisotopes are typically used in previous brachytherapy methods due to the need to penetrate the metal capsule. For clinical applications, the brachytherapy capsules or "seeds" are permanently placed in the tumor through a surgical procedure. The radiation emitted from the brachytherapy seeds is thus used to treat the tumor "from the inside out," without traversing as much normal tissues as in external radiation therapy. However, the surgical implantation of millimeter sized brachytherapy seeds can cause many adverse side effects and greatly limits the application of brachytherapy for different tumor types, sizes, and locations.

Therefore, there remains a need for improved radioactive compositions, including for medical applications such as the radiation treatment of disease.

SUMMARY

In one aspect, radioactive nanoparticles are described herein which, in some cases, can provide one or more advantages compared to some other nanoparticles. For example, in some instances, a radioactive nanoparticle described herein can enable non-surgical brachytherapy. In particular, a radioactive nanoparticle described herein can be injectable into a tumor site as a highly dispersed and homogeneous solution or colloid. Moreover, the radioactive nanoparticle can be retained at the injection site for long periods of time. In this manner, a composition described herein can avoid some complications and adverse effects associated with surgery while also providing improved therapeutic effectiveness. Further, radioactive nanoparticles described herein may also expand the ability of brachytherapy to be used for tumors having small sizes and/or tumors that are located within regions of a patient that are more difficult to safely access by surgical means. In addition, radioactive nanoparticles described herein can also permit brachytherapy to be carried out using radioisotopes that are β-emitters, rather than emitters of gamma rays or X-rays. Thus, compositions described herein can substantially expand the range of brachytherapy modalities. Other advantages of radioactive nanoparticles of the present disclosure are further described hereinbelow.

In some embodiments, a radioactive nanoparticle described herein comprises a metal nanoparticle core, an outer metal shell disposed over the metal nanoparticle core, and a metallic radioisotope disposed within the metal nanoparticle core or within the outer metal shell. In addition, in some embodiments, a radioactive nanoparticle described herein further comprises an inner metal shell disposed between the metal nanoparticle core and the outer metal shell. As described further hereinbelow, the metal nanoparticle core, the outer metal shell, and the inner metal shell can comprise or be formed from a variety of metals. Further, the core, outer shell, and inner shell can have the same or differing metallic compositions. Moreover, in some cases, a radioactive nanoparticle described herein has a size of about 30-500 nm or about 80-200 nm in three dimensions. Further, in some instances, a composition described herein comprises a plurality or population of radioactive nanoparticles, and the plurality or population of radioactive nanoparticles exhibits a narrow size distribution.

In another aspect, methods of making a radioactive nanoparticle are described herein. In some embodiments, a method of making a radioactive nanoparticle comprises providing a metal nanoparticle core and forming an inner metal shell over the metal nanoparticle core through electroless deposition of a first metal or combination of metals. In particular, the first metal or combination of metals can be deposited onto an exterior surface of the metal nanoparticle core. The method also comprises forming an outer metal shell over the metal nanoparticle core. Specifically, the outer metal shell can be formed through galvanic replacement of at least a portion of the inner metal shell with a second metal or combination of metals, wherein the second metal or combination of metals comprises a metallic radioisotope. In addition, in some cases, the second metal or combination of metals further comprises a non-radioactive metallic isotope. Further, in some instances, forming the outer metal shell comprises carrying out a first galvanic replacement reaction between the inner metal shell and the metallic radioisotope, and subsequently carrying out a second galvanic replacement reaction between the inner metal shell and the non-radioactive metallic isotope. Moreover, as described further hereinbelow, the amount of the metallic radioisotope can be small compared to the amount of non-radioactive metallic isotope used to form the outer shell. Additionally, in some embodiments, methods of making a radioactive nanoparticle described herein can be carried out without the use of a non-metallic reducing agent.

In yet another aspect, methods of performing brachytherapy are described herein. In some cases, such a method comprises disposing a composition described herein within a biological compartment such as a tumor. In particular, the composition can comprise a plurality of radioactive nanoparticles described herein. For example, in some instances, at least one of the plurality of radioactive nanoparticles comprises a metal nanoparticle core, an outer metal shell disposed over the metal nanoparticle core, and a metallic radioisotope disposed within the metal nanoparticle core or within the outer metal shell. Further, in some cases, the radioactive nanoparticle has a size of about 30-500 nm in three dimensions. Moreover, in some embodiments, the composition is a colloidal dispersion of the plurality of radioactive nanoparticles. In addition, in some cases, at least about 80% of the radioactive nanoparticles are retained within the tumor or other biological compartment for at least 3 weeks following the time the radioactive nanoparticles were disposed in the tumor or other biological compartment.

These and other embodiments are described in greater detail in the detailed description and examples which follow.

BRIEF DESCRIPTION OF THE DRAWINGS

FIG. 1A illustrates a three-electrode cell suitable for use in some methods described herein. FIG. 1B is an enlarged view of several channels in a stacked membrane in the cell of FIG. 1A.

FIG. 2A is a scanning electron microscopy (SEM) image showing a top view of an alumina membrane suitable for use in some methods described herein. FIG. 2B is an SEM image showing a cross section of an alumina membrane suitable for use in some methods described herein.

FIG. 3A is an SEM image of an alumina membrane suitable for use in some methods described herein. Scale bar=1 µm. Inset is an enlarged view. Inset scale bar=200 nm. FIG. 3B is an SEM image of an alumina membrane suitable for use in some methods described herein. Scale bar=1 µm.

FIG. 8A illustrates a three-electrode cell suitable for use in some methods described herein. FIG. 8B is an enlarged view of a silver/glass substrate in the cell of FIG. 8A. FIG. 8C is an SEM image of a patterned substrate suitable for use in some methods described herein.

FIG. 11A illustrates a TEM grid suitable for use in some methods described herein, comprising copper mesh and carbon film. FIG. 11B is an SEM image of Au nanoparticles according to some embodiments described herein, on the carbon film of a TEM grid suitable for use in some methods described herein. Scale bar=1 µm.

FIG. 12A is a TEM image of a hollow Au nanoparticle with a porous shell according to some embodiments described herein. Scale bar=10 nm. FIG. 12B is a High Resolution TEM (HR-TEM) image of a hollow Au nanoparticle with a porous shell according to some embodiments described herein. Scale bar=2 nm.

FIG. 14C is an SEM image of double-shell nanoparticles according to some embodiments described herein. Scale bar=100 nm. FIG. 14D is a TEM image of a double-shell nanoparticle according to some embodiments described herein. Scale bar=20 nm.

FIG. 15A is a TEM image of a porous nanoparticle according to some embodiments described herein. Scale bar=20 nm. FIG. 15B illustrates a method of making a composite particle according to one embodiment described herein.

FIG. 26A is an SEM image of nanoparticles according to some embodiments described herein. Scale bar=100 nm. FIG. 26B is an SEM image of nanoparticles according to some embodiments described herein. Scale bar=100 nm.

FIG. 27 illustrates an experiment for measuring photothermal properties according to some embodiments described herein.

FIG. 36 illustrates schematically a method of making a radioactive nanoparticle according to one embodiment described herein.

FIG. 37 is a TEM image of non-radioactive nanoparticles corresponding to radioactive nanoparticles according to one embodiment described herein. The scale bar inset corresponds to 50 nm.

FIG. 38 is an SEM image of non-radioactive nanoparticles corresponding to radioactive nanoparticles according to one embodiment described herein. The scale bar inset corresponds to 200 nm.

DETAILED DESCRIPTION

Figure 4:
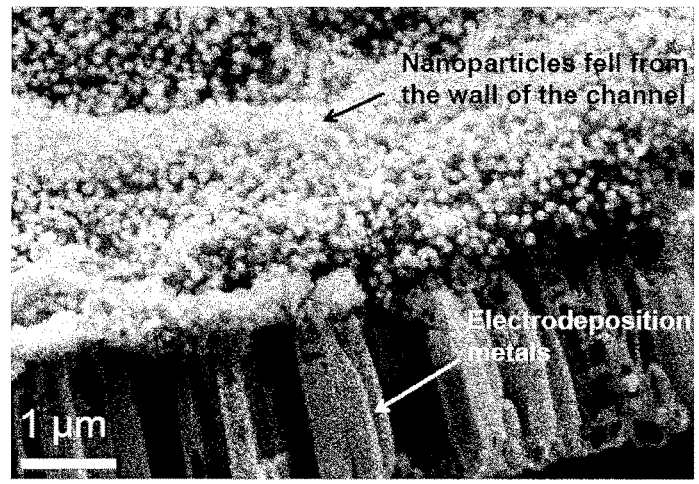
FIG. 4 is an SEM image of hollow gold (Au) nanoparticles according to some embodiments described herein, on electrodeposited metal. Scale bar=1 µm.
Figure 5A:
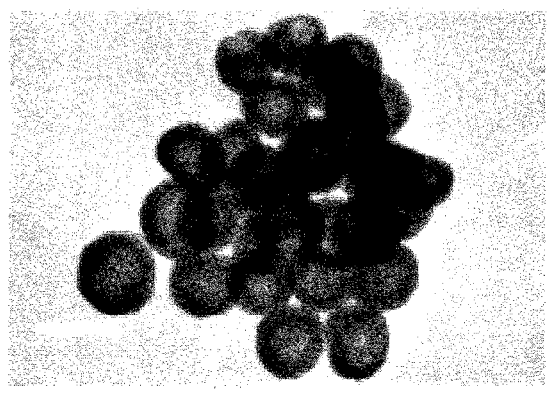
FIG. 5A is a transmission electron microscopy (TEM) image of hollow Au nanoparticles according to some embodiments described herein. Scale bar=100 nm.
Figure 5B:
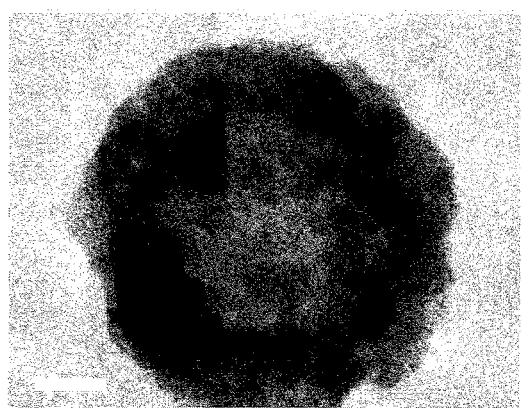
FIG. 5B is a TEM image of a hollow nanoparticle according to some embodiments described herein. Scale bar=10 nm.
Figure 5C:
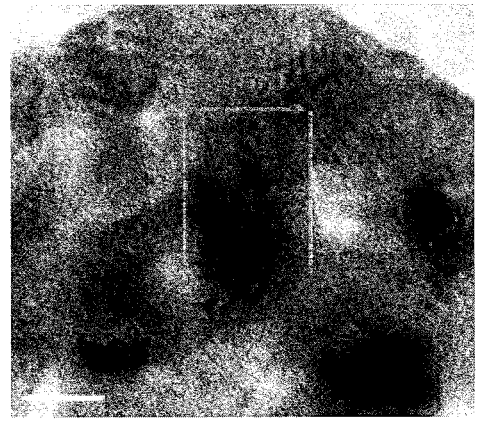
FIG. 5C is a TEM image of a hollow nanoparticle according to some embodiments described herein. Scale bar=5 nm.
Figure 5D:
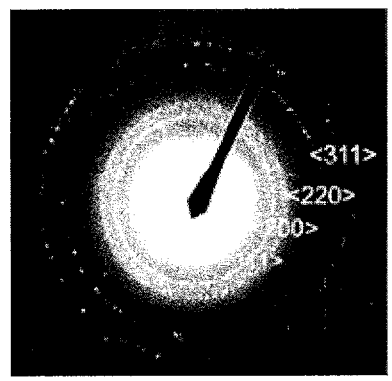
FIG. 5D is a selected area electron diffraction (SAED) pattern of hollow Au nanoparticles according to some embodiments described herein.

Embodiments described herein can be understood more readily by reference to the following detailed description, drawings, and examples and their previous and following descriptions. Elements, apparatus, and methods described herein, however, are not limited to the specific embodiments presented in the detailed description, drawings, and examples. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Hollow Nanoparticles

In one aspect, hollow nanoparticles are described herein which, in some embodiments, may offer one or more advantages over prior nanoparticles. In some embodiments, for example, a hollow nanoparticle described herein exhibits an SPR peak tunable from about 600 nm to about 900 nm, thereby providing properties useful in various imaging, therapeutic, theranostic, and sensing applications. In some embodiments, a hollow nanoparticle described herein exhibits desirable magnetic and/or photothermal properties. In some embodiments, a hollow nanoparticle described herein is useful for magnetic resonance imaging (MRI) and positron emission tomography (PET). In some embodiments, a hollow nanoparticle described herein exhibits desirable catalytic properties. In some embodiments, a hollow nanoparticle described herein is non-toxic. In some embodiments, a hollow nanoparticle described herein is operable for photothermal therapy.

In some embodiments, a hollow metal nanoparticle comprises a metal shell and a cavity substantially defined by the shell, wherein the shell has a thickness greater than or equal to about 5 nm and the cavity has a curved surface. In some embodiments, a hollow metal nanoparticle comprises a metallic shell and a cavity substantially defined by the shell, wherein the shell has a thickness greater than or equal to about 5 nm and the cavity has a curved surface. In some embodiments, a hollow nanoparticle comprises a polycrystalline metal shell and a cavity substantially defined by the shell, wherein the cavity has a curved surface. In some embodiments, a hollow nanoparticle comprises a polycrystalline metallic shell and a cavity substantially defined by the shell, wherein the cavity has a curved surface.

Hollow metal nanoparticles described herein, in some embodiments, have a cavity exhibiting various morphologies. In some embodiments, for example, the cavity is substantially spherical or hemispherical. In some embodiments, the cavity is substantially parabolic, elliptical, or ellipsoidal. In some embodiments, the cavity comprises a polygonal or faceted surface. The cavity, in some embodiments, exhibits various sizes. In some embodiments, the cavity has a diameter of about 50 nm to about 300 nm. In some embodiments, the cavity has a diameter of about 50 nm.

Hollow metal nanoparticles described herein, in some embodiments, exhibit various morphologies. In some embodiments, a hollow metal nanoparticle described herein is substantially hemispherical. In some embodiments, the nanoparticle is substantially tubular. In some embodiments, the nanoparticle comprises a curved exterior surface. In some embodiments, the nanoparticle is substantially spherical. In some embodiments, the nanoparticle comprises a parabolic exterior surface. In some embodiments, the nanoparticle is substantially elliptical or ellipsoidal.

Hollow metal nanoparticles described herein, in some embodiments, have various sizes. In some embodiments, a hollow metal nanoparticle comprising a metal shell and a cavity substantially defined by the shell has a diameter of about 50 nm to about 1000 nm. In some embodiments, the hollow nanoparticle has a diameter of about 50 nm to about 160 nm, about 60 nm to about 160 nm, about 80 nm to about 160 nm, or about 100 nm to about 150 nm. In some embodiments, the hollow nanoparticle has a diameter of about 60 nm to about 100 nm.

In some embodiments, a substantially tubular hollow nanoparticle has a diameter ranging from about 100 nm to about 400 nm and a length ranging from about 500 nm to about 2 µm. In some embodiments, a substantially tubular hollow nanoparticle has a length of about 1 µm.

In some embodiments, a plurality of hollow nanoparticles described herein has a narrow size distribution. In some embodiments, a plurality of hollow nanoparticles described herein has a size distribution with a standard deviation not greater than about 20%. In some embodiments, a plurality of hollow nanoparticles described herein has a size distribution with a standard deviation not greater than about 15%, not greater than about 10%, or not greater than about 5%. In some embodiments, a plurality of hollow nanoparticles described herein has a size distribution of 106 nm±10 nm, wherein 106 nm is the mean diameter and 10 nm is the standard deviation.

Hollow metal nanoparticles described herein, in some embodiments, exhibit various shell structures. In some embodiments, a shell of a hollow metal nanoparticle is porous. In some embodiments, for example, the shell has pores having a size between about 0.5 nm and about 3 nm. In some embodiments, the shell has pores having a size between about 2 nm and about 3 nm. In some embodiments, the shell of a hollow metal nanoparticle is non-porous. In some embodiments, the shell is polycrystalline. In some embodiments, the shell has a grain size of about 3 nm to about 8 nm. In some embodiments, the shell has a grain size of about 5 nm to about 8 nm. In some embodiments, the shell has a grain size less than about 5 nm. In some embodiments, the shell is single crystalline.

Hollow metal nanoparticles described herein, in some embodiments, exhibit various shell thicknesses. In some embodiments, a shell of a hollow metal nanoparticle has a thickness of about 5 nm to about 1000 nm. In some embodiments, the shell has a thickness greater than about 20 nm. In some embodiments, the shell has a thickness of about 5 nm to about 8 nm. In some embodiments, the shell has a thickness of about 5 nm to about 20 nm, about 8 nm to about 25 nm, about 8 nm to about 45 nm, about 25 nm to about 45 nm, about 25 nm to about 500 nm, about 25 nm to about 1000 nm, about 45 nm to about 300 nm, about 45 nm to about 500 nm, or about 45 nm to about 1000 nm.

Hollow metal nanoparticles described herein, in some embodiments, exhibit various surface roughnesses. In some embodiments, surface roughness values described herein are based on the grain size of the surface measured by HR-TEM. In some embodiments, for example, a surface roughness of about 5 nm corresponds to a measured grain size of about 5 nm. In some embodiments, a hollow metal nanoparticle described herein has a surface roughness less than about 5 nm. In some embodiments, a nanoparticle has a surface roughness between about 3 nm and about 8 nm. In some embodiments, a nanoparticle has a surface roughness of about 5 nm to about 8 nm. In some embodiments, a nanoparticle has a surface roughness less than about 3 nm or more than about 8 nm.

Hollow metal nanoparticles described herein, in some embodiments, comprise shells having various compositions. In some embodiments, for example, the shell of a hollow metal nanoparticle described herein comprises one or more of iron (Fe), cobalt (Co), nickel (Ni), palladium (Pd), platinum (Pt), copper (Cu), silver (Ag), gold (Au), zinc (Zn), and tin (Sn). In some embodiments, the shell comprises Au. In some embodiments, the shell comprises a metal capable of undergoing deposition by an oxidation-reduction reaction. In some embodiments, the shell comprises a metal capable of undergoing electroless deposition. In some embodiments, the shell comprises a plurality of metals having substantially similar reduction potentials.

Hollow metal nanoparticles described herein, in some embodiments, exhibit various optical properties. In some embodiments, a hollow metal nanoparticle described herein exhibits an absorption profile comprising a surface plasmon resonance (SPR) peak. In some embodiments, for example, a hollow metal nanoparticle comprising a metal shell described herein exhibits a surface plasmon resonance peak between about 600 nm and about 900 nm. In some embodiments, the nanoparticle exhibits a surface plasmon resonance peak between about 600 nm and about 750 nm. In some embodiments, the nanoparticle exhibits a surface plasmon resonance peak between about 650 nm and about 900 nm. In some embodiments, the nanoparticle exhibits a surface plasmon resonance peak between about 700 nm and about 800 nm Hollow nanoparticles described herein, in some embodiments, comprise various materials within the cavity defined by the metal shell. Any material not incompatible with the objectives of the present invention may be used in some embodiments. In some embodiments, the cavity comprises one or more of a gas, a nanoparticle, a therapeutic agent, an enzyme, a catalyst, and a dye. In some embodiments, the cavity comprises a gas. In some embodiments, the gas comprises a reducing gas. In some embodiments, the reducing gas is capable of reducing one or more of the metals from a higher oxidation state to a lower oxidation state. In some embodiments, the reducing gas is capable of reducing one or more of the metals from a positive oxidation state to an oxidation state of zero. In some embodiments, for example, the gas comprises $H_2$. In some embodiments, the gas comprises $NH_3$. In some embodiments, the gas comprises an electrochemically generated gas.

In some embodiments, a hollow metal nanoparticle described herein further comprises one or more additional nanoparticles at least partially disposed in the cavity defined by the metal shell. In some embodiments, a hollow metal nanoparticle described herein further comprises a plurality of second nanoparticles at least partially disposed in the cavity defined by the metal shell. In some embodiments, a hollow metal nanoparticle described herein further comprises at least one second nanoparticle at least partially disposed in the cavity defined by the metal shell. In some embodiments, at least one second nanoparticle comprises a cluster of nanoparticles. In some embodiments, at least one second nanoparticle comprises an organic nanoparticle. In some embodiments, at least one second nanoparticle comprises an inorganic nanoparticle. In some embodiments, at least one second nanoparticle comprises a semiconductor nanoparticle. In some embodiments, the second nanoparticle comprises a metal nanoparticle. In some embodiments, at least one second nanoparticle comprises a metal oxide nanoparticle. In some embodiments, at least one second nanoparticle comprises a ceramic nanoparticle. In some embodiments, at least one second nanoparticle comprises a quantum dot. In some embodiments, at least one second nanoparticle comprises a magnetic nanoparticle. In some embodiments, the magnetic nanoparticle is superparamagnetic. In some embodiments, the magnetic nanoparticle is ferromagnetic.

In some embodiments, at least one second nanoparticle can demonstrate various compositions. In some embodiments, at least one second nanoparticle comprises iron oxide. In some embodiments, at least one second nanoparticle comprises doped $Fe_3O_4$. In some embodiments, doped $Fe_3O_4$ comprises one or more nuclides useful for positron emission tomography (PET). In some embodiments, doped $Fe_3O_4$ comprises one or more of $^{64}Cu$, $^{89}Zr$, $^{11}C$, $^{18}F$, and $^{67}Ga$. In some embodiments, doped $Fe_3O_4$ comprises one or more of $^{64}Cu$ and $^{89}Zr$.

In some embodiments, at least one second nanoparticle comprises a second hollow metal nanoparticle. In some embodiments, the second hollow metal nanoparticle has substantially the same chemical composition as the shell.

In some embodiments wherein the hollow metal nanoparticle comprises at least one second nanoparticle, at least one second nanoparticle has a diameter of less than about 50 nm. In some embodiments, at least one second nanoparticle has a diameter of less than about 20 nm. In some embodiments, at least one second nanoparticle has a diameter between about 5 nm and about 20 nm or between about 30 nm and about 50 nm. In some embodiments, the shell is porous and at least one second nanoparticle has a diameter greater than the pore size.

In some embodiments, the cavity of a hollow metal nanoparticle described herein comprises a therapeutic agent. In some embodiments, the therapeutic agent comprises a gas. In some embodiments, the therapeutic agent comprises an aqueous solution. In some embodiments, the therapeutic agent comprises a drug.

Hollow metal nanoparticles described herein, in some embodiments, further comprise various species associated with one or more outer surfaces of the nanoparticle. In some embodiments, one or more species are associated with an outer surface directly. In some embodiments, one or more species are associated with an outer surface indirectly. In some embodiments, one or more species are associated with an outer surface indirectly through one or more species that are associated with an outer surface directly. In some embodiments, at least one species associated with an outer surface comprises a targeting agent. In some embodiments, at least one species associated with an outer surface comprises a Raman active species. In some embodiments, at least one species associated with an outer surface comprises a polyethylene glycol moiety. In some embodiments, a first species associated with an outer surface comprises a Raman active species and forms a first layer and a second species associated with the outer surface comprises a polyethylene glycol moiety and forms a second layer, wherein the second layer substantially surrounds the first layer. In some embodiments, a first species associated with an outer surface comprises a polyethylene glycol moiety and a second species associated with the outer surface comprises a targeting agent.

II. Methods of Making Hollow Nanoparticles

In another aspect, methods of making hollow nanoparticles are described herein, which, in some embodiments, may offer one or more advantages over prior methods of making nanoparticles. In some embodiments, for example, a method of making hollow nanoparticles described herein is simple, efficient, scalable, inexpensive, and reproducible. In some embodiments, a method of making hollow nanoparticles comprises forming a plurality of gas bubbles and forming a shell on the surface of at least one of the plurality of gas bubbles to form a hollow nanoparticle, wherein at least one of the gas bubbles is electrochemically generated. In some embodiments, forming a plurality of gas bubbles comprises electrochemically forming a plurality of gas bubbles. In some embodiments, forming a shell on the surface of at least one of the plurality of gas bubbles to form a hollow nanoparticle comprises forming a shell on the surface of at least one electrochemically generated gas bubble. In some embodiments, the shell is metallic.

Methods of making hollow nanoparticles described herein, in some embodiments, comprise forming a plurality of gas bubbles having various physical and chemical properties. In some embodiments, at least one of the gas bubbles comprises a reducing gas. In some embodiments, at least one of the gas bubbles comprises $H_2$. In some embodiments, at least one of the gas bubbles comprises $NH_3$. In some embodiments, at least one of the gas bubbles comprises an oxidizing gas. In some embodiments, at least one of the gas bubbles comprises $O_2$. In some embodiments, at least one of the gas bubbles comprises a relatively inert gas. In some embodiments, at least one of the gas bubbles comprises $CO_2$.

In some embodiments, a method of making hollow nanoparticles described herein comprises forming a shell on at least one gas bubble having various sizes. In some embodiments, for example, at least one of the gas bubbles on which a shell is formed has a diameter between about 40 nm and about 60 nm. In some embodiments, at least one of the gas bubbles on which a shell is formed has a diameter between about 50 nm and about 300 nm. In some embodiments, at least one of the gas bubbles on which a shell is formed has a diameter of about 50 nm.

Methods of making hollow nanoparticles described herein, in some embodiments, comprise forming at least one gas bubble electrochemically at various applied potentials. In some embodiments, at least one of the gas bubbles is electrochemically generated at a potential more negative than the equilibrium potential. In some embodiments, at least one of the gas bubbles is electrochemically generated at a potential more negative than the equilibrium potential of gas evolution. In some embodiments, for example, at least one of the gas bubbles is electrochemically generated at a potential more negative than about −0.6 V relative to Ag/AgCl. In some embodiments, at least one of the gas bubbles is electrochemically generated at a potential between about −0.7 V and −0.85 V relative to Ag/AgCl. In some embodiments, at least one of the gas bubbles is electrochemically generated at a potential between about −0.55 V and −0.8 V relative to Ag/AgCl. In some embodiments, at least one of the gas bubbles is electrochemically generated at a potential more negative than about −0.6 V relative to Ag/AgCl at about 25° C. and a pH between about 5 and about 8. In some embodiments, at least one of the gas bubbles is electrochemically generated at a potential between about −0.7 V and −0.85 V relative to Ag/AgCl at about 25° C. and a pH between about 5 and about 8. In some embodiments, at least one of the gas bubbles is electrochemically generated at a potential between about −0.55 V and −0.8 V relative to Ag/AgCl at about 25° C. and a pH between about 5 and about 8.

In some embodiments, a method of making hollow nanoparticles comprises forming a plurality of gas bubbles and forming a shell on the surface of at least one of the plurality of gas bubbles to form a hollow nanoparticle, wherein at least one of the gas bubbles is electrochemically generated and wherein forming a shell comprises depositing material through one or more oxidation-reduction reactions. In some embodiments, forming a shell comprises depositing material through electroless deposition.

Methods of making hollow nanoparticles described herein, in some embodiments, further comprise providing an electrolyte having various properties and compositions. In some embodiments, forming the plurality of gas bubbles and forming the shell occurs in the presence of the electrolyte. In some embodiments, the electrolyte exhibits a pH between about 5 and about 8. In some embodiments, the electrolyte exhibits a pH between about 6 and about 7.

In some embodiments, the electrolyte comprises a metal-containing species. In some embodiments, the electrolyte comprises a metal-containing species capable of undergoing deposition through an oxidation-reduction reaction. In some embodiments, the electrolyte comprises a metal-containing species capable of undergoing electroless deposition. In some embodiments, the electrolyte comprises a metal-containing species comprising a metal capable of being reduced by $H_2$. In some embodiments, the electrolyte comprises a metal-containing species comprising a metal capable of being reduced by $NH_3$. In some embodiments, the electrolyte comprises a metal-containing species capable of being reduced by an aqueous reducing agent. In some embodiments, the electrolyte comprises a plurality of metal-containing species having substantially similar reduction potentials. In some embodiments, for example, each of the plurality of metal-containing species is capable of being reduced by the same reducing agent. In some embodiments, the electrolyte comprises a metal-containing species comprising a metal capable of being oxidized by $O_2$. In some embodiments, the electrolyte comprises a metal-containing species capable of being oxidized by an aqueous oxidizing agent. In some embodiments, the metal-containing species comprises one or more of Fe, Co, Ni, Pd, Pt, Cu, Ag, Au, Zn, and Sn. In some embodiments, the metal-containing species comprises Au. In some embodiments, the metal-containing species comprises one or more of titanium (Ti), zirconium (Zr), Fe, Co, Ni, Cu, Zn, and Sn.

In some embodiments, the electrolyte comprises a reducing agent. Any reducing agent not incompatible with the objectives of the present invention may be used.

In some embodiments, the reducing agent comprises one or more of phosphites, hypophosphites, hydrazines, borohydrides, cyanoborohydrides, trialkylamines and trialkylphosphines. In some embodiments, the reducing agent comprises one or more of glyoxylic acid, sodium hypophosphite ($Na_2H_2PO_2$), sodium hypophosphite monohydrate ($Na_2H_2PO_2.H_2O$), formaldehyde, sodium borohydride ($NaBH_4$), sodium cyanoborohydride ($NaBH_3(CN)$), hydrazine ($N_2H_4$), hydrazine monohydrate ($N_2H_4.H_2O$), hydrazine-borane, hydroxylamine hydrochloride, formic acid, trimethylamine borane (DMAB), thiourea, ascorbic acid, titanium trichloride, lithium aluminum hydride, triethylsilane, mercaptosuccinic acid, 9-borabicyclo[3.3.1]nonane, gelatin, and sodium citrate. In some embodiments, the electrolyte comprises an oxidizing agent. Any oxidizing agent not incompatible with the objectives of the present invention may be used. In some embodiments, the oxidizing agent comprises one or more of permanganates, chromates, dichromates, perchlorates, and peroxides.

In some embodiments, the electrolyte comprises a stabilizing ligand. In some embodiments, the stabilizing ligand is operable to stabilize one or more hollow nanoparticles against aggregation or agglomeration. In some embodiments, the stabilizing ligand comprises a species having a first end operable to associate with a surface of one or more hollow nanoparticles and a second end operable to interact with solution. In some embodiments, the stabilizing ligand comprises a surfactant. In some embodiments, the stabilizing ligand comprises a thiol. In some embodiments, the stabilizing ligand comprises one or more of an amine, a phosphine, a carboxylic acid, and a carboxylate. Non-limiting examples of stabilizing ligands suitable for use in some embodiments include mercaptoacetic acid, mercaptopropionic acid, hexadecylamine, triphenylphosphine, cetyltrimethylammonium bromide, citric acid and sodium citrate.

In some embodiments, a method of making hollow nanoparticles comprises forming a plurality of gas bubbles, and forming a shell on the surface of at least one of the plurality of gas bubbles to form a hollow nanoparticle, wherein at least one of the gas bubbles is electrochemically generated and wherein forming the plurality of gas bubbles and forming the shell occurs in the presence of an electrolyte, the electrolyte comprising a metal-containing species and one or more promoters. In some embodiments, at least one promoter comprises ethylenediamine (EDA). In some embodiments, at least one promoter comprises ethylenediaminetetraacetic acid (EDTA). In some embodiments, at least one promoter comprises $(SO_3)^{2-}$. In some embodiments, at least one promoter comprises one or more of $Ni^{2+}$, $Pd^{2+}$, and $Pt^{2+}$. In some embodiments, at least one promoter comprises $Ni^{2+}$.

Methods of making hollow nanoparticles described herein, in some embodiments, comprise providing one or more nucleation substrates. In some embodiments, forming a plurality of gas bubbles comprises forming at least one gas bubble on at least one nucleation substrate. In some embodiments, at least one nucleation substrate comprises a solid surface. In some embodiments, at least one nucleation substrate comprises a surface that operates as a working electrode. In some embodiments, the nucleation substrate comprises at least one surface that does not operate as an electrode.

In some embodiments, at least one nucleation substrate comprises an organic polymer. In some embodiments, at least one nucleation substrate comprises an inorganic material. In some embodiments, at least one nucleation substrate comprises a nanoparticle. In some embodiments, at least one nucleation substrate comprises silver (Ag). In some embodiments, at least one nucleation substrate comprises silicon (Si). In some embodiments, at least one nucleation substrate comprises silica ($SiO_2$). In some embodiments, at least one nucleation substrate comprises titania ($TiO_2$). In some embodiments, at least one nucleation substrate comprises alumina ($Al_2O_3$). In some embodiments, at least one nucleation substrate comprises copper (Cu). In some embodiments, at least one nucleation substrate comprises carbon (C). In some embodiments, at least one nucleation substrate comprises a patterned substrate. In some embodiments, at least one nucleation substrate comprises a patterned glass substrate. In some embodiments, at least one nucleation substrate comprises a $SiO_2$ substrate comprising at least one Ag stripe. In some embodiments, at least one nucleation substrate comprises a TEM grid.

In some embodiments, at least one nucleation substrate comprises a membrane. In some embodiments, the membrane has a high surface area. In some embodiments, the membrane comprises a track etched membrane. In some embodiments, the membrane comprises polycarbonate. In some embodiments, the membrane comprises polyester. In some embodiments, the membrane comprises cellulose. In some embodiments, the membrane comprises one or more of regenerated cellulose, cellulose acetate, cellulose nitrate, and mixed cellulose ester. In some embodiments, the membrane comprises polytetrafluoroethylene (PTFE). In some embodiments, the membrane comprises polyamide. In some embodiments, the membrane comprises nylon. In some embodiments, the membrane comprises polyethersulfone (PES). In some embodiments, the membrane comprises polypropylene. In some embodiments, the membrane comprises porous glass. In some embodiments, the membrane comprises anodic aluminum oxide (AAO). In some embodiments, the membrane comprises pores having a diameter of about 100 nm to about 3000 nm. In some embodiments, the membrane comprises pores having a diameter of about 100 nm to about 500 nm.

Methods of making hollow nanoparticles described herein, in some embodiments, comprise providing a plurality of nucleation substrates. In some embodiments, the plurality of nucleation substrates comprises stacked membranes. In some embodiments, the plurality of nucleation substrates comprises stacked membranes comprising anodic aluminum oxide. Methods of making hollow nanoparticles described herein, in some embodiments, further comprise selectively dissolving one or more nucleation substrates following forming a shell.

In some embodiments, a method of making hollow nanoparticles comprises forming a plurality of gas bubbles, forming a shell on the surface of at least one of the plurality of gas bubbles to form a hollow nanoparticle, providing one or more precursors of at least one second nanoparticle, and forming at least one second nanoparticle from the one or more precursors within a cavity defined by the shell, wherein at least one of the gas bubbles is electrochemically generated. In some embodiments, the shell substantially surrounds at least one second nanoparticle. In some embodiments, providing one or more precursors of at least one second nanoparticle comprises providing a first precursor before providing a second precursor. In some embodiments, providing one or more precursors of at least one second nanoparticle comprises providing at least one aqueous solution of the one or more precursors.

In some embodiments, a method of making hollow nanoparticles comprises forming a plurality of gas bubbles, forming a shell on the surface of at least one of the plurality of gas bubbles to form a hollow nanoparticle, providing one or more precursors of a plurality of second nanoparticles, and forming the plurality of second nanoparticles from the one or more precursors within a cavity defined by the shell, wherein at least one of the gas bubbles is electrochemically generated. In some embodiments, the shell substantially surrounds the plurality of second nanoparticles.

Methods of making hollow nanoparticles described herein, in some embodiments, further comprise associating one or more species to one or more outer surfaces of the shell. In some embodiments, one or more species are associated with an outer surface of the shell directly. In some embodiments, one or more species are associated with an outer surface indirectly. In some embodiments, one or more species are associated with an outer surface indirectly through one or more species that are associated with the outer surface directly. In some embodiments, one or more species associated with an outer surface of the shell comprises a polyethylene glycol moiety. In some embodiments, one or more species associated with an outer surface of the shell comprises a targeting agent. In some embodiments, one or more species associated with an outer surface of the shell comprises a Raman active species.

In some embodiments of methods of making hollow nanoparticles described herein, the method is a one-pot method. In some embodiments, a one-pot method comprises forming the nanoparticles from one or more starting materials in one pot or in a single reaction vessel. In some embodiments, none of the starting materials in the single reaction vessel comprises a pre-formed nanoparticle. In some embodiments, none of the starting materials in the single reaction vessel comprises a solid pre-formed nanoparticle. In some embodiments of methods of making hollow nanoparticles described herein, the method is a one-step method. In some embodiments, a one-step method comprises forming the hollow nanoparticles without first making solid cores for the hollow nanoparticles.

In some embodiments, hollow nanoparticles made in accordance with one or more methods described herein can have any of the properties recited herein for hollow nanoparticles. For example, in some embodiments, a method of making hollow nanoparticles described herein comprises making hollow nanoparticles having a cavity having a size or shape as described herein. In some embodiments, a method of making hollow nanoparticles described herein comprises making hollow nanoparticles having a shell having a thickness or composition as described herein.

III. Composite Particles

In another aspect, composite particles are described herein, which, in some embodiments, may offer one or more advantages over prior composite particles. In some embodiments, for example, a composite particle described herein exhibits theranostic and/or dual imaging properties. In some embodiments, a composite particle described herein is useful for magnetic resonance imaging (MRI) and positron emission tomography (PET). In some embodiments, a composite particle described herein is non-toxic. In some embodiments, a composite particle described herein is operable for photothermal therapy.

In some embodiments, a composite particle comprises at least one nanoparticle and a polycrystalline metal shell substantially encapsulating at least one nanoparticle, wherein at least one surface of at least one nanoparticle is not in contact with the shell. In some embodiments, a composite particle comprises at least one nanoparticle and a metal shell substantially encapsulating at least one nanoparticle, wherein the metal shell has a thickness of about 10 nm to about 200 nm and at least one surface of the at least one nanoparticle is not in contact with the shell. In some embodiments, no surface of at least one nanoparticle is in contact with the shell. In some embodiments, no surface of any nanoparticle is in contact with the shell. In some embodiments, the shell is metallic.

In some embodiments, a composite particle comprises a plurality of nanoparticles and a polycrystalline metal shell substantially encapsulating the plurality of nanoparticles, wherein at least one surface of at least one nanoparticle is not in contact with the shell. In some embodiments, a composite particle comprises a plurality of nanoparticles and a metal shell substantially encapsulating the plurality of nanoparticles, wherein the metal shell has a thickness of about 10 nm to about 200 nm and at least one surface of at least one nanoparticle is not in contact with the shell. In some embodiments, no surface of at least one nanoparticle is in contact with the shell. In some embodiments, no surface of any nanoparticle is in contact with the shell. In some embodiments, the shell is metallic.

Composites described herein, in some embodiments, can exhibit various sizes and morphologies. In some embodiments, the composite particle is substantially spherical. In some embodiments, the composite particle is substantially spherical and has a diameter of about 60 nm to about 1000 nm. In some embodiments, the composite particle has a diameter of about 80 nm to about 160 nm, about 100 nm to about 150 nm, about 50 nm to about 100 nm, or about 50 nm to about 160 nm.

Composites described herein, in some embodiments, comprise shells having various thicknesses, morphologies, and compositions. In some embodiments, the shell is porous. In some embodiments, the shell has pores that are smaller than at least one nanoparticle. In some embodiments, the shell has pores ranging in size from about 0.5 nm to about 3 nm. In some embodiments, the shell has pores ranging in size from about 2 nm to about 3 nm. In some embodiments, the shell is non-porous.

In some embodiments, the shell is polycrystalline. In some embodiments, the shell is polycrystalline and has a grain size of about 3 nm to about 8 nm. In some embodiments, the shell is polycrystalline and has a grain size of about 5 nm to about 8 nm. In some embodiments, the shell is polycrystalline and has a grain size less than about 5 nm. In some embodiments, the shell is single crystalline.

In some embodiments, the shell has a thickness of about 10 nm to about 100 nm. In some embodiments, the shell has a thickness greater than about 20 nm. In some embodiments, the shell has a thickness between about 10 nm and about 20 nm. In some embodiments, the shell has a thickness of about 10 nm to about 45 nm, about 25 nm to about 45 nm, or about 45 nm to about 200 nm.

In some embodiments, the shell has a surface roughness of less than about 5 nm. In some embodiments, the shell has a surface roughness between about 5 nm and 8 nm. In some embodiments, the shell has a surface roughness between about 3 nm and about 8 nm. In some embodiments, the shell has a surface roughness less than about 3 nm. In some embodiments, the shell has a surface roughness greater than about 8 nm.

In some embodiments, the shell comprises one or more of Fe, Co, Ni, Pd, Pt, Cu, Ag, Au, Zn, and Sn. In some embodiments, the shell comprises Au.

Composite particles described herein, in some embodiments, exhibit various optical properties. In some embodiments, a composite particle described herein exhibits an absorption profile comprising a surface plasmon resonance peak. In some embodiments, the composite particle exhibits a surface plasmon resonance peak between about 600 nm and about 900 nm. In some embodiments, the composite particle exhibits a surface plasmon resonance peak between about 600 nm and about 750 nm. In some embodiments, the composite particle exhibits a surface plasmon resonance peak between about 650 nm and about 900 nm. In some embodiments, the composite particle exhibits a surface plasmon resonance peak between about 700 nm and about 800 nm.

Composite particles described herein, in some embodiments, comprise nanoparticles having various sizes, morphologies, compositions, and properties. In some embodiments, at least one nanoparticle is substantially spherical. In some embodiments, at least one nanoparticle is substantially spherical and has a diameter of less than about 50 nm. In some embodiments, at least one nanoparticle has a diameter of less than about 20 nm. In some embodiments, at least one nanoparticle has a diameter between about 5 nm and about 20 nm. In some embodiments, at least one nanoparticle has a diameter between about 30 nm and about 50 nm. In some embodiments, at least one nanoparticle comprises a cluster of nanoparticles.

In some embodiments, at least one nanoparticle comprises a magnetic nanoparticle. In some embodiments, the magnetic nanoparticle is superparamagnetic. In some embodiments, the magnetic nanoparticle is ferromagnetic. In some embodiments, at least one nanoparticle comprises iron oxide. In some embodiments, the nanoparticle comprises doped $Fe_3O_4$. In some embodiments, doped $Fe_3O_4$ comprises one or more nuclides useful for positron emission tomography (PET). In some embodiments, doped $Fe_3O_4$ comprises one or more of $^{64}Cu$, $^{89}Zr$, $^{11}C$, $^{18}F$, and $^{67}Ga$. In some embodiments, doped $Fe_3O_4$ comprises one or more of $^{64}Cu$ and $^{89}Zr$.

In some embodiments, at least one nanoparticle comprises an organic nanoparticle. In some embodiments, at least one nanoparticle comprises an inorganic nanoparticle. In some embodiments, at least one nanoparticle comprises a semiconductor nanoparticle. In some embodiments, at least one nanoparticle comprises a metal nanoparticle. In some embodiments, at least one nanoparticle comprises a metal oxide nanoparticle. In some embodiments, at least one nanoparticle comprises a ceramic nanoparticle. In some embodiments, at least one nanoparticle comprises a quantum dot.

Composite particles described herein, in some embodiments, further comprise various species associated with an outer surface of the composite particle. In some embodiments, one or more species are associated with an outer surface directly. In some embodiments, one or more species are associated with an outer surface indirectly. In some embodiments, one or more species are associated with an outer surface indirectly through one or more species that are associated with the outer surface directly. In some embodiments, at least one species associated with an outer surface comprises a Raman active species. In some embodiments, at least one species associated with an outer surface comprises a polyethylene glycol moiety. In some embodiments, at least one species associated with an outer surface comprises a targeting agent. In some embodiments, a first species associated with an outer surface comprises a Raman active species and forms a first layer and a second species associated with the outer surface comprises a polyethylene glycol moiety and forms a second layer, wherein the second layer substantially surrounds the first layer. In some embodiments, a first species associated with an outer surface comprises a polyethylene glycol moiety and a second species associated with the outer surface comprises a targeting agent.

IV. Methods of Making a Composite Particle

In another aspect, methods of making a composite particle are described herein, which, in some embodiments, may offer one or more advantages over prior methods of making a composite particle. In some embodiments, for example, a method of making a composite particle described herein is simple, efficient, scalable, inexpensive, and reproducible. In some embodiments, a method of making a composite particle comprises providing a porous hollow nanoparticle, providing one or more precursors of at least one second nanoparticle, mixing the one or more precursors with the hollow nanoparticle, and forming at least one second nanoparticle from the one or more precursors within the hollow nanoparticle. In some embodiments, a method of making a composite particle comprises providing a porous hollow nanoparticle, providing one or more precursors of a plurality of second nanoparticles, mixing the one or more precursors with the hollow nanoparticle, and forming the plurality of second nanoparticles from the one or more precursors within the hollow nanoparticle. In some embodiments, the hollow nanoparticle comprises any porous hollow nanoparticle described herein. In some embodiments, the hollow nanoparticle comprises a hollow metal nanoparticle. In some embodiments, the hollow nanoparticle comprises a hollow metallic nanoparticle. In some embodiments, the hollow nanoparticle comprises a hollow metal oxide nanoparticle. In some embodiments, the hollow nanoparticle comprises a hollow semiconductor nanoparticle.

Methods of making composite particles described herein, in some embodiments, comprise providing and mixing one or more precursors of at least one second nanoparticle in various forms and ways. In some embodiments, providing one or more precursors of at least one second nanoparticle comprises providing at least one aqueous solution of the one or more precursors. In some embodiments, mixing one or more precursors of at least one second nanoparticle comprises mixing a first precursor with the hollow nanoparticle before mixing a second precursor with the hollow nanoparticle. In some embodiments, mixing the one or more precursors of at least one second nanoparticle with the hollow nanoparticle comprises immersing the hollow nanoparticle in the at least one aqueous solution. In some embodiments, mixing the one or more precursors of at least one second nanoparticle with the hollow nanoparticle comprises flowing one or more aqueous solutions of one or more precursors of the at least one second nanoparticle through a membrane comprising the hollow nanoparticle. In some embodiments, flowing one or more aqueous solutions through a membrane comprises flowing one or more aqueous solutions through a membrane using vacuum filtration.

Methods of making composite particles described herein, in some embodiments, further comprise sealing the porous hollow nanoparticle. In some embodiments, sealing comprises providing a metal-containing species capable of undergoing deposition by an oxidation-reduction reaction on the surface of the porous hollow nanoparticle. In some embodiments, sealing comprises providing a metal-containing species capable of undergoing electroless deposition on the surface of the porous hollow nanoparticle.

Methods of making composite particles described herein, in some embodiments, further comprise associating one or more species to an outer surface of the composite particle. In some embodiments, one or more species are associated with an outer surface directly. In some embodiments, one or more species are associated with an outer surface indirectly. In some embodiments, one or more species are associated with an outer surface indirectly through one or more species that are associated with the outer surface directly. In some embodiments, one or more species associated with an outer surface comprises a polyethylene glycol moiety. In some embodiments, one or more species associated with an outer surface comprises a targeting agent. In some embodiments, one or more species associated with an outer surface comprises a Raman active species.

In some embodiments, a method of making a composite particle comprises providing a porous hollow nanoparticle, providing one or more therapeutic agents, and mixing the one or more therapeutic agents with the hollow nanoparticle to dispose at least one of the therapeutic agents within the hollow nanoparticle. In some embodiments, the hollow nanoparticle comprises any porous hollow nanoparticle described herein. In some embodiments, the hollow nanoparticle comprises a hollow metal nanoparticle. In some embodiments, the hollow nanoparticle comprises a hollow metallic nanoparticle. In some embodiments, the hollow nanoparticle comprises a hollow metal oxide nanoparticle. In some embodiments, the hollow nanoparticle comprises a hollow semiconductor nanoparticle.

Methods of making a composite particle described herein, in some embodiments, comprise providing and mixing one or more therapeutic agents in various forms and ways. In some embodiments, providing one or more therapeutic agents comprises providing at least one aqueous solution of the one or more therapeutic agents. In some embodiments, mixing the one or more therapeutic agents with the hollow nanoparticle comprises immersing the hollow nanoparticle in at least one aqueous solution. In some embodiments, mixing the one or more therapeutic agents with the hollow nanoparticle comprises flowing one or more aqueous solutions of one or more therapeutic agents through a membrane comprising the hollow nanoparticle. In some embodiments, flowing one or more aqueous solutions through a membrane comprises flowing one or more aqueous solutions through a membrane using vacuum filtration. In some embodiments, mixing the one or more therapeutic agents with the hollow nanoparticle comprises mixing at a temperature higher than about 25° C. In some embodiments, mixing the one or more therapeutic agents with the hollow nanoparticle comprises mixing at a temperature higher than about 37° C. In some embodiments, mixing the one or more therapeutic agents with the hollow nanoparticle comprises mixing at a temperature higher than about 40° C., higher than about 50° C., higher than about 60° C., higher than about 70° C., higher than about 80° C., or higher than about 90° C.

In some embodiments, a method of making a composite particle comprises providing a porous hollow nanoparticle, providing one or more therapeutic agents, mixing the one or more therapeutic agents with the hollow nanoparticle to dispose at least one of the therapeutic agents within the hollow nanoparticle, and sealing the porous hollow nanoparticle. In some embodiments, sealing comprises providing a metal-containing species capable of undergoing deposition through an oxidation-reduction reaction on the surface of the porous hollow nanoparticle. In some embodiments, sealing comprises providing a metal-containing species capable of undergoing electroless deposition on the surface of the porous hollow nanoparticle.

In some embodiments, a method of making a composite particle comprises providing a porous hollow nanoparticle, providing one or more therapeutic agents, mixing the one or more therapeutic agents with the hollow nanoparticle to dispose at least one of the therapeutic agents within the hollow nanoparticle, and associating one or more species with an outer surface of the composite particle. In some embodiments, at least one species associated with an outer surface comprises a polyethylene glycol moiety. In some embodiments, at least one species associated with an outer surface comprises a targeting agent. In some embodiments, at least one species associated with an outer surface comprises a Raman active species.

In some embodiments, a method of making a composite particle comprises providing a hollow nanoparticle, providing one or more Raman active species, and mixing the one or more active Raman species with the hollow nanoparticle to associate at least one of the Raman active species with an outer surface of the hollow nanoparticle. In some embodiments, the hollow nanoparticle comprises any hollow nanoparticle described herein. In some embodiments, the hollow nanoparticle comprises a hollow metal nanoparticle. In some embodiments, the hollow nanoparticle comprises a hollow metallic nanoparticle. In some embodiments, the hollow nanoparticle comprises a hollow metal oxide nanoparticle. In some embodiments, the hollow nanoparticle comprises a hollow semiconductor nanoparticle.

Methods of making a composite particle described herein, in some embodiments, comprise providing and mixing one or more Raman active species in various forms and ways. In some embodiments, providing one or more Raman active species comprises providing at least one aqueous solution of the one or more Raman active species. In some embodiments, at least one aqueous solution comprises at least one Raman active species in a concentration greater than or equal to about 1 $\mu$M. In some embodiments, at least one aqueous solution comprises at least one Raman active species in a concentration greater than or equal to about 10 $\mu$M, greater than or equal to about 100 $\mu$M, or greater than or equal to about 1000 $\mu$M. In some embodiments, at least one aqueous solution comprises at least one Raman active species in a concentration between about 1 $\mu$M and about 1 mM. In some embodiments, at least one aqueous solution comprises at least one Raman active species in a concentration between about 30 $\mu$M and about 50 $\mu$M. In some embodiments, mixing the one or more Raman active species with the hollow nanoparticle comprises immersing the hollow nanoparticle in at least one aqueous solution comprising at least one Raman active species. In some embodiments, mixing the one or more Raman active species with the hollow nanoparticle comprises immersing a membrane comprising the hollow nanoparticle in at least one aqueous solution comprising at least one Raman active species. In some embodiments, mixing the one or more Raman active species with the hollow nanoparticle comprises flowing at least one solution comprising at least one Raman active species through a membrane comprising the hollow nanoparticle. In some embodiments, flowing one or more aqueous solutions through a membrane comprises flowing one or more aqueous solutions through a membrane using vacuum filtration.

In some embodiments, a method of making a composite particle comprises providing a hollow nanoparticle, providing one or more Raman active species, mixing the one or more active Raman species with the hollow nanoparticle to associate at least one of the Raman active species to an outer surface of the hollow nanoparticle, providing one or more species comprising a polyethylene glycol moiety, and mixing the one or more species comprising a polyethylene glycol moiety to associate at least one species comprising a polyethylene glycol moiety to an outer surface of the hollow nanoparticle. In some embodiments, association with an outer surface of the hollow nanoparticle is direct association. In some embodiments, association with an outer surface of the hollow nanoparticle is indirect association. In some embodiments, the Raman active species forms a first layer and the species comprising a polyethylene glycol moiety forms a second layer, wherein the second layer substantially surrounds the first layer. In some embodiments, the method is a one-pot method. In some embodiments, the method is a one-step method.

In some embodiments, composite particles made in accordance with one or more methods described herein can have any of the properties recited herein for composite particles or hollow nanoparticles. For example, in some embodiments, a method of making a composite particle described herein comprises making a composite particle having a cavity having a size or shape as described herein. In some embodiments, a method of making a composite particle described herein comprises making a composite particle having a shell having a thickness or composition as described herein. In some embodiments, a method of making a composite particle described herein comprises making a composite particle having one or more species associated with an outer surface as described herein.

V. Methods of Imaging and Treating Biological Environments

In another aspect, methods of imaging and treating biological environments are disclosed herein. A method of imaging a biological environment described herein, in some embodiments, comprises providing a hollow nanoparticle described herein and irradiating the hollow nanoparticle with electromagnetic radiation. A method of treating a biological environment described herein, in some embodiments, comprises providing a hollow nanoparticle described herein and irradiating the hollow nanoparticle with electromagnetic radiation. In some embodiments, both imaging and treating a biological environment can be carried out at substantially the same time. In some embodiments, at least a portion of the electromagnetic radiation is inelastically scattered by the hollow nanoparticle. In some embodiments, at least a portion of the electromagnetic radiation interacts with a surface plasmon of the hollow nanoparticle. In some embodiments, irradiating induces photothermal heating. In some embodiments, irradiating induces rupturing of the hollow nanoparticle. In some embodiments, imaging a biological environment comprises imaging with surface plasmon resonance (SPR) imaging. In some embodiments, imaging a biological environment comprises imaging with surface enhanced Raman spectroscopy (SERS). In some embodiments, imaging a biological environment comprises imaging with magnetic resonance imaging (MRI). In some embodiments, imaging a biological environment comprises imaging with positron emission tomography (PET). In some embodiments, imaging a biological environment comprises imaging with a combination of two or more of SPR imaging, SERS, MRI, and PET. In some embodiments, treating a biological environment comprises treating cancer.

VI. Methods of Delivering a Payload

In another aspect, methods of delivering a payload are described herein, which, in some embodiments, may offer one or more advantages over prior methods of delivering a payload. In some embodiments, for example, a method of delivering a payload described herein is safe and efficient. In some embodiments, a method of delivering a payload comprises providing a hollow nanoparticle comprising a shell, a cavity substantially defined by the shell, and a payload within the cavity; and releasing the payload. In some embodiments, the hollow nanoparticle comprises any hollow nanoparticle described herein. In some embodiments, the hollow nanoparticle comprises a hollow metal nanoparticle. In some embodiments, the hollow nanoparticle comprises a hollow metallic nanoparticle. In some embodiments, the hollow nanoparticle comprises a hollow metal oxide nanoparticle. In some embodiments, the hollow nanoparticle comprises a hollow semiconductor nanoparticle.

Methods of delivering a payload described herein, in some embodiments, comprise releasing the payload in various ways. In some embodiments, releasing comprises rupturing the shell. In some embodiments, rupturing the shell comprises directing radiation onto the nanoparticle. In some embodiments, directing radiation comprises directing visible radiation. In some embodiments, directing radiation comprises directing near infrared (NIR) radiation. In some embodiments, releasing the payload comprises allowing the payload to diffuse out of the nanoparticle. In some embodiments, the payload comprises a gas. In some embodiments, the gas comprises $H_2$. In some embodiments, the payload comprises a therapeutic agent. In some embodiments, the payload comprises a gene.

In some embodiments of methods of delivering a payload described herein, the payload is provided within the cavity by immersing the hollow nanoparticle in a solution comprising the payload. In some embodiments, the payload is provided within the cavity by immersing a membrane comprising the hollow nanoparticle in a solution comprising the payload. In some embodiments, the payload is provided within the cavity by flowing one or more solutions comprising the payload through a membrane comprising the hollow nanoparticle. In some embodiments, the payload is provided by mixing the hollow nanoparticle with the payload under high pressure, wherein the hollow nanoparticle has a porous shell. In some embodiments, the payload is provided within the cavity at an elevated temperature. In some embodiments, the payload is provided within the cavity at a temperature higher than about 25° C., higher than about 37° C., higher than about 40° C., higher than about 50° C., higher than about 60° C., higher than about 70° C., higher than about 80° C., or higher than about 90° C.

Methods of delivering a payload described herein, in some embodiments, comprise providing any hollow nanoparticle or composite particle described herein.

VII. Methods of Selectively Depositing Hollow Nanoparticles on a Surface

In another aspect, methods of selectively depositing hollow nanoparticles on a surface are described herein, which, in some embodiments, may offer one or more advantages over prior methods. In some embodiments, for example, a method of selectively depositing hollow nanoparticles on a surface described herein is simple and efficient. In some embodiments, a method of selectively depositing hollow nanoparticles on a surface comprises providing a substrate having a plurality of domains with differing hydrophobicity, forming a plurality of gas bubbles, and forming a shell on the surface of at least one of the plurality of gas bubbles to form a hollow nanoparticle. In some embodiments, the hollow nanoparticles are selectively deposited on one or more domains having a first hydrophobicity. In some embodiments, the substrate comprises a patterned substrate.

Methods of selectively depositing hollow nanoparticles on a surface described herein, in some embodiments, comprise depositing any hollow nanoparticles described herein.

Some embodiments described herein comprise nanoparticles having cavities of various sizes. In some embodiments, cavity size can be varied by altering one or more of a number of synthetic parameters, including electrolyte composition and pH, applied potential, applied potential time profile, and nucleation substrate composition. Not intending to be bound by theory, it is believed that cavity size is affected by the size of corresponding gas bubbles. In some embodiments, the size of gas bubbles described herein can be varied by altering one or more synthetic parameters, including electrolyte composition, stability, and pH; applied potential; applied potential time profile; working electrode composition; and the hydrophobicity and surface morphology of the nucleation substrate. Again not intending to be bound by theory, it is believed that the size and size distribution of gas bubbles described herein is affected by the efficiency and extent of electrochemical gas generation. In some embodiments, altering one or more of the foregoing synthetic parameters alters the efficiency of electrochemical gas generation. In some embodiments, altering one or more of the foregoing synthetic parameters alters the exchange current density.

Some embodiments described herein comprise hollow nanoparticles and composite particles having various sizes. In some embodiments, hollow nanoparticle or composite particle size can be varied by altering one or more of a number of synthetic parameters, including electrolyte composition and pH, applied potential, applied potential time profile, nucleation substrate composition, and reaction time. Not intending to be bound by theory, it is believed that hollow nanoparticle or composite particle size is affected by the size of corresponding gas bubbles. Therefore, in some embodiments, hollow nanoparticle or composite particle size can be controlled by altering synthetic parameters affecting the nucleation of gas bubbles on a substrate. In some embodiments, hollow nanoparticle or composite particle size is affected by shell thickness. Therefore, in some embodiments, hollow nanoparticle or composite particle size can be controlled by altering the shell thickness.

Some embodiments described herein comprise shells having various thicknesses. In some embodiments, shell thickness can be varied by altering a number of synthetic parameters, including electrolyte composition and pH, applied potential, applied potential time profile, and reaction time.

Some embodiments described herein comprise hollow nanoparticles or composite particles exhibiting various surface plasmon resonance peaks. In some embodiments, SPR peak wavelength can be varied by altering one or more of a number of parameters, including hollow nanoparticle or composite particle composition, surface roughness, and shell thickness.

Some embodiments described herein comprise shells, hollow nanoparticles, or composite particles having various surface roughnesses. In some embodiments, surface roughness can be varied by altering one or more of electrolyte composition and pH, reaction time, applied potential, and applied potential time profile.

Some embodiments described herein comprise shells having various compositions. In some embodiments, shell composition can be varied by altering the electrolyte composition. In some embodiments, the electrolyte composition can be altered by changing the identity of one or more metal-containing species. Not intending to be bound by theory, in some embodiments, shells having various compositions can be provided by using electrolytes comprising one or more metal-containing species, wherein at least one metal-containing species can be reduced or oxidized by at least one electrochemically generated gas. Again not intending to be bound by theory, in some embodiments, shells having various compositions can be provided by using electrolytes comprising one or more metal-containing species, wherein at least one metal-containing species is operable to undergo deposition through an oxidation-reduction reaction. In some embodiments, at least one metal-containing species is operable to undergo electroless deposition. In some embodiments, a plurality of metal-containing species have substantially similar reduction potentials. In some embodiments, shells having various compositions can be provided by using electrolytes comprising one or more metal-containing species, wherein at least one metal-containing species is operable to undergo deposition through an oxidation-reduction reaction on the surface of a gas bubble. In some embodiments, shells having various compositions can be provided by using electrolytes comprising one or more metal-containing species, wherein at least one metal-containing species is operable to undergo electroless deposition on the surface of a gas bubble. In some embodiments, shells having various compositions can be provided by using electrolytes comprising one or more metal-containing species, wherein at least one metal-containing species is operable to undergo deposition through oxidation-reduction on the surface of a metal shell. In some embodiments, shells having various compositions can be provided by using electrolytes comprising one or more metal-containing species, wherein at least one metal-containing species is operable to undergo electroless deposition on the surface of a metal shell.

Some embodiments described herein comprise pores of various sizes. In some embodiments, pore size can be controlled by altering one or more of reaction time, electrolyte composition and pH, applied potential, and applied potential time profile. In some embodiments, altering the electrolyte composition comprises altering the concentration of a metal-containing species in the electrolyte. In some embodiments, altering the electrolyte composition comprises altering the concentration of a reducing agent in the electrolyte.

Some embodiments described herein comprise forming at least one second nanoparticle within a porous shell, wherein the at least one second nanoparticle has various sizes. In some embodiments, the size of the at least one second nanoparticle can be controlled by altering one or more of the reaction time, the concentration of one or more precursors of the at least one second nanoparticle, the pore size, and the cavity size.

Some embodiments described herein comprise a therapeutic agent. Any suitable therapeutic agent not incompatible with the objectives of the present invention may be used. In some embodiments, the therapeutic agent comprises a gas. In some embodiments, the therapeutic agent comprises a liquid. In some embodiments, the therapeutic agent comprises a solution. In some embodiments, the therapeutic agent comprises a drug. In some embodiments, the therapeutic agent comprises a water-soluble drug. Non-limiting examples of therapeutic agents useful in some embodiments include mitoxantrone and gemcitabine. Suitable therapeutic agents may be purchased from commercial sources or prepared according to methods known in the art.

Some embodiments described herein comprise a targeting agent. Any suitable targeting agent not incompatible with the objectives of the present invention may be used. In some embodiments, the targeting agent comprises a species operable to selectively interact with an analyte or biomarker. In some embodiments, the targeting agent comprises a species operable to selectively interact with an antigen. In some embodiments, the targeting agent comprises one or more of proteins (including naturally occurring proteins or engineered proteins), antibodies, antibody fragments, peptides, and small molecules. In some embodiments, the targeting agent comprises a protein. In some embodiments, the targeting agent comprises an antibody. In some embodiments, the targeting agent comprises a peptide. In some embodiments, the targeting agent comprises a small molecule. The targeting agent can also be a minibody, diabody, triabody, tetrabody, aptamer, affibody, or peptoid. Specific non-limiting examples of targeting agents useful in some embodiments include streptavidin, biotin, anti-PSMA, $NH_2GR_{11}$, and c(RGDyK). Suitable species may be purchased from commercial sources or prepared according to methods known in the art.

Some embodiments described herein comprise a Raman active species. Any suitable Raman active species not incompatible with the objectives of the present invention may be used. In some embodiments, the Raman active species comprises a positive charge. In some embodiments, the Raman active species comprises a delocalized $\pi$ system. In some embodiments, the Raman active species comprises a thiol moiety. In some embodiments, the Raman active species comprises a thiol moiety operative to form a sulfur-metal bond with a surface. Non-limiting examples of Raman active species useful in some embodiments include cresyl violet, nile blue, rhodamine 6G, tetrafluoroborate, diethyl-thiatricarbocyanine (DTTC), DTTC iodide, crystal violet, IR140 (meso-diphenylamine substituted heptamethine), HITC iodide (1,1',3,3,3',3'-hexamethylindotrycarbocyanine iodide), and DOTC iodide (3-ethyl-2-[7-(3-ethyl-2(3H)-benzoxazolylidene)-1,3,5-heptatrienyl]-benzoxazolium iodide). Suitable species may be purchased from commercial sources or prepared according to methods known in the art. In some embodiments comprising a Raman active species, the dynamic range of hollow nanoparticle detection is up to about 30 dB. In some embodiments, the dynamic range of hollow nanoparticle detection is about 10 pM to about 10 nM.

Some embodiments described herein comprise a species comprising a polyethylene glycol (PEG) moiety. Any suitable species comprising a polyethylene glycol moiety not incompatible with the objectives of the present invention may be used. In some embodiments, a species comprises a monofunctional methyl ether PEG (mPEG) moiety. In some embodiments, a species comprises a thiolated polyethylene glycol moiety. In some embodiments, a species comprises a polyethylene glycol moiety and a carboxylic acid moiety. In some embodiments, a species comprises a thiolated polyethylene glycol moiety and a carboxylic acid moiety. In some embodiments, a species comprises an oligomeric or polymeric species comprising a polyethylene glycol moiety and having two ends, wherein one end comprises a thiol moiety and the other end comprises a carboxylic acid moiety. In some embodiments, a species has the formula $HS-(OCH_2CH_2)_n-COOH$. Suitable species may be purchased from commercial sources or prepared according to methods known in the art.

Some embodiments described herein comprise associating one or more species with an outer surface. Any suitable method of associating not incompatible with the objectives of the present invention may be used. In some embodiments, associating comprises forming one or more covalent bonds between an outer surface and one or more species associated with the outer surface. In some embodiments, associating comprises forming one or more metal-sulfur bonds. In some embodiments, associating comprises forming one or more Au—S bonds. In some embodiments, associating comprises forming one or more non-covalent bonds between an outer surface and one or more species associated with the outer surface. In some embodiments, forming one or more non-covalent bonds comprises forming one or more hydrogen bonds. In some embodiments, associating comprises forming one or more ionic bonds. In some embodiments, associating comprises forming one or more electrostatic interactions between an outer surface and one or more species associated with the outer surface. In some embodiments, associating comprises forming one or more hydrophobic interactions between an outer surface and one or more species associated with the outer surface. In some embodiments, associating comprises forming one or more van der Waals interactions.

In some embodiments, associating comprises forming one or more direct associations (such as covalent bonds, non-covalent bonds, hydrogen bonds, ionic bonds, electrostatic interactions, or van der Waals interactions) between an outer surface and one or more first species directly associated with the outer surface and further forming one or more associations between at least one first species and at least one second species not directly associated with the outer surface. In some embodiments, the first species and the second species are associated by one or more covalent bonds, non-covalent bonds, hydrogen bonds, ionic bonds, electrostatic interactions, or van der Waals interactions. In some embodiments, the first species and the second species are associated through covalent coupling chemistry. In some embodiments, the first species and the second species are associated through carbodiimide chemistry. In some embodiments, the first species and the second species are associated through click chemistry. In some embodiments, the first species forms a first layer substantially surrounding the outer surface and the second species forms a second layer substantially surrounding the first layer.

Some embodiments described herein comprise electrochemically generated gas bubbles. In some embodiments, an electrochemically generated gas bubble comprises a gas bubble comprising one or more species formed at the surface of an electrode. In some embodiments, an electrochemically generated gas bubble comprises a gas bubble comprising one or more species formed from an oxidation or reduction reaction occurring at the surface of an electrode.

Some embodiments described herein comprise an electrolyte. Any suitable electrolyte not incompatible with the objectives of the present invention may be used. In some embodiments, the electrolyte comprises an electrolyte operable for the electrodeposition of one or more metals. In some embodiments, the electrolyte comprises an electrolyte operable for the deposition of one or more metals through one or more oxidation-reduction reactions. In some embodiments, the electrolyte comprises an electrolyte operable for the electroless deposition of one or more metals. In some embodiments, the electrolyte comprises a commercial electrolyte. In some embodiments, the electrolyte comprises a modified commercial electrolyte.

Some embodiments described herein comprise an electrolyte comprising a promoter. In some embodiments, a promoter is operable to promote the efficient generation of gas bubbles. In some embodiments, a promoter is operable to promote efficient electrochemical generation of a gas. In some embodiments, a promoter is operable to promote efficient electrochemical generation of hydrogen. In some embodiments, a promoter is operable to promote nucleation of substantially spherical gas bubbles. In some embodiments, a promoter is operable to alter the hydrophobicity of a nucleation substrate. In some embodiments, a promoter is operable to decrease the hydrophobicity of a nucleation substrate. In some embodiments, a promoter is operable to increase the hydrophobicity of a nucleation substrate. In some embodiments, a promoter is operable to increase the hydrophobicity of a substrate comprising alumina. In some embodiments, a promoter is operable to stabilize a metal-containing species. In some embodiments, a promoter is operable to suppress disproportionation of a metal-containing species. In some embodiments, a promoter is operable to remove contaminants from an electrode surface. In some embodiments, a promoter is operable to remove oxide from an electrode surface. In some embodiments, a promoter is operable to undergo electrodeposition onto an electrode surface. In some embodiments, a promoter is operable to increase the exchange current density of the electrode. In some embodiments, a promoter is operable to increase the hydrogen exchange current density of the electrode. In some embodiments, a promoter is operable to increase the current density of gas evolution by about 50% to about 400%. In some embodiments, a promoter is operable to increase the current density of gas evolution by about 100% to about 300%. In some embodiments, a promoter comprises at least one lone pair of electrons capable of binding to a metal. In some embodiments, a promoter comprises at least one lone pair of electrons capable of binding to oxygen. In some embodiments, a promoter comprises a polydentate species. In some embodiments, a promoter comprises a bidentate species. In some embodiments, a promoter comprises a source of one or more solution phase ions that is the same as one or more ions contained in a metal-containing species.

Some embodiments described herein comprise a nucleation substrate. Any suitable nucleation substrate not incompatible with the objectives of the present invention may be used. In some embodiments, a nucleation substrate comprises a surface operable to support the nucleation of one or more gas bubbles. In some embodiments, a nucleation substrate comprises a surface operable to support the nucleation and growth of one or more nanoparticles. In some embodiments, a nucleation substrate comprises a plurality of channels. In some embodiments, a nucleation substrate comprises at least one crack, hole, ridge, or defect. In some embodiments, a nucleation substrate comprises a rough surface. In some embodiments, a nucleation substrate comprises a plurality of domains. In some embodiments, the domains are separated by boundaries or junctions. In some embodiments, one or more domains exhibit different properties. In some embodiments, one or more domains exhibit differing hydrophobicity. In some embodiments, one or more domains exhibit different surface treatment. In some embodiments, a nucleation substrate comprises Ag. In some embodiments, a nucleation substrate comprises Si. In some embodiments, a nucleation substrate comprises $SiO_2$. In some embodiments, a nucleation substrate comprises $TiO_2$. In some embodiments, a nucleation substrate comprises $Al_2O_3$. In some embodiments, a nucleation substrate comprises Cu. In some embodiments, a nucleation substrate comprises C. In some embodiments, a nucleation substrate comprises a patterned substrate. In some embodiments, a nucleation substrate comprises a patterned glass substrate. In some embodiments, a nucleation substrate comprises a $SiO_2$ substrate comprising at least one Ag stripe. In some embodiments, a nucleation substrate operates as a working electrode. In some embodiments, a nucleation substrate comprises a membrane. In some embodiments, the membrane comprises anodic aluminum oxide.

VIII. Radioactive Nanoparticles

In another aspect, radioactive nanoparticles are described herein. In some embodiments, a radioactive nanoparticle described herein comprises a metal nanoparticle core and an outer metal shell disposed over the metal nanoparticle core. Further, at least one metallic radioisotope is disposed within the metal nanoparticle core and/or or within the outer metal shell. In addition, in some cases, a radioactive nanoparticle described herein further comprises an inner metal shell disposed between the metal nanoparticle core and the outer metal shell.

Turning now to specific components of radioactive nanoparticles, a radioactive nanoparticle described herein comprises a metal nanoparticle core. Any metal nanoparticle core not inconsistent with the objectives of the present disclosure may be used. In some cases, for instance, the metal nanoparticle core comprises a hollow metal nanoparticle described hereinabove in Section I or a composite particle described hereinabove in Section III. In other embodiments, the metal nanoparticle core comprises a solid metal nanoparticle, such as a solid nanoparticle comprising or formed from a transition metal or "d block" metal such as Fe, Co, Rh, Ir, Ni, Pd, Pt, Cu, Ag, or Au, or from a mixture or alloy of two or more of the foregoing metallic elements. In some instances, a metal nanoparticle core comprises or is formed from a lanthanide metal such as Sm. Further, in some cases, the metal nanoparticle core of a radioactive nanoparticle described herein can be formed from one or more metals in an elemental state or "zero" oxidation state, as opposed to being formed from a species in which the metal is in an oxidized state, such as may occur in a metal oxide.

The metal nanoparticle core of a radioactive nanoparticle described herein can also have any size, shape, and structure not inconsistent with the objectives of the present disclosure. For example, in some instances, the metal nanoparticle core of a radioactive nanoparticle described herein is spherical or substantially spherical. In other embodiments, the metal nanoparticle core is oblate. A metal nanoparticle core may also have a polyhedral or faceted shape or an irregular shape. Moreover, in some embodiments, a metal nanoparticle core can itself have a core-shell structure or other complex architecture. For instance, in some implementations, the metal nanoparticle core of a radioactive nanoparticle described herein is a nanorod having a core-shell structure. Further, such a core-shell structure can be an alternating core-shell structure, such as exhibited by a nanorod consisting of a Au nanorod core (e.g., having a diameter of 10-30 nm) surrounded by a first Co shell (e.g., having a thickness of 5-10 nm), a second Au shell (e.g., having a thickness of 10-20 nm), a third Co shell (e.g., having a thickness of 5-10 nm), and a fourth Au shell (e.g., having a thickness of 10-20 nm). Other complex metal nanoparticle cores may also be used. Additionally, in some cases, the metal nanoparticle core of a radioactive nanoparticle described herein has a total size of about 30-500 nm in two dimensions or three dimensions. In some embodiments, the metal nanoparticle core has a size of about 30-400 nm, 30-300 nm, 50-500 nm, 50-400 nm, 50-300 nm, 50-250 nm, 50-200, nm, 50-150 nm, 80-500 nm, 80-300 nm, 80-200 nm, 100-500 nm, 100-400 nm, 100-300 nm, 100-200 nm, 120-450 nm, 120-300 nm, 120-200 nm, or 120-180 nm in each of two or three dimensions.

Radioactive nanoparticles described herein also comprise an outer metal shell. The outer metal shell can comprise or be formed from any metal or combination of metals not inconsistent with the objectives of the present disclosure. In some instances, the outer metal shell comprises or is formed from a transition metal, including one or more of Fe, Co, Rh, Ir, Ni, Pd, Pt, Cu, Ag, and Au. In some embodiments, the outer metal shell comprises or is formed from a lanthanide metal, such as Sm. Additionally, in some cases, the outer metal shell is formed from a mixture or alloy of two or more of the foregoing metals. Further, the metal or combination of metals forming the outer metal shell can be in an elemental state. Moreover, as described further hereinbelow, the outer metal shell of a radioactive nanoparticle described herein can comprise or be formed from the same metal (or combination of metals) or from a different metal (or combination of metals) than the metal nanoparticle core. Thus, in some embodiments, the metal nanoparticle core and the outer metal shell are formed from the same metal or combination of metals, while in other instances the metal nanoparticle core and the outer metal shell are formed from differing metals or combinations of metals. Further, in some cases, the metal nanoparticle core is formed from a metal having a higher reduction potential than a metal of the outer metal shell. For example, in some embodiments, the metal nanoparticle core is formed from Au and the outer metal shell is formed from Pd. Alternatively, it is also possible for the metal of the metal nanoparticle core to have a lower reduction potential than the metal of the outer metal shell.

Moreover, the outer metal shell of a radioactive nanoparticle described herein can have any thickness not inconsistent with the objectives of the present disclosure. In some instances, for example, the outer metal shell has an average thickness of about 1-50 nm, 1-20 nm, 1-10 nm, 1-5 nm, 5-50 nm, 5-20 nm, 5-20 nm, 5-10 nm, or 10-50 nm. Other thicknesses are also possible. In addition, the outer metal shell of a radioactive nanoparticle described herein can be a complete metal shell or a substantially complete metal shell, where a "substantially" complete metal shell covers at least about 80%, at least about 85%, at least about 90%, at least about 95%, or at least about 98% of the exterior surface of the underlying metal nanoparticle core. Alternatively, in other instances, the outer metal shell is not a complete or substantially complete metal shell. Further, the outer metal shell of a radioactive nanoparticle described herein can be porous or non-porous.

A radioactive nanoparticle described herein, in some embodiments, also comprises an inner metal shell disposed between the metal nanoparticle core and the outer metal shell. The inner metal shell can be formed from any metal or combination of metals not inconsistent with the objectives of the present disclosure. For example, in some instances, the inner metal shell comprises or is formed from a transition metal, including one or more of Fe, Co, Rh, Ir, Ni, Pd, Pt, Cu, Ag, and Au. In some embodiments, the inner metal shell comprises or is formed from a lanthanide metal, such as Sm. Further, the metal or combination of metals forming the inner metal shell can be in an elemental state.

Moreover, in some cases, the inner metal shell comprises or is formed from a metal or combination of metals that is capable of forming a metallic shell on the surface of the metal nanoparticle core by electroless metal deposition or plating, as described further hereinbelow in Section IX. In addition, in some such cases, the inner metal shell also comprises or is formed from a metal having a lower reduction potential than a metal of the outer metal shell of the radioactive nanoparticle. As described further hereinbelow in Section IX, an inner metal shell formed from such a metal or combination of metals can be at least partially replaced by the outer metal shell during formation of the radioactive nanoparticle. For example, in some instances, the inner metal shell undergoes a galvanic replacement reaction with an ionized metal of the outer metal shell. In one non-limiting example of a radioactive nanoparticle described herein, the metal nanoparticle core is formed from Au, the inner metal shell is formed from Cu, and the outer metal shell is formed from Pd, Rh, Au, or a combination thereof. Other combinations of metals are also possible.

Further, the inner metal shell of a radioactive nanoparticle described herein, when present, can have any thickness not inconsistent with the objectives of the present disclosure. In some instances, the inner metal shell has an average thickness of less than about 10 nm, less than about 5 nm, less than about 3 nm, or less than about 1 nm. Other thicknesses are also possible.

A radioactive nanoparticle described herein also comprises a metallic radioisotope. Any metallic radioisotope not inconsistent with the objectives of the present disclosure may be used. Moreover, as understood by one of ordinary skill in the art, a metallic radioisotope can be an isotope of a metal that is radioactive or has an unstable nucleus, such as an isotope that has a half-life of less than $10^{22}$ years. In addition, the metallic radioisotope of a radioactive nanoparticle described herein can comprise or be formed from any metallic element not inconsistent with the objectives of the present disclosure. In some cases, for instance, the metallic radioisotope comprises a radioactive isotope of a transition metal such as yttrium (Y), rhenium (Re), Fe, Co, rhodium (Rh), iridium (Ir), Ni, Pd, Pt, Cu, Ag, and Au. The metallic radioisotope may also comprise a radioactive isotope of a lanthanide metal or an actinide metal. Non-limiting examples of metallic radioisotopes that may be used in some embodiments described herein include Cu-64, Cu-67, Y-90, Pd-103, Rh-105, Re-186, Re-188, Ir-192, and Au-198. Other radioisotopes may also be used. In some embodiments, the metallic radioisotope of a radioactive nanoparticle described herein can be selected to provide a desired type of radioactive decay. For example, in some cases, the metallic radioisotope is a β-emitter. Additionally, in some implementations, the metallic radioisotope can be selected based on its half-life. For instance, in some cases, the metallic radioisotope is selected to have a relatively short half-life, such as a half-life of 72 hours or less. Alternatively, in other embodiments, the metallic radioisotope is selected to have a relatively long half-life, such as a half-life of 10 days or more. Further, in some instances, a radioactive nanoparticle described herein includes a plurality of differing metallic radioisotopes. In some such cases, the differing metallic radioisotopes can be combined to provide both a relatively rapid decay profile and a relatively slow decay profile. For example, in some instances, a first metallic radioisotope can comprise Y-90 (having a half-life of 64 h), and a second metallic radioisotope can comprise Pd-103 (having a half-life of 17 days). More generally, the second metallic radioisotope of such a radioactive nanoparticle can have a half-life that is at least about 5 times, at least about 10 times, or at least about 20 times longer than the half-life of the first metallic radioisotope. A radioactive nanoparticle comprising a combination of differing metallic radioisotopes such as described above, in some instances, can be especially useful for providing both low dose rate (LDR) and high dose rate (HDR) treatment to a biological compartment, as described further hereinbelow. Moreover, in some cases, such a radioactive nanoparticle can also provide synergistic effects.

It is further to be understood that, in some instances, a second metallic radioisotope or other additional radioisotope can be included in a radioactive nanoparticle described herein not as part of the outer shell of the radioactive nanoparticle, but instead as part of a radiolabeled organic ligand or chelate complex. Such a ligand or chelate complex can include a first moiety for attachment to or association with an exterior surface of the radioactive nanoparticle (including in a manner described hereinabove in Section VII for association with an outer surface), and a second moiety for chelating or binding a metallic radioisotope. For example, in some embodiments, a ligand or chelate complex can comprise a thiolated 1,4,7,10-tetraazacyclododecane-1,4,7,10-tetraacetic acid (DOTA). In such an instance, the thiol moiety or moieties of the thiolated DOTA can bond or attach to a surface of the radioactive nanoparticle (such as an exterior surface of the outer shell), and the tetraacetic acid moiety can chelate a metallic radioisotope (such as Y-90). Other such ligands or complexes may also be used to provide an additional radioisotope to a radioactive nanoparticle described herein.

Moreover, in some embodiments, the chemical identity of a metallic radioisotope of a radioactive nanoparticle described herein is selected based on the chemical composition and/or reduction potential of one or more other components of the radioactive nanoparticle, such as one or more of the metal nanoparticle core, the inner metal shell, and the outer metal shell. For example, in some cases wherein the metallic radioisotope is disposed within the outer metal shell, the metallic radioisotope comprises a metal that has a higher reduction potential than a metal of the inner metal and/or that is the same as a metal of the outer metal shell. Alternatively, in other instances, the metallic radioisotope and the outer metal shell are formed from differing metallic elements.

Further, the metallic radioisotope of a radioactive nanoparticle described herein can be in an elemental state, as opposed to being in an ionic state. Thus, the metallic radioisotope can be integrated with the metal of the outer metal shell, as opposed to being present only at the surface of the outer metal shell, or opposed to being present as part of a radiolabeled or radioactive organometallic compound or molecular metal complex. In addition, the metallic radioisotope can be present in the outer metal shell in an amount not inconsistent with the objectives of the present disclosure. In some cases, for instance, the radioactive metallic isotope is present in the outer shell in an amount of 0.001-10 ppb, 0.001-1 ppb, 0.01-10 ppb, 0.01-1 ppb, 0.1-10 ppb, or 0.1-1 ppb. The radioactive isotope may also be present in the outer shell in an amount greater than 10 ppb. For instance, in some cases, the radioactive metallic isotope is present in the outer shell in an amount of 100-1000 ppb, 1-1000 ppm, 1-100 ppm, 1-10 ppm, 10-1000 ppm, 10-100 ppm, or 100-1000 ppm. Other amounts are also possible.

A radioactive nanoparticle described herein can have any overall size and shape not inconsistent with the objectives of the present disclosure. In some cases, for instance, a radioactive nanoparticle described herein is spherical or substantially spherical. In other instances, the radioactive nanoparticle is oblate. A radioactive nanoparticle may also have a polyhedral or faceted shape or an irregular shape. Further, in some embodiments, a radioactive nanoparticle described herein has a size of about 30-500 nm in three dimensions. In some instances, the radioactive nanoparticle has a size of 30-400 nm, 30-300 nm, 50-500 nm, 50-400 nm, 50-300 nm, 50-250 nm, 50-200, nm, 50-150 nm, 80-500 nm, 80-300 nm, 80-200 nm, 100-500 nm, 100-400 nm, 100-300 nm, 100-200 nm, 120-450 nm, 120-300 nm, 120-200 nm, or 120-180 nm in each of two or three dimensions. Moreover, it is to be understood that the size of the radioactive nanoparticle in a specific dimension, in some cases, does not include any size contribution that may be provided by an organic or inorganic ligand shell, biomolecule, or other species that may be present on or associated with the exterior surface of the radioactive nanoparticle. In other instances, the size of a radioactive nanoparticle described herein is a hydrodynamic size, including a hydrodynamic size in aqueous solution, buffer, and/or serum. Moreover, it is to be understood that the "size" of a radioactive nanoparticle in a specific direction is the maximum length or diameter of the radioactive nanoparticle in that direction. Not intending to be bound by theory, it is believed that radioactive nanoparticles having a size described herein, in some cases, can be retained within a biological compartment such as a tumor for therapeutically effective time periods.

Additionally, in some embodiments, a radioactive nanoparticle described herein can be present in a composition, including a composition that comprises a plurality or population of dispersed radioactive nanoparticles described herein. Such a composition, for instance, may be a colloid or a solution of the radioactive nanoparticles. In such embodiments, the plurality or population of radioactive nanoparticles can exhibit a narrow size distribution. Further, in some cases, the size distribution of the plurality of radioactive nanoparticles is the same or substantially the same as the size distribution of the metal nanoparticle cores used to form the radioactive nanoparticles. For example, in some instances, a population of radioactive nanoparticles described herein exhibits a monomodal size distribution with a standard deviation not greater than about 20%, not greater than about 15%, not greater than about 10%, or not greater than about 5%, where the standard deviation is based on the mean size. Further, it is to be understood that a size distribution described herein can be a size distribution measured in one, two, or three dimensions.

Moreover, in some embodiments, a radioactive nanoparticle described herein can have a negative surface charge, including a negative exterior surface charge. A radioactive nanoparticle described herein may also have a positive surface charge, including a positive exterior surface charge. In some cases, for instance, the radioactive nanoparticle has a zeta potential of at least ±5 mV, at least AO mV, at least ±20 mV, or at least ±25 mV. In some instances, a radioactive nanoparticle described herein has a zeta potential between about ±5 mV and about ±100 mV, between about ±5 mV and about ±50 mV, between about ±10 mV and about ±100 mV, between about ±10 mV and about ±50 mV, between about ±10 mV and about ±30 mV, or between about ±15 mV and about ±35 mV.

Not intending to be bound by theory, it is believed that a radioactive nanoparticle having a negative surface charge described herein can exhibit improved stability in solution and/or a long "shelf life," where stability in "solution" can include stability in a colloid as well as a solution of the radioactive nanoparticles. For instance, in some cases, a solution or colloid of radioactive nanoparticles described herein can exhibit no flocculation or substantially no flocculation for up to 90 days, up to 60 days, or up to 30 days, where "substantially no flocculation" refers to less than 10 weight %, less than 5 weight %, or less than 1 weight % flocculation, based on the total weight of the radioactive nanoparticles present in the solution or colloid. In some cases, a solution or colloid of radioactive nanoparticles described herein exhibits no flocculation or substantially no flocculation for 15-90 days, 15-45 days, 30-90 days, 30-45 days, or 30-60 days. Moreover, it is further to be noted that a solution or colloid of radioactive nanoparticles described herein that does flocculate can generally be redispersed prior to use in a manner described herein.

Radioactive nanoparticles described herein can also have any radioactivity not inconsistent with the objectives of the present disclosure. In some cases, for instance, a single radioactive nanoparticle can have a radioactivity of about 0.4 to 400 Bq or about 4 to 40 Bq. In some instances, a solution or colloid of the radioactive nanoparticles has a radioactivity of about 37 to 3700 MBq, 37 to 370 MBq, or 37 to 185 MBq. Other radioactivity levels are also possible.

IX. Methods of Making a Radioactive Nanoparticle

In another aspect, methods of making a radioactive nanoparticle are described herein. A method of making a radioactive nanoparticle described herein, in some embodiments, comprises providing a metal nanoparticle core and forming an inner metal shell over the metal nanoparticle core, the inner metal shell comprising a first metal or combination of metals. Moreover, the method further comprises forming an outer metal shell over the metal nanoparticle core, the outer metal shell comprising a second metal or combination of metals including at least one metallic radioisotope. In some instances, the second metal or combination of metals further comprises a non-radioactive metallic isotope.

Turning now to specific steps of methods described herein, a method of making a radioactive nanoparticle described herein comprises providing a metal nanoparticle core. The metal nanoparticle core can be provided in any manner not inconsistent with the objectives of the present disclosure. In some embodiments, for instance, providing the metal nanoparticle core comprises making a hollow metal nanoparticle in a manner described hereinabove in Section II or making a composite particle in a manner described hereinabove in Section IV. In other cases, providing the metal nanoparticle core comprises providing a metal nanoparticle core having a size, shape, and/or chemical composition described hereinabove in Section VIII. For example, in some instances, providing a metal nanoparticle core comprises providing a solid nanoparticle formed from a transition metal such as Fe, Co, Rh, Ir, Ni, Pd, Pt, Cu, Ag, or Au, or from a mixture or alloy of two or more of the foregoing metallic elements. Moreover, in some cases, providing a metal nanoparticle core comprises providing a solution, colloid, or other composition comprising a plurality of metal nanoparticle cores.

Methods described herein also comprise forming an inner metal shell over the metal nanoparticle core. The inner metal shell can be formed over the metal nanoparticle core in any manner not inconsistent with the objectives of the present disclosure. In some cases, the inner metal shell is formed through electroless deposition or plating of the first metal or combination of metals onto an exterior surface of the metal nanoparticle core. As understood by one of ordinary skill in the art, such electroless deposition or plating of the first metal or combination of metals can be an auto-catalytic redox reaction between the first metal or combination of metals and the exterior surface of the metal nanoparticle core. The first metal or combination of metals can thus comprise any metal or combination of metals capable of undergoing electroless deposition on the surface of the metal nanoparticle core. Thus, in some embodiments, forming the inner metal shell comprises adding a solution of the first metal or combination of metals to the metal nanoparticle core, wherein the first metal or combination of metals is in a non-zero or positive oxidation state. In some such instances, the first metal or combination of metals is provided as one or more metal salts, organometallic compounds, or metal complexes.

Additionally, in some cases, the first metal or combination of metals comprises a metal described hereinabove in Section VIII for the inner shell of a radioactive nanoparticle. For instance, in some embodiments, the first metal or combination of metals comprises a transition metal or a lanthanide metal, including one or more of Fe, Co, Rh, Ir, Ni, Pd, Pt, Cu, Ag, Au, and Sm. Moreover, as described above, the inner metal shell can comprise or be formed from the same metal (or combination of metals) or a different metal (or combination of metals) than the metal nanoparticle core.

Methods described herein also comprise forming an outer metal shell over the metal nanoparticle core. The outer metal shell can be formed in any manner not inconsistent with the objectives of the present disclosure. For example, as with the formation of the inner metal shell, the outer metal shell of a radioactive nanoparticle described herein can be formed by mixing a solution of the second metal or combination of metals with the metal nanoparticle core after the inner metal shell has been formed. Any solution of the second metal or combination of metals may be used. For instance, in some cases, the solution comprises salts or other complexes of the second metal or combination of metals in a positive or non-zero oxidation state.

Moreover, in some cases, the outer metal shell is formed through galvanic replacement of at least a portion of the inner metal shell with the second metal or combination of metals. In some such cases, forming the outer metal shell comprises carrying out a series or sequence of galvanic replacement reactions. For example, in some instances, a first galvanic replacement reaction is carried out between the inner metal shell and the metallic radioisotope, and a second galvanic replacement reaction is subsequently carried out between the inner metal shell and a non-radioactive metallic isotope. Performing such a sequence of galvanic replacement reactions, in some embodiments, can permit a radioisotope to be incorporated into the outer metal shell of the radioactive nanoparticle with the use of a relatively small amount of metallic radioisotope. Thus, in some cases, the amount of the metallic radioisotope is small compared to the amount of non-radioactive metallic isotope used to form the outer shell. For instance, in some cases, the molar ratio of non-radioactive metallic isotope to radioactive metallic isotope is greater than 10:1, greater than 100:1, greater than 1000:1, greater than 10,000:1, or greater than 100,000:1. In some instances, the ratio of non-radioactive to radioactive metallic isotopes is between 10:1 and 100,000:1, between 100:1 and 100,000:1, between 1000:1 and 100,000:1, between 1000:1 and 10,000:1, or between 10,000:1 and 100,000:1. Moreover, in some embodiments, the radioactive metallic isotope is used at a concentration of about $10^{-7}$ mol/L to about $10^{-9}$ mol/L.

Moreover, the metallic radioisotope and the non-radioactive metallic isotope of the second metal or combination of metals can be isotopes of the same metal or different metals. For example, in some cases, the metallic radioisotope comprises Pd-103, and the non-radioactive metallic isotope comprises a non-radioactive isotope of Pd, such as Pd-106. In other instances, the metallic radioisotope comprises Pd-103, and the non-radioactive metallic isotope comprises a non-radioactive isotope of Au, such as Au-197. Further, the metallic radioisotope can be any metallic radioisotope described hereinabove in Section VIII. Moreover, in some cases, the chemical identity of the metallic radioisotope is selected based on the chemical composition and/or reduction potential of one or more other components of the radioactive nanoparticle, such as one or more of the metal nanoparticle core, the inner metal shell, and the outer metal shell. For example, in some instances, the metallic radioisotope comprises a metal that has a higher reduction potential than a metal of the inner metal shell. Non-limiting examples of metallic radioisotopes that may be used in some embodiments described herein include Cu-64, Cu-67, Pd-103, Rh-105, Ir-192, and Au-198. Other radioisotopes may also be used.

More generally, the second metal or combination of metals can comprise any metal not inconsistent with the objectives of the present disclosure. In some cases, the second metal or combination of metals comprises one or more metals having a higher reduction potential than the first metal or combination of metals forming the inner metal shell. In some embodiments, the second metal or combination of metals comprises a transition metal, including one or more of Fe, Co, Rh, Ir, Ni, Pd, Pt, Cu, Ag, and Au. In some embodiments, the second metal or combination of metals a lanthanide metal, such as Sm. Other metals may also be used.

Further, as described above in Section VIII, the metals or combinations of metals used to form the metal nanoparticle core, the inner metal shell, and the outer metal shell according to a method described herein can generally be selected based on their relative reactivities or reduction potentials, including in such a manner as to promote facile and/or efficient electroless deposition and/or galvanic replacement reactions as described above. For instance, in some embodiments, the metal nanoparticle core is formed from Au, the first metal or combination of metals comprises Cu, and the second metal or combination of metals comprises a radioisotope of Pd, Rh, or Au and a non-radioactive isotope of Pd, Rh, or Au. Other combinations of metals are also possible without departing from the teachings of the present disclosure, as understood by one of ordinary skill in the art.

In addition, in some instances described herein, the outer metal shell completely or substantially completely replaces the inner metal shell during formation of the radioactive nanoparticle. For reference purposes herein, an outer metal shell that "substantially completely" replaces the inner metal shell replaces at least about 90 mol. %, at least about 95 mol. %, at least about 98 mol. %, or at least about 99 mol. % of the inner metal shell, based on the total amount of the inner metal shell present prior to the replacement step. In such embodiments, the inner metal shell can be absent or substantially completely absent from the final radioactive nanoparticle. In other cases, however, some amount of the inner metal shell may remain and be detectable within the completed radioactive nanoparticle.

As described herein, methods of making a radioactive nanoparticle according to the present disclosure can be carried out in a facile and/or efficient manner. Further, in some cases, a method of making a radioactive nanoparticle described herein can be carried out without applying an electric current to the material system and/or without the use of an external or non-metallic oxidizing or reducing agent, where an "external" reducing agent can refer to a reducing agent that is not itself part of the metal nanoparticle core, inner metal shell, or outer metal shell of the radioactive nanoparticle. For example, in some instances, the inner metal shell and the outer metal shell of a radioactive nanoparticle described herein are formed without the use of a non-metallic reducing agent. Similarly, forming an outer metal shell can be carried out without the use of any other reactant or reducing agent other than a metal species (such as a metal salt or other metal-containing complex) that serves as the source of the metal for the outer metal shell. Moreover, such a reaction can be carried out in aqueous solution.

Radioactive nanoparticles can also be made in a manner that differs from the method described above. For example, in some embodiments, an inner metal shell may not be formed over the metal nanoparticle core prior to the formation of an outer metal shell through one or more galvanic replacement reactions. Instead, in some cases, a method of making a radioactive nanoparticle comprises providing a metal nanoparticle core and forming an outer metal shell over the metal nanoparticle core through galvanic replacement of at least a portion of the metal nanoparticle core with a second metal or combination of metals, wherein the second metal or combination of metals comprises a metallic radioisotope. The second metal or combination of metals may also include a non-radioactive metallic isotope. Moreover, the second metal or combination of metals can have a higher reduction potential than the metal nanoparticle core. In addition, in some embodiments, the outer shell is formed from a sequence of galvanic replacement reactions. For example, in some instances, forming the outer metal shell comprises carrying out a first galvanic replacement reaction between the metal nanoparticle core and the metallic radioisotope and subsequently carrying out a second galvanic replacement reaction between the metal nanoparticle core and the non-radioactive metallic isotope. In this manner, at least a portion of the metal nanoparticle core (such as an exterior surface portion) can be replaced by the second metal or combination of metals to provide a radioactive nanoparticle having a core-shell structure. For instance, in one non-limiting example, a radioactive Pd shell including a radioactive Pd isotope and a non-radioactive Pd isotope can be formed over a metal nanoparticle core formed from Cu. Other combinations of metals may also be used.

In still other cases, a radioactive nanoparticle can be made by incorporating a radioactive isotope within the metal nanoparticle core, instead of or in addition to incorporating a radioactive isotope within an outer shell disposed over the metal nanoparticle core. For example, in some embodiments, a method of making a radioactive nanoparticle comprises providing a porous hollow nanoparticle (such as a porous hollow nanoparticle described hereinabove), mixing one or more radioisotopes with the hollow nanoparticle to dispose the radioisotopes within the hollow nanoparticle, and sealing the porous hollow nanoparticle. In some cases, sealing the porous hollow nanoparticle comprises providing a metal-containing species capable of undergoing deposition by an oxidation-reduction reaction on the surface of the porous hollow nanoparticle, as described hereinabove in Section IV. For instance, in some embodiments, sealing comprises providing a metal-containing species capable of undergoing electroless deposition on the surface of the porous hollow nanoparticle. The radioactive isotope used in such a method can be a metallic radioisotope, such as Lu-177 or Ac-225 or a metallic radioisotope described hereinabove in Section VIII, or a non-metallic radioisotope, such as B-10, P-32, I-125, or I-131.

X. Methods of Performing Brachytherapy

In another aspect, methods of performing brachytherapy are described herein. In some embodiments, a method of performing brachytherapy comprises disposing a composition described herein within a biological compartment. In some cases, for instance, the composition comprises a plurality of dispersed radioactive nanoparticles, where "dispersed" radioactive nanoparticles are non-agglomerated or substantially non-agglomerated nanoparticles, including nanoparticles having an average size described hereinabove in Section VIII. For instance, in some embodiments, the composition is a colloidal dispersion of the plurality of radioactive nanoparticles. As understood by one of ordinary skill in the art, such a colloidal dispersion can further comprise a solvent or carrier fluid in which the nanoparticles are dispersed. Any solvent or carrier fluid not inconsistent with the objectives of the present disclosure may be used. In some cases, for instance, the colloidal dispersion is an aqueous dispersion. Additionally, in some embodiments, the radioactive nanoparticles are dispersed in a serum or buffer. As described further hereinabove, such a colloidal dispersion of radioactive nanoparticles can provide numerous advantages over the relatively large encapsulated radiotherapeutic agents used in previous methods of performing brachytherapy.

Moreover, in some cases, the composition disposed in the biological compartment comprises a plurality of radioactive nanoparticles, wherein at least one of the plurality of radioactive nanoparticles is a radioactive nanoparticle having a core-shell or core-shell-shell structure described hereinabove in Section VIII. In general, any radioactive nanoparticle described hereinabove in Section VIII can be used. For instance, in some embodiments, the radioactive nanoparticle comprises a metal nanoparticle core, an outer metal shell disposed over the metal nanoparticle core, and a metallic radioisotope disposed within the metal nanoparticle core or within the outer metal shell. Additionally, in some cases, the radioactive nanoparticle has a size of about 30-500 nm in three dimensions. In other instances, the radioactive nanoparticle has a size of 30-400 nm, 30-300 nm, 50-500 nm, 50-400 nm, 50-300 nm, 50-250 nm, 50-200, nm, 50-150 nm, 80-500 nm, 80-300 nm, 80-200 nm, 100-500 nm, 100-400 nm, 100-300 nm, 100-200 nm, 120-450 nm, 120-300 nm, 120-200 nm, or 120-180 nm in each of two or three dimensions. Not intending to be bound by theory, it is believed that a radioactive nanoparticle having a size described herein can be retained within the biological compartment in which the nanoparticle is disposed for long periods, such as periods up to 5 weeks, up to 8 weeks, or up to 10 weeks. Such retention can be especially desirable for embodiments wherein the biological compartment is a tumor or cancerous tissue. For example, in some embodiments wherein a plurality of radioactive nanoparticles are disposed in a tumor or cancerous biological compartment, at least about 70% or at least about 80% of the radioactive nanoparticles are retained within the tumor for at least 3 weeks. In some instances, about 70-99%, 70-95%, 70-90%, 70-80%, 80-99%, 80-95%, 80-90%, 85-99%, or 85-95% of the radioactive nanoparticles are retained within the tumor for a period of 1-10 weeks, 1-5 weeks, 1-3 weeks, 3-10 weeks, 3-8 weeks, 3-5 weeks, 5-10 weeks, or 5-8 weeks.

Moreover, compositions comprising radioactive nanoparticles having a size described herein can also permit the compositions to be disposed in the biological compartment by injection, rather than by surgery. Thus, in some cases, a method of performing brachytherapy described herein comprises injecting the composition into a biological compartment such as a tumor or a region immediately adjacent to a tumor, where a region "immediately adjacent" to a tumor may be within about 5 cm, within about 2 cm, or within about 1 cm of the tumor. Moreover, in some instances, the composition is injected into a blood vessel such as an artery associated with the biological compartment. For example, in some implementations, the composition is injected as part of a transarterial infusion treatment, such as described hereinbelow in the Examples.

It is further to be understood that a method of performing brachytherapy described herein can be used to treat any tumor or cancerous tissue not inconsistent with the objectives of the present disclosure. For example, in some instances, the biological compartment comprises a solid carcinoma, sarcoma, lymphoma, leukemia, blastoma, or germ cell tumor. More particularly, in some cases, the biological compartment comprises breast cancer tissue, prostate cancer tissue, lung cancer tissue, pancreatic cancer tissue, colon cancer tissue, liver cancer tissue, esophageal cancer tissue, gynecologic cancer tissue, anal or rectal cancer tissue, head or neck cancer tissue, brain cancer tissue, or bone cancer tissue. Moreover, in some embodiments, a method described herein can be used to treat a malignant tumor that is unresectable or otherwise not ideal for surgical removal. A tumor can be considered "unresectable" if the tumor adheres to vital structures of the patient or if surgery to remove the tumor would cause irreversible damage to the patient. A method described herein may also be used to treat a relatively small tumor intraoperatively, such as a tumor having a size of 5 cm or less, 2 cm or less, 1 cm or less, or 0.5 cm or less. In addition, as described hereinabove, a method described herein can be used to carry out an intraarterial infusion of the radioactive nanoparticles, thereby permitting treatment of tumors of any size.

Similarly, in some cases, a method described herein can be used to provide brachytherapy to potential regions of residual microscopic disease, including following resection or other treatment of a larger disease site. Thus, in some cases, the biological compartment of a method described herein is a site from which a tumor or other diseased tissue was previously removed. The biological compartment may also be a microscopic region of potentially diseased tissue, where a "microscopic" region can have a volume of less than 10 mm$^3$ or less than 1 mm$^3$. In other embodiments, the biological compartment into which the radioactive nanoparticle is injected or disposed is immediately adjacent to such a microscopic region.

As understood by one of ordinary skill in the art, disposing a radioactive composition described herein in a biological compartment such as a tumor can provide brachytherapy to the biological compartment by means of the radiation emitted by the radioactive composition. Moreover, in some embodiments, a method described herein can also provide treatment or therapy to a biological compartment by carrying out further therapeutic steps in addition to those directed to providing internal radiation to the biological compartment. For instance, in some cases, a method described herein further comprises irradiating the biological compartment with an external beam of ionizing radiation. As understood by one of ordinary skill in the art, "ionizing radiation" can include various types of radiation having an energy sufficient to ionize an atom or molecule by liberating an electron from the atom or molecule. It is further understood that the amount of energy required to liberate the electron can vary depending on the identity or environment of the atom or molecule. In some embodiments, ionizing radiation can be ionizing electromagnetic radiation, such as radiation comprising gamma rays, X-rays, and/or ultraviolet rays in the Hydrogen Lyman-alpha (H Lyman-α), Vacuum Ultraviolet (VUV), or Extreme Ultraviolet (EUV) region of the spectrum. In other instances, the ionizing radiation can comprise a radioactive decay product, such as an alpha particle, beta particle, or neutron. Moreover, in some cases, a radioactive nanoparticle described herein can be a radiosensitizer for the biological compartment. Thus, in some instances, a composition described herein can be used to treat a disease such as cancer by providing internal radiation therapy or brachytherapy and also by enhancing the effect of external radiation therapy. Further, it is also to be understood that, in some embodiments, the radioactive nanoparticle can be a radiosensitizer for the radiation emitted by the radioactive nanoparticle itself, such that the effects of the internal radiation therapy provided by the radioactive nanoparticle are enhanced.

Moreover, in some cases, a composition described herein can also be a hyperthermia agent. In such embodiments, the radioactive nanoparticles of the composition can absorb electromagnetic radiation of an appropriate wavelength and subsequently convert at least a portion of the energy of the absorbed electromagnetic radiation to thermal energy, resulting in an increase in temperature of the radioactive nanoparticles and the nanoparticles' surrounding environment. Therefore, in some cases, a method described herein further comprises exposing the biological compartment in which the radioactive nanoparticles are disposed to a beam of electromagnetic radiation having a wavelength that can be absorbed by the radioactive nanoparticles. In some instances, the electromagnetic radiation includes visible light or is centered in the visible region of the electromagnetic spectrum, such as between 450 nm and 750 nm. In some cases, the electromagnetic radiation includes infrared (IR) light or light centered in the IR region of the electromagnetic spectrum. For example, in some embodiments, the electromagnetic radiation is centered in the near-IR (NIR, 750 nm-1.4 µm), short-wavelength IR (SWIR, 1.4-3 µm), mid-wavelength IR (MWIR, 3-8 µm), or long-wavelength IR (LWIR, 8-15 µm). Moreover, in some embodiments, the electromagnetic radiation overlaps with a spectral wavelength at which water and/or biological tissue has an absorption minimum, such as a wavelength between about 700 nm and about 800 nm or between about 1.25 µm and about 1.35 µm.

Some embodiments described herein are further illustrated in the following non-limiting examples.

EXAMPLE 1

Hollow Au Nanoparticles Formed Using Stacked Membranes

Hollow Au nanoparticles consistent with some embodiments herein were provided as follows. The nanoparticles were formed using a three-electrode electrodeposition cell with a Ag/AgCl electrode in 3 M NaCl solution as the reference and a platinum mesh as the counter electrode, as illustrated in FIG. 1. Potentials were applied to the working electrode using a Princeton Applied Research 273A Potentiostat/Galvanostat. A stack of two to five commercial alumina membranes (Whatman Corp.) provided a plurality of nucleation substrates. Each membrane was about 60 µm thick, with channels extending through the entire thickness. One side of each membrane further exhibited small branches. The channel diameter was about 300 nm and the diameter of the branches varied from about 20 nm to about 200 nm. The channel density was approximately $10^9/cm^2$. Top and cross section views of a membrane are shown in FIG. 2. The membranes were stacked such that the branched side of each membrane was closest to the membrane beneath rather than the membrane above, if any (i.e., the branched sides were oriented to be on bottom rather than on top of each layer in the stack of membranes). A 500 nm Cu layer was sputter-deposited on the bottom side of the bottom membrane in the stack and served as the working electrode. A Teflon cell with an o-ring 1 cm in diameter was placed on the top of the membrane stack.

An electrolyte was disposed in the electrodeposition cell described above. The electrolyte was prepared by first preparing an aqueous solution composed of ~3% (by volume) sulfuric acid (18 M, Alfa Aesar), ~3% (by volume) ethylenediamine (EDA, 50% solution diluted from 99%, Sigma-Aldrich), ~10% (by volume) sodium gold sulfite ($Na_3Au(SO_3)_2$, 10% solution diluted from pH 10.5 solution purchased from Colonial Metals, Inc.), and ~7% (by volume) sodium sulfite ($Na_2SO_3$) (2M aqueous solution, Sigma-Aldrich). The solution had a pH of about 7.0. The solution was then altered by adding 0.01 M sulfuric acid ($H_2SO_4$) or 0.4 M aqueous nickel sulfamate ($Ni(SO_3NH_2)_2$, prepared using deionized water and 98% nickel sulfamate tetrahydrate ($Ni(SO_3NH_2)_2 \cdot 4H_2O$) purchased from Sigma-Aldrich) to reduce the pH to ~6.0.

After disposing the electrolyte in the electrodeposition cell, a potential more negative than −0.6 V (vs. Ag/AgCl) was applied, resulting in the formation of large Au nanorods and smaller hollow Au nanoparticles. The hollow Au nanoparticles were observed on the inner pore wall surfaces of all the membranes. More hollow nanoparticles were observed in membranes closer to the bottom electrode. The number of these hollow nanoparticles gradually decreased with the distance from the bottom electrode, as shown in FIG. 3. Some electrodeposited Au nanorods can be seen at the bottom of FIG. 4, while some hollow Au nanoparticles can be seen in FIGS. 3 and 4. Branches at the bottom of each membrane can be seen at the bottom of FIG. 3A and FIG. 3B.

The hollow Au nanoparticles were isolated by first pouring out the electrolyte from the cell and washing using deionized water. Deionized water was then added to the cell and kept there for at least half an hour to allow complete diffusion of the electrolyte out of the membranes. This process was repeated at least three times. Membranes in the stack were then individually dissolved using 1 M sodium hydroxide (NaOH) solution. The remaining hollow Au nanoparticles were purified by several cycles of dispersion in deionized water followed by centrifugation. FIG. 4 shows the accumulation of hollow Au nanoparticles on top of the electrodeposited metal on the working electrode after dissolving the first membrane.

Figure 6A:
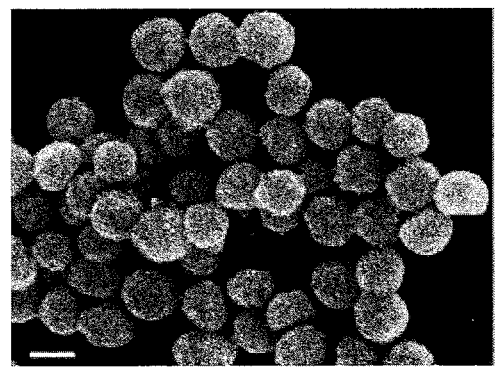
FIG. 6A is an SEM image of hollow Au nanoparticles according to some embodiments described herein, before ion milling. Scale bar=100 nm.
Figure 6B:
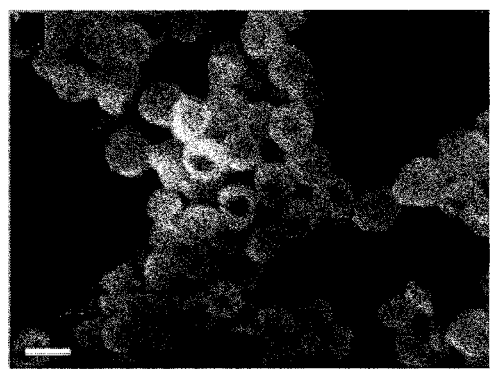
FIG. 6B is an SEM image of hollow Au nanoparticles according to some embodiments described herein, after ion milling. Scale bar=100 nm.
Figure 7A:
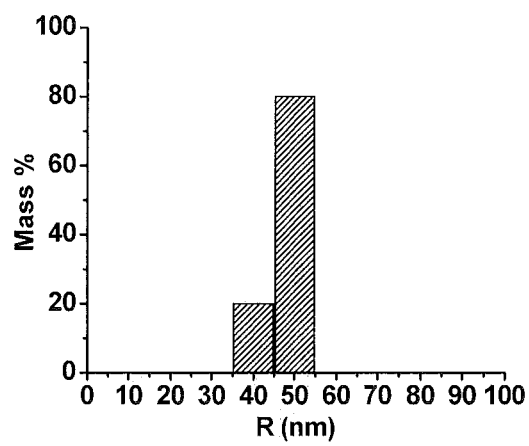
FIG. 7A is a plot of particle size distribution for a population of hollow Au nanoparticles according to some embodiments described herein, as measured by Dynamic Light Scattering (DLS). The mean radius is 53±5 nm.
Figure 7B:
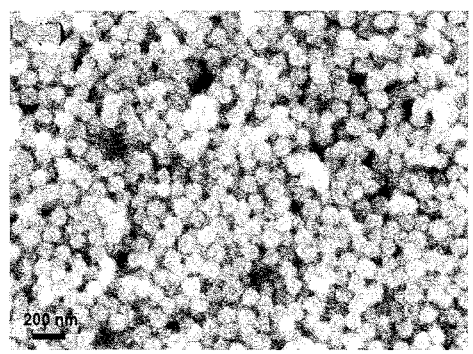
FIG. 7B is an SEM image of hollow Au nanoparticles according to some embodiments described herein. Scale bar=200 nm.

The hollow Au nanoparticles were characterized using scanning electron microscopy (SEM), transmission electron microscopy (TEM), and dynamic light scattering (DLS). Bright field images and selective area electron diffraction (SAED) patterns were acquired using a Hitachi H9500 HR-TEM operating at 300 kV. Samples were prepared by placing a drop of hollow Au nanoparticle suspension on a carbon coated copper grid, waiting 10 minutes for the particles to settle on the grid, and then removing excess solution. FIG. 5 shows TEM micrographs (A-C) and a selected area diffraction pattern (D) of hollow Au nanoparticles. Ion milling was used to open the hollow Au nanoparticles for further characterization. SEM micrographs were taken using a ZEISS Supra 55 VP SEM. Samples were prepared by spreading diluted aqueous suspensions of hollow Au nanoparticles on a piece of silicon wafer, forming a monolayer of nanoparticles on the surface. Ion milling was performed using a Gatan Precision Ion Polishing System with 4.5 keV ion guns tilted at 4 degrees for 5 minutes. The two beam currents were 36 µA and 48 µA, and the sample was rotated at 4 rpm. FIG. 6 shows the treated hollow Au nanoparticles. FIG. 7 shows the size distribution of a population of hollow Au nanoparticles using DLS.

EXAMPLE 2

Hollow Au Nanoparticles Formed Using a Patterned Substrate

Figure 9A:
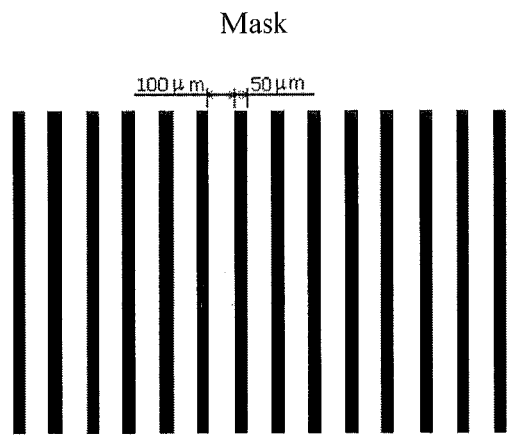
FIG. 9A shows a photolithography photomask pattern for a substrate suitable for use in some methods described herein.
Figure 9B:
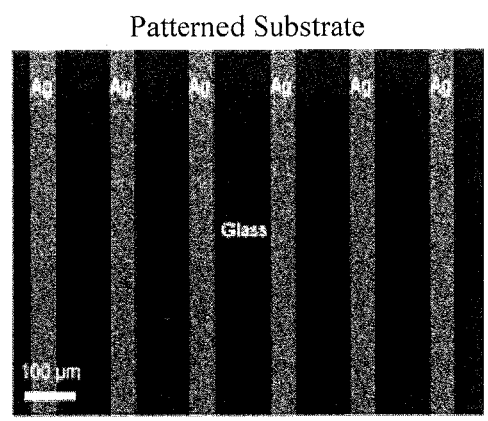
FIG. 9B shows a patterned substrate suitable for use in some methods described herein, comprising silver (Ag) stripes on silica ($SiO_2$). Scale bar=100 µm.

Hollow Au nanoparticles consistent with some embodiments herein were provided as follows. The hollow Au nanoparticles were formed using a three-electrode cell with a Ag/AgCl electrode in 3 M NaCl solution as the reference and a platinum mesh as the counter electrode, as shown in FIG. 8. A lithographically pattered electrode consisting of Ag stripes on a glass substrate (an optical microscope slide) was used as the working electrode. The optical microscope glass slide was rinsed with deionized water and then cleaned with plasma treatment before use. Photolithography was used to pattern the glass substrate. The photomask design is shown in FIG. 9A. The width of the stripes was 50 µm, and the stripes were duplicated every 100 µm. The Ag stripe patterned substrate is shown in FIG. 9B. The uncoated glass regions of the substrate provided surfaces for the nucleation and growth of hollow Au nanoparticles. Potentials were applied to the working electrode using a Princeton Applied Research 273A Potentiostat/Galvanostat.

An electrolyte was disposed in the electrodeposition cell described above. Reagent grade chemicals used to prepare various electrolytes included the following. Aqueous sodium gold sulfite ($Na_3Au(SO_3)_2$) solution with a pH ~10.5 was purchased from Colonial Metals Inc., and diluted to 10% or 5% with deionized water. Ethylenediamine (EDA, 99%, Sigma-Aldrich) was diluted to 50% or 5% with deionized water. Aqueous solution of 0.4 M nickel sulfamate ($Ni(SO_3NH_2)_2$) with a pH ~5.8 was prepared using deionized water and 98% nickel sulfamate tetrahydrate ($Ni(SO_3NH_2)_2.4H_2O$) purchased from Sigma-Aldrich. To prepare a series of electrolytes, the components indicated in Table 1 were mixed, and the electrolytes were further acidified with 5% sulfuric acid to reach a pH of about 6.

TABLE 1

Electrolytes.

| Electrolyte | $Na_3Au(SO_3)_2$ (5%) | EDA (5%) | $Ni(SO_3NH_2)_2$ (0.4M) |
|---|---|---|---|
| 1 | 1 mL | | |
| 2 | 0.5 mL | 0.5 mL | |
| 3 | 0.5 mL | | 0.5 mL |
| 4 | 0.5 mL | 0.5 mL | 0.5 mL |

Figure 10A:
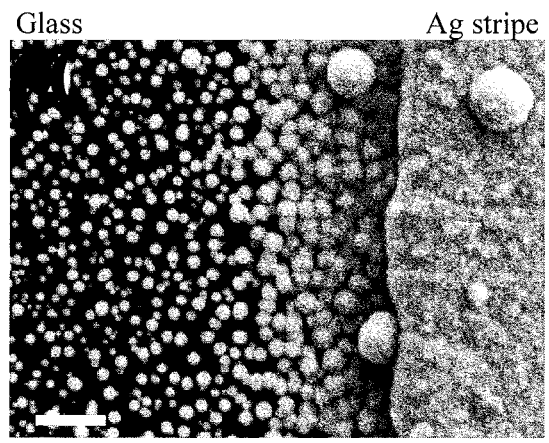
FIG. 10A is an SEM image of Au nanoparticles according to some embodiments described herein, on a Ag/$SiO_2$ substrate. Scale bar=1 µm.
Figure 10B:
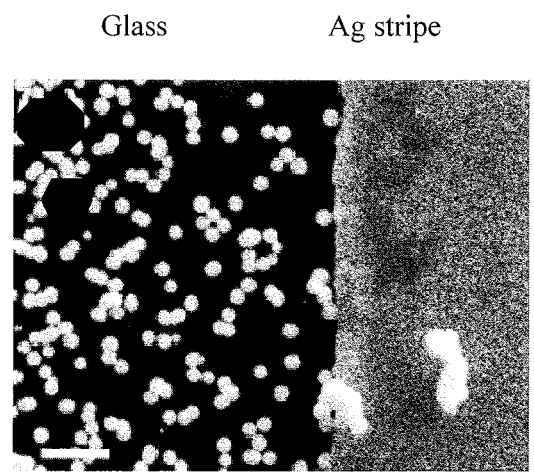
FIG. 10B is an SEM image of Au nanoparticles according to some embodiments described herein, on a Ag/$SiO_2$ substrate. Scale bar=1 µm.

After disposing an electrolyte in the electrodeposition cell, a potential was applied. When a potential more negative than the hydrogen evolution equilibrium potential was applied to the Ag stripes, a large number of gold nanoparticles were formed on the glass areas, as shown in FIG. 10 (scale bar is 1 μm). The nanoparticles in FIG. 10A were formed using an electrolyte without $Ni^{2+}$. The nanoparticles in FIG. 10B were formed using an electrolyte including $Ni^{2+}$.

EXAMPLE 3

Hollow Au Nanoparticles Using a TEM Grid

Hollow Au nanoparticles consistent with some embodiments herein were provided as follows. The hollow Au nanoparticles were formed using a method similar to that described in Example 2, except a TEM grid was used as the working electrode and nucleation substrate. The TEM grid comprised a copper mesh coated with a carbon film. As shown in FIG. 11, hollow Au nanoparticles were observed on the carbon film. The scale bar is 1 μm. Characterization by high resolution TEM (HR-TEM) was carried out after the electrodeposition without any further treatment.

EXAMPLE 4

Hollow Au Nanoparticles with a Porous Shell

Hollow Au nanoparticles consistent with some embodiments herein were provided as follows. The nanoparticles were formed using a method similar to that described in Example 1. An electrodeposition cell as described in Example 1 was used, except a stack of two instead of five anodic alumina filtration membranes was used, and a 700 nm layer of Cu was sputter deposited to block the pores of the bottom membrane and serve as the working electrode. A commercial Au sulfite solution (Techni-Gold 25 ES RTU from Technic, Inc.) was used as the electrolyte. The initial pH of the solution was about 7.0. The solution was altered by adding 0.4 M Ni sulfamate solution to change the pH to about 6.0. A potential of −0.80 V (vs. Ag/AgCl reference) was applied to the working electrode using a Princeton Applied Research 273A Potentiostat/Galvanostat. Hydrogen evolution occurred at this potential. To obtain hollow Au nanoparticles having a porous shell, the reaction time was held to less than 10 minutes. The hollow Au nanoparticles with porous shells were purified and isolated as described in Example 1.

EXAMPLE 5

Hollow Au Nanoparticles Comprising Hollow Au Nanoparticles

Figure 13:
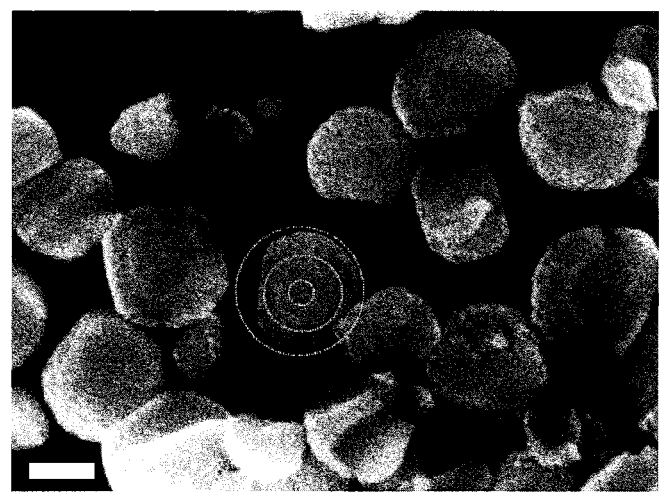
FIG. 13 is an SEM image of double-shell nanoparticles according to some embodiments described herein, after ion milling treatment. Scale bar=200 nm.
Figure 14A:
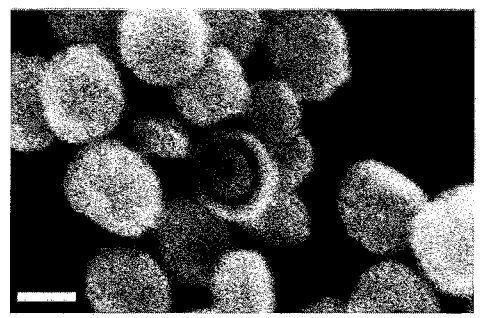
FIG. 14A is an SEM image of double-shell nanoparticles according to some embodiments described herein. Scale bar=100 nm.
Figure 14B:
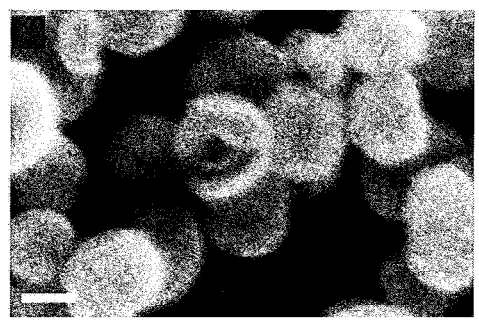
FIG. 14B is an SEM image of double-shell nanoparticles according to some embodiments described herein. Scale bar=100 nm.

Hollow Au nanoparticles consistent with some embodiments herein were provided as follows. The hollow Au nanoparticles were formed using a method similar to that described in Example 1, except the applied potential was pulsed. Fabrication of nanoparticles was initiated with an applied potential of −0.8 V (vs. Ag/AgCl) for 600 seconds followed by an open circuit for 300 seconds. The pulse potential was repeated for two additional cycles. Double-shell nanoparticles were obtained, as shown in FIG. 13. The average diameter of the inner cavities was about 50 nm, and the overall size was about 300 nm. The scale bar is 200 nm. Other double-shell nanoparticles are shown in FIG. 14. The scale bar in FIG. 14A-C is 100 nm. The scale bar in FIG. 14D is 20 nm.

EXAMPLE 6

Hollow Au Nanoparticles Comprising $Fe_3O_4$ Nanoparticles

Hollow Au nanoparticles comprising $Fe_3O_4$ nanoparticles consistent with some embodiments herein were provided as follows. Hollow Au nanoparticles with porous shells were prepared in a manner similar to that described in Example 4. The pH value of the electrolyte was adjusted with 0.2 M sodium sulfite to reach a pH of about 6.5, and the reaction time was between 400 and 600 seconds. The resulting hollow Au nanoparticles had a cavity about 50 nm in diameter and a shell less than about 25 nm thick. The shell was porous and exhibited pore sizes of about 2-3 nm, as measured by HR-TEM.

To produce iron oxide nanoparticles within the hollow Au nanoparticles, 5.2 g (0.032 mol) anhydrous $FeCl_3$ and 2 g (0.016 mol) $FeCl_2$ were added under vigorous stirring to 25 mL deionized water containing 0.85 mL HCl (12.1 N). After this, the mixed solution of $FeCl_2$ and $FeCl_3$ in HCl was diluted 40 times with deionized water. The resulting aqueous solution was delivered into the channels of an alumina membrane loaded with the hollow Au nanoparticles described above using vacuum filtration, where the alumina membrane served as the "filter" in the vacuum filtration procedure. The wetted alumina membrane was then immersed in the $FeCl_3/FeCl_2$ solution for about 30 minutes. The membrane was then transferred into 5 mL of 30% $NH_4OH$ aqueous solution and left there for an additional 10-20 minutes. A yellow-orange color appeared, indicating the formation of iron oxide nanoparticles. Free iron oxide nanoparticles (about 10 nm in diameter) formed inside the alumina membrane but outside the hollow Au nanoparticle cavities were removed by passing deionized water through the membrane under vacuum filtration. The membrane was then dissolved using 1-2 M NaOH (aq.), and $Fe_3O_4$/Au core/shell nanoparticles were released into solution. The nanoparticles were purified by several cycles of dispersion in deionized water followed by centrifugation. This process is depicted in FIG. 15.

Figure 16A:
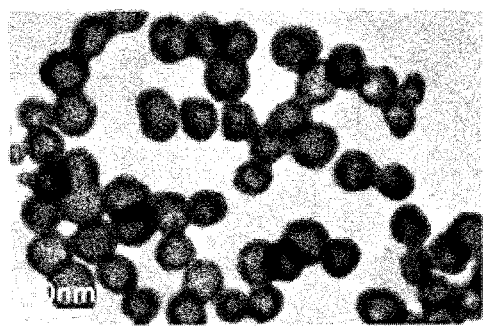
FIG. 16A is a TEM image of porous nanoparticles according to some embodiments described herein, before loading with other nanoparticles, according to some embodiments described herein. Scale bar=200 nm.
Figure 16B:
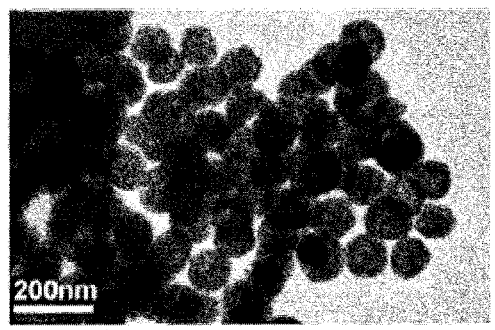
FIG. 16B is a TEM image of the nanoparticles of FIG. 16A after loading, according to some embodiments described herein. Scale bar=200 nm.
Figure 16C:
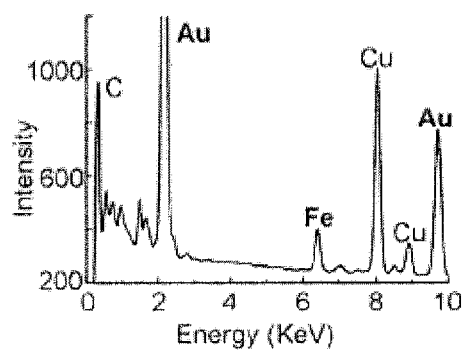
FIG. 16C is an energy dispersive x-ray spectroscopy (EDS) spectrum of one composite nanoparticle from FIG. 16B.
Figure 16D:
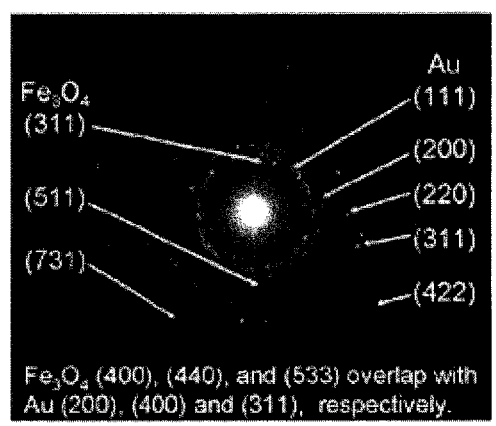
FIG. 16D is an SAED pattern of three composite nanoparticles from FIG. 16B.

The composite nanoparticles were characterized by energy dispersive x-ray spectroscopy (EDS) and TEM, including selected area electron diffraction (SAED). The optical and magnetic properties of the composite particles were also examined. FIG. 16 shows TEM images (FIG. 16A) before and (FIG. 16B) after loading of iron oxide nanoparticles into the hollow Au nanoparticles. During the precipitation of $Fe_3O_4$ nanoparticles within the cavity of the hollow Au nanoparticles, $Fe_3O_4$ nanoparticles also formed outside of the cavity. But the TEM images indicated that no small iron oxide nanoparticles were attached to the outer surface of the hollow Au nanoparticles. The free (i.e., not trapped within a hollow Au nanoparticle cavity) $Fe_3O_4$ nanoparticles were less than 20 nm in diameter and were readily separated from the $Fe_3O_4$/Au composite particles using filtration and centrifugation. The loading of $Fe_3O_4$ into the core of porous hollow Au nanoparticles was confirmed by EDS analysis of a single composite particle (FIG. 16C) and the selected area electron diffraction (SAED) pattern derived from three composite particles (FIG. 16D).

Figure 17A:
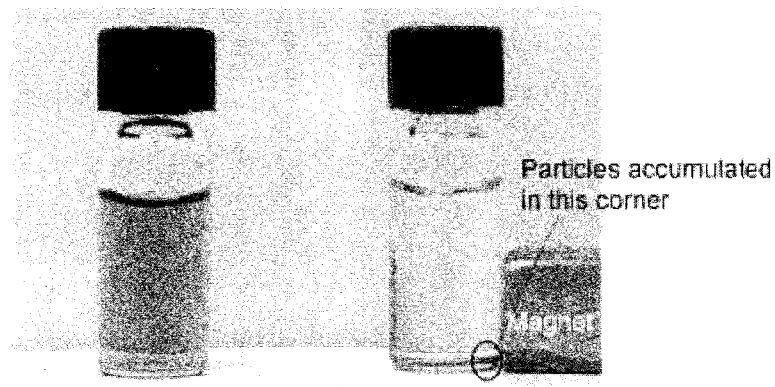
FIG. 17A is a series of photographs of a vial containing composite nanoparticles according to some embodiments described herein.
Figure 17B:
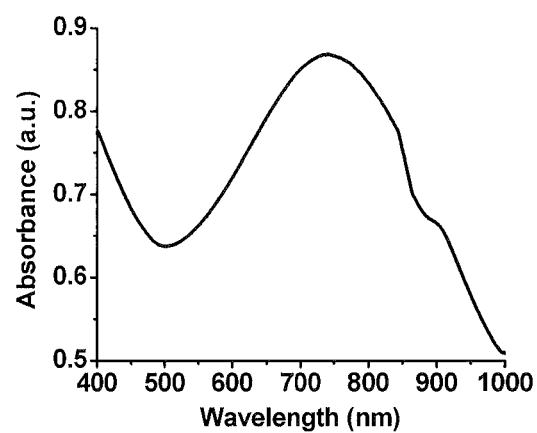
FIG. 17B is an absorption spectrum of an aqueous suspension of nanoparticles according to some embodiments described herein.

An aqueous suspension of $Fe_3O_4$/Au composite particles is shown in FIG. 17A. The suspension was cyan colored, indicating that the suspension absorbed red light. The absorption peak shown in FIG. 17B corresponded to the SPR wavelength of the hollow Au nanoparticles. The absorption profile of the hollow Au nanoparticles varied little before and after $Fe_3O_4$ loading. Not intending to be bound by theory, the maintenance of the absorption profile might have been due to the thickness of the Au shell (>20 nm). Therefore it was possible to independently select and maintain the optical properties of the hollow nanoparticle host.

Figure 18:
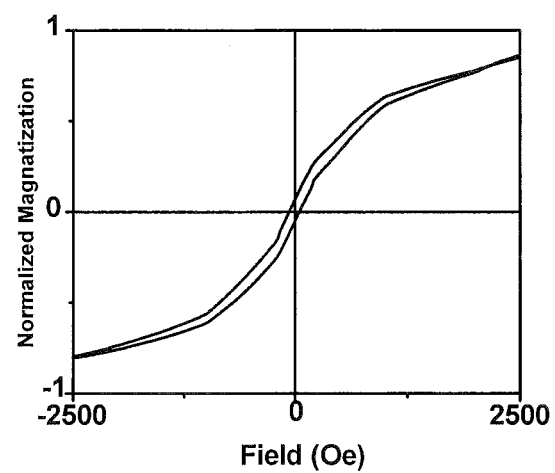
FIG. 18 is a hysteresis loop of a dried powder of nanoparticles according to some embodiments described herein.

Further, as shown in FIG. 17A, the composite particles could be dragged towards a permanent magnet. The magnetization curve of a dried power comprising the $Fe_3O_4$/Au composite particles exhibited hysteresis, as shown in FIG. 18. The shape of the curve suggested the presence of some smaller (<20 nm), superparamagnetic $Fe_3O_4$ nanoparticles as well as some larger (>30 nm), ferromagnetic $Fe_3O_4$ nanoparticles within the cavities of the hollow Au nanoparticles.

EXAMPLE 7

Hollow Au Nanoparticles Comprising Doped $Fe_3O_4$ Nanoparticles

Figure 19:
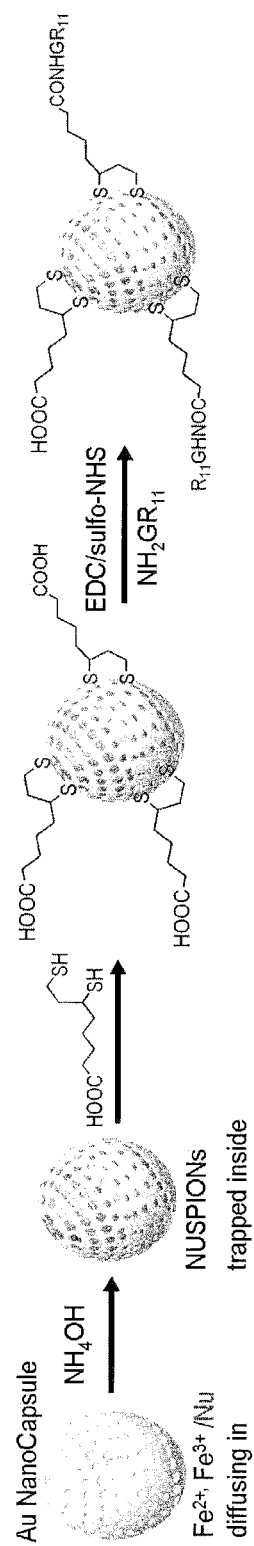
FIG. 19 illustrates a method of making composite particles according to one embodiment described herein.

Hollow Au nanoparticles comprising doped $Fe_3O_4$ nanoparticles consistent with some embodiments herein are provided as follows. Hollow Au nanoparticles comprising $Fe_3O_4$ nanoparticles are prepared in a manner similar to that described in Example 6, except a source of dopant ions is also provided along with sources of $Fe^{2+}$ and $Fe^{3+}$ ions. The dopant ions include nuclides useful for positron emission tomography (PET) imaging, such as $^{64}Cu^{2+}$ or $^{89}Zr^{4+}$. Once the Au/doped $Fe_3O_4$ nanocomposites are prepared and purified in a manner similar to that described in Example 6, the surfaces are functionalized as follows. Prior to dissolution of the alumina membrane, a solution of lipoic acid or dihydrolipoic acid (DHLA) is added to the membrane resulting in the association of this ligand with the hollow Au nanoparticle surface. The membrane is then further rinsed with deionized water. The carboxylic acid groups of the lipoic acid/DHLA ligands are then coupled to $NH_2GR_{11}$ using carbodiimide coupling with N-(3-dimethylaminopropyl)-N"-ethylcarbodiimide hydrochloride (EDC) and N-hydroxysulfosuccinimide (sulfo-NHS), where $NH_2GR_{11}$ is a prostate cancer specific polyarginine peptide described, for example, in Gao et al., *Amino Acids,* 2010 Mar. 11: 20221650, which is hereby incorporated by reference in its entirety. The nanocomposite particle comprising the peptide targeting agent is then purified by size exclusion high performance liquid chromatography (HPLC) or three cycles of centrifugation filtration using centricon filters with a molecular weight cutoff of about 30 kDa. This process is depicted in FIG. 19.

EXAMPLE 8

Hollow Au Nanoparticles Comprising a Therapeutic Agent

Hollow Au nanoparticles consistent with some embodiments herein are provided as follows. Hollow Au nanoparticles with porous shells are prepared in a manner similar to that described in Example 4 or Example 6. Then an alumina membrane loaded with the porous hollow Au nanoparticles is immersed into a concentrated solution of a therapeutic agent, such as a drug. The membranes are kept in the solution for a sufficient time (such as 10-600 minutes) to allow diffusion of the therapeutic agent into the Au nanoparticle cavities. Then a metal-containing precursor, such as $Na_3Au(SO_3)_2$, is added to the solution in the membrane to allow the porous Au shell to grow, sealing at least some of the pores. The resulting hollow Au nanoparticles comprising a therapeutic agent can then be used for medical treatment. The encapsulated therapeutic agent is released by rupturing the Au shell. The shell is ruptured by irradiating the shell with light having a wavelength at or near the SPR frequency of the shell.

EXAMPLE 9

Hollow Au Nanoparticles Comprising a Raman Active Species

Figure 20:
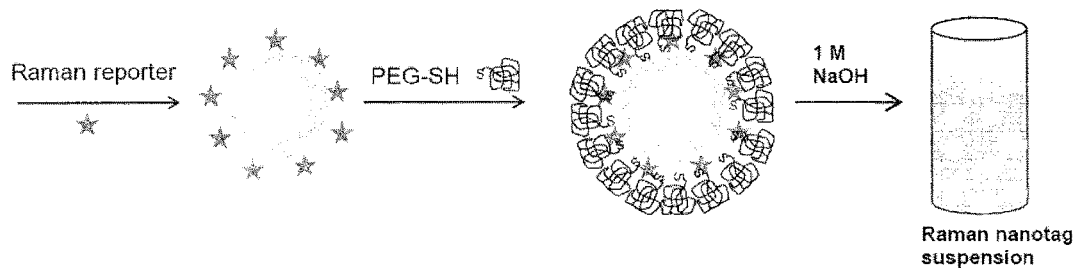
FIG. 20 illustrates a method of making nanoparticles according to one embodiment described herein.

Hollow Au nanoparticles consistent with some embodiments herein were provided as follows. Hollow gold nanoparticles were synthesized as described in Example 4. The hollow gold nanoparticles had a cavity diameter of about 50 nm and an outer diameter of about 100 nm, with an absorption peak centered at 730 nm. An anodic aluminum oxide membrane containing about $1.1 \times 10^{11}$ nanoparticles/mL was immersed in a freshly made 20 mL solution of 5 µM diethylthiatricarbocyanine (DTTC) Raman reporter dye and kept there for 3 hours at room temperature. The alumina membrane was then rinsed with deionized water several times. The nanoparticle-loaded membrane was then immersed overnight in a solution of 20 µM SH-mPEG (MW 5 kDa, where mPEG refers to methoxy polyethylene glycol) at 4° C. The alumina membrane was then dissolved using 1 M NaOH solution. The nanoparticles were purified by several cycles of dispersion in deionized water followed by centrifugation. This process is illustrated in FIG. 20.

Figure 21:
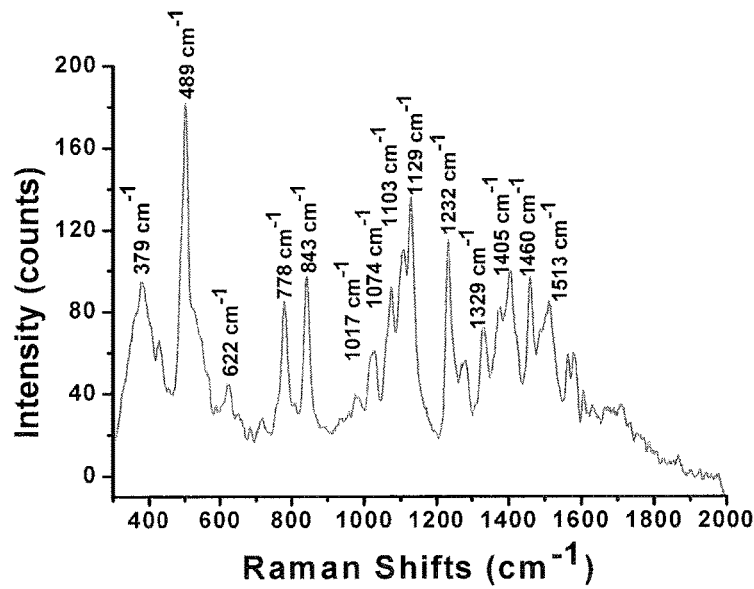
FIG. 21 is a Raman spectrum of a composite particle according to some embodiments described herein.
Figure 22:
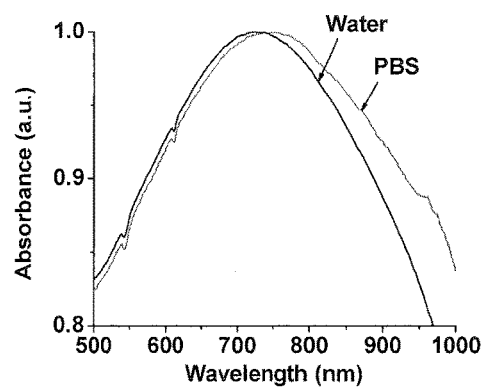
FIG. 22 is a comparison of the absorption spectra of nanoparticles according to some embodiments described herein, in water and in 10 mM phosphate buffered saline (PBS).
Figure 23A:
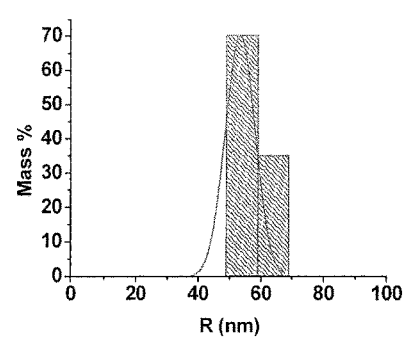
FIG. 23A is a plot of the particle size distribution of nanoparticles according to some embodiments described herein, measured by DLS.
Figure 23B:
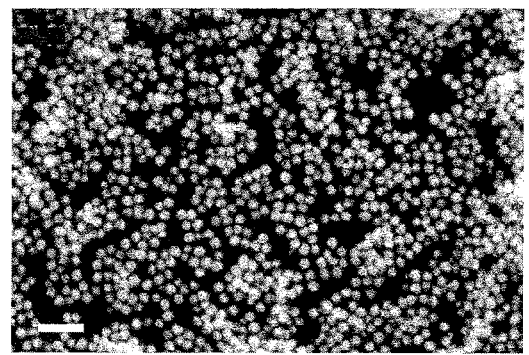
FIG. 23B is an SEM image of nanoparticles according to some embodiments described herein. Scale bar=5 nm.

The resulting hollow Au nanoparticles comprising a Raman active species, also referred to as "Raman nanotags," were characterized by Raman spectroscopy. Raman spectroscopy measurements were conducted in a home-made setup with 785 nm laser light. The laser light was propagated through an optical fiber (600 µm, NA=0.39) to a Raman module. At the Raman module, the light from this fiber was attenuated by a neutral density filter (ND=0.2) and collimated before it was incident on a dichotic which reflected the light onto a 20×, 0.4 NA objective lens with a working distance of 8.4 cm. The cell containing the Raman nanotag suspension was placed at the focus of this lens for surface enhanced Raman spectroscopy (SERS) measurement. Light reflected and scattered by the suspension was collected by the objective and transmitted by the dichotic to a notch filter before being focused by a 10×, 2.5 NA lens into an optical fiber (600 μm, NA=0.39) which then propagateed the light to a spectrometer. Spectra were acquired with an exposure time of 8 seconds. The Raman spectra of a 50 μL solution of Raman nanotags with a concentration of $5.8 \times 10^{10}$ nanoparticles/mL exhibited the major vibrational modes of DTTC at 379, 489, 622, 778, 843, 1017, 1074, 1103, 1129, 1232, 1329, 1405, 1460 and 1513 $cm^{-1}$, as shown in FIG. 21. The Raman nanotags were stable in 10 mM phosphate buffered saline (PBS), as shown in FIG. 22. The Raman nanotags were also stable in 3 M NaCl at room temperature for up to one month. No aggregation was observed by UV-vis spectroscopy. The size of the Raman nanotags was measured by DLS in PBS. As shown in FIG. 23, the measured size in PBS was about 10 nm greater than the size indicated by SEM. The scale bar is 500 nm.

The cytotoxicity of the Raman nanotags was evaluated using the PC-3 cell line, a human prostate cancer cell line (American Type Culture Collection, Manassas, Va.). Cells were maintained in GIBCO's T-medium supplemented with 5% FBS (fetal bovine serum), and 1× Penicillin/Streptomycin. Cells were incubated at 37° C. in a 5% $CO_2$ environment and were passed at 75% confluence in P150 plates. The cultured PC-3 cells were harvested from monolayer using PBS and trypsin/EDTA and suspended in T-media with 5% FBS. The cytotoxicity evaluation was performed using [$^3$H]-thymidine incorporation, which is a measurement of DNA synthesis rate as a marker for cell proliferation. Approximately 3000 cells were seeded in a flat-bottomed 96-well polystyrene coated plate and incubated for 24 hours at 37° C. in a 5% $CO_2$ incubator. The hollow gold nanoparticles with different coatings (PEG only versus Raman reporter dye with PEG) were suspended in the T-medium. The evaluated concentrations were 960, 480, 96, and 9.6 mM. The hollow gold nanoparticle-loaded T-medium was added to the plate in hexaplets. After 24 hours of incubation of cells and nanoparticles, the T-medium was aspirated from each well, and the cell layer was rinsed 3 times with complete growth T-medium and then [$^3$H]-thymidine solution (1 μCi/100 μL T-medium) was added to each well. After 2 hours incubation, the medium was aspirated from each well and the cell layer was rinsed 3 times with complete growth T-medium. The cells were then solubilized with 100 μL of 2 N NaOH solution. The solutions were collected from the wells and added to scintillation vials containing 5 mL of Budget-Solve Complete Counting Cocktail. Finally, [$^3$H]-thymidine incorporated into DNA was quantified by Liquid Scintillation β-Counter (Beckman LS 6500). Statistically, the treated cells showed the same viability as the control.

EXAMPLE 10

Hollow Au Nanoparticles Comprising a Targeting Species

Hollow Au nanoparticles consistent with some embodiments herein were provided as follows. Raman nanotags were prepared as described in Example 9, except addition of the Raman reporter dye and polyethylene glycol was carried out as follows. A freshly prepared solution of Raman reporter dye was flowed through the alumina membrane loaded with porous hollow Au nanoparticles followed by the flow through the membrane of a mixture of SH-mPEG (10 μM, MW 5 kDa) and SH-PEG-COOH (1 μM, MW 2 kDa) solutions at a volumetric ratio of 2:7. To a 1 mL solution of the purified Raman nanotags, EDC and sulfo-NHS were added and incubated for 30 minutes. The composite particles were then purified by three cycles of centrifugation followed by redispersion in PBS. Anti-PSMA (where "PSMA" refers to a type II transmembrane glycoprotein overexpressed in prostate cancers) was then added to the solution of activated ester nanotags, and the mixture was allowed to react at 4° C. overnight. The resulting antibody-nanotag conjugate was purified by either size exclusion column separation or centricon centrifugation.

EXAMPLE 11

Hollow Au Nanoparticles with a Roughened Surface

Figure 24A:
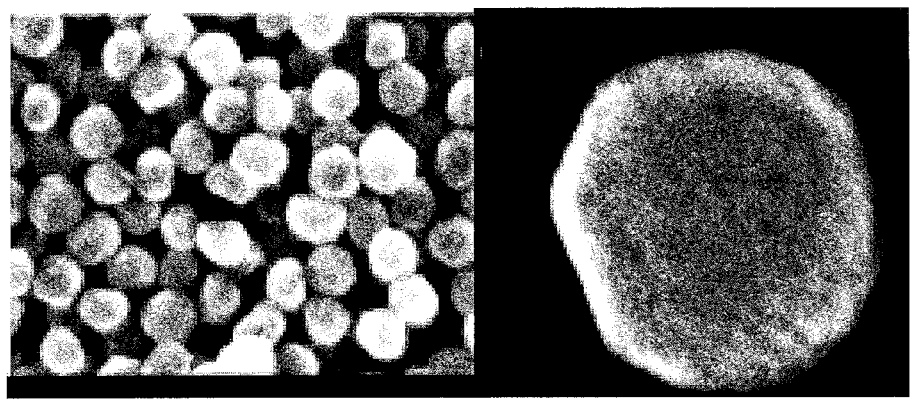
FIG. 24A is an SEM image of hollow Au nanoparticles according to some embodiments described herein.
Figure 24B:
FIG. 24B is an SEM image of hollow Au nanoparticles according to some embodiments described herein.
Figure 24C:
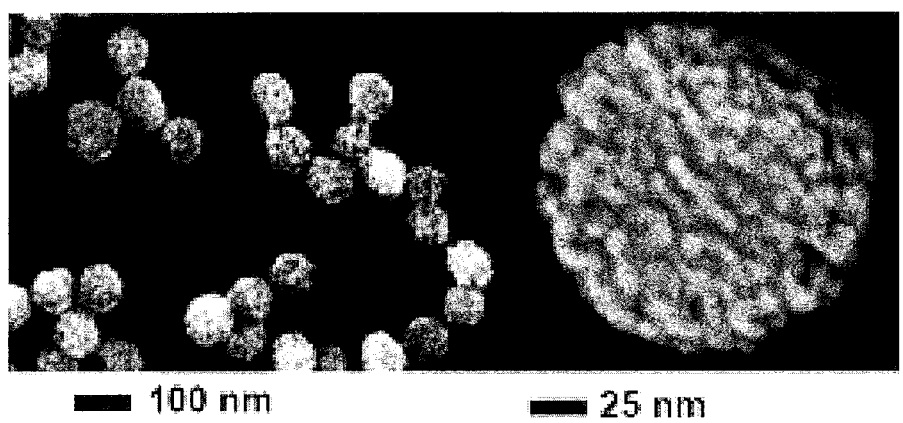
FIG. 24C is an SEM image of hollow Au nanoparticles according to some embodiments described herein.
Figure 25A:
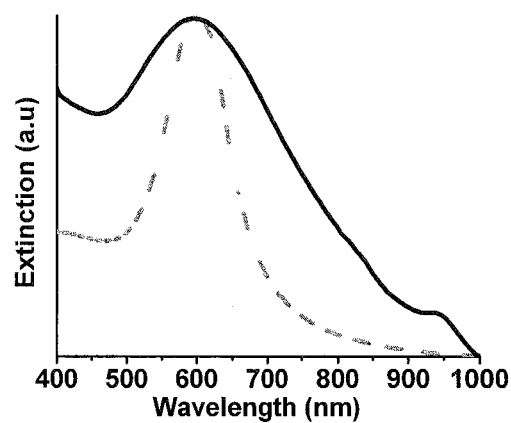
FIG. 25A is a comparison of experimental (solid line) and simulated (dashed line) absorption spectra of hollow Au nanoparticles according to some embodiments described herein.
Figure 25B:
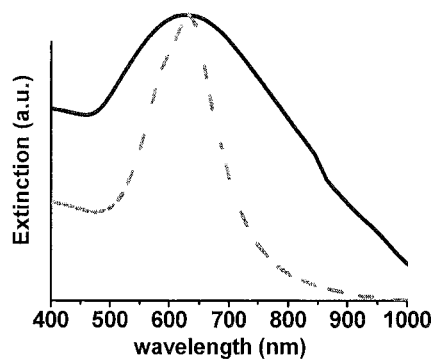
FIG. 25B is a comparison of experimental (solid line) and simulated (dashed line) absorption spectra of hollow Au nanoparticles according to some embodiments described herein.
Figure 25C:
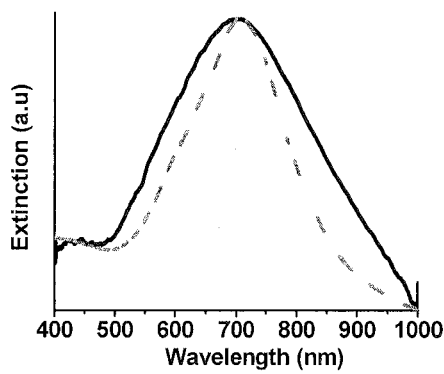
FIG. 25C is a comparison of experimental (solid line) and simulated (dashed line) absorption spectra of hollow Au nanoparticles according to some embodiments described herein.

Hollow Au nanoparticles consistent with some embodiments herein were provided as follows. Hollow Au nanoparticles having a roughened surface were prepared in a manner similar to that described in Example 1, except the pH of the electrolyte was altered as follows. Hollow Au nanoparticles prepared using an electrolyte with a pH of about 6.0 exhibited relatively smooth shells. To increase the surface roughness, the pH of the electrolyte was increased to about 6.5 or 7.0 through the addition of 2 M $Na_2SO_3$ (pH about 9.0). Not intending to be bound by theory, the pH dependence of the roughness can be attributed to the increase in the rate of the autocatalytic reaction of $Na_3Au(SO_3)_2$ (and thus grain growth and final grain size) with pH. FIG. 24 shows the surface morphology of hollow gold nanoparticles synthesized using electrolytes with different pH values. FIG. 24A shows a smooth shell formed at an electrolyte pH of about 6.0. FIG. 24B shows a shell having a surface roughness of about 5 nm and formed at an electrolyte pH of about 6.5. FIG. 24C shows a shell having a surface roughness of about 8 nm and formed at an electrolyte pH of about 7.0. FIG. 25 shows the corresponding absorption spectra of aqueous suspensions of the hollow Au nanoparticles. The dashed lines in FIG. 25 correspond to simulated absorption profiles. The plasmon peak shifted to longer wavelength with the increase of electrolyte pH. When the pH changed from about 6.0 to 6.5 to 7.0, the SPR peaks shifted from about 600 nm to 630 nm to 730 nm.

EXAMPLE 12

Hemispherical and Tubular Au Nanoparticles

Hemispherical and tubular Au nanoparticles consistent with some embodiments herein were provided as follows. An electrochemical deposition cell similar to that described in Example 1 was used. An electrolyte was disposed in the electrodeposition cell. The electrolyte was prepared by first preparing an aqueous solution composed of ~3% sulfuric acid, ~3% ethylenediamine (EDA), ~10% sodium gold sulfite ($Na_3Au(SO_3)_2$), and ~7% sodium sulfite ($Na_2SO_3$). The solution had a pH of about 7.0. The solution was then altered by adding 0.01 M sulfuric acid ($H_2SO_4$) to reduce the pH to about 4.0. After disposing the electrolyte in the electrodeposition cell, a potential more negative than −0.6 V (vs. Ag/AgCl) was applied for about 10-60 minutes. With a deposition time of about 10 minutes, hemispherical gold nanoparticles were observed on the pore walls (FIG. 26A). With a deposition time of about 60 minutes, tubular nanoparticles were observed (FIG. 26B). The scale bars in FIG. 26 are 200 nm. Not intending to be bound by theory, it is believed that nanoparticle morphology is affected by the contact angle of $H_2$ bubbles on the pore wall surface, which is in turn affected by the hydrophobicity of the pore wall surface.

EXAMPLE 13

Photothermal Properties of Hollow Au Nanoparticles

The photothermal properties of hollow Au nanoparticles in tissue-like phantoms under near infrared (NIR) laser irradiation were investigated. Gel phantoms were prepared using 1% Intralipid, gelatin powder, and paraformaldehyde. Briefly, 2400 mg of highly purified gelatin powder was mixed with 228 mL of deionized water. The mixture was then heated by microwave for 2-4 minutes (to about 900° C.) with intermittent mixing until the gelatin was dissolved and the solution appeared clear and colorless. With continuous mixing at room temperature, the gelatin solution was permitted to cool to 600° C., at which time 12 mL of 1% Intralipid (20% fat emulsion, Sigma-Aldrich) and 140 mg paraformaldehyde (95%, Sigma-Aldrich) were added, which caused the solution to become white and opaque. After formation of the gel phantom, a thin pocket was created in the phantom. A suspension of hollow Au nanoparticles (50 µL, $3.0 \times 10^9$ nanoparticles/mL) having a SPR peak centered at 750 nm was disposed in the pocket via pipet. A diode laser fiber (mean wavelength of 810 nm) was also placed in the center of the pocket in contact with the nanoparticle suspension. The laser fiber was used to irradiate the hollow Au nanoparticles. The temperature change in the phantom was recorded by thermometer as a function of distance and time. FIG. 27 illustrates the experimental setup.

Figure 28A:
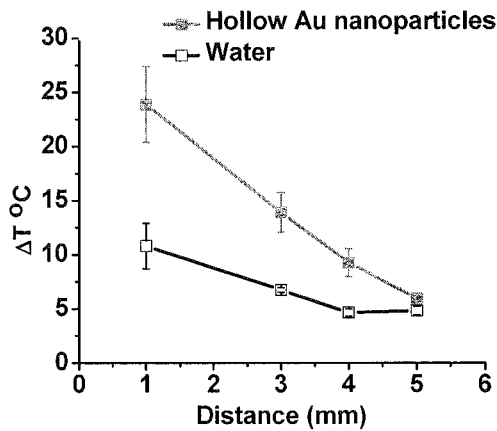
FIG. 28A is a comparison of some photothermal properties of hollow Au nanoparticles according to some embodiments described herein, and water at different measurement distances.
Figure 28B:
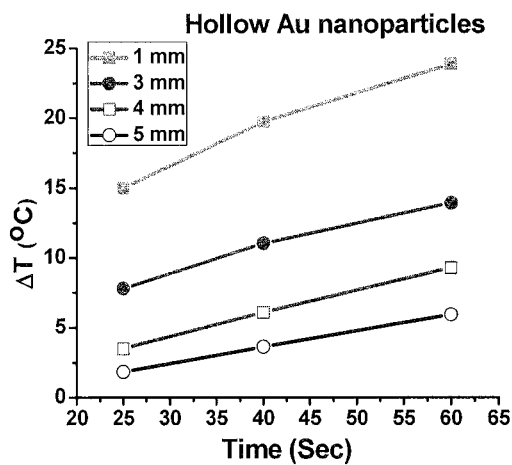
FIG. 28B is a comparison of some photothermal properties of hollow Au nanoparticles according to some embodiments described herein, measured at different distances and times.
Figure 28C:
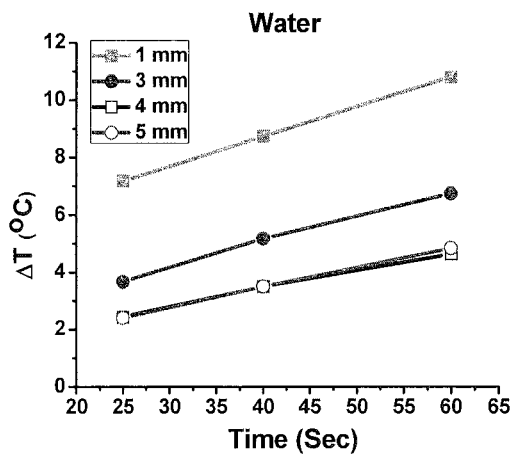
FIG. 28C is a comparison of some photothermal properties of water measured at different distances and times.

Irradiation from the NIR diode laser was carried out for 1 minute at a power density of 300 W/cm². With 1 minute irradiation time, the temperature rose by 23, 13, and 8 degrees Celsius at a distance of 1, 3, and 4 mm from the irradiation point, respectively. Because water also absorbs at 810 nm, control experiments were conducted using water rather than a suspension of hollow Au nanoparticles. The temperature increase in the control experiments was 12, 7, and 5 degrees Celsius at a distance of 1, 3, and 4 mm, respectively. The results are shown in FIG. 28.

Figure 29:
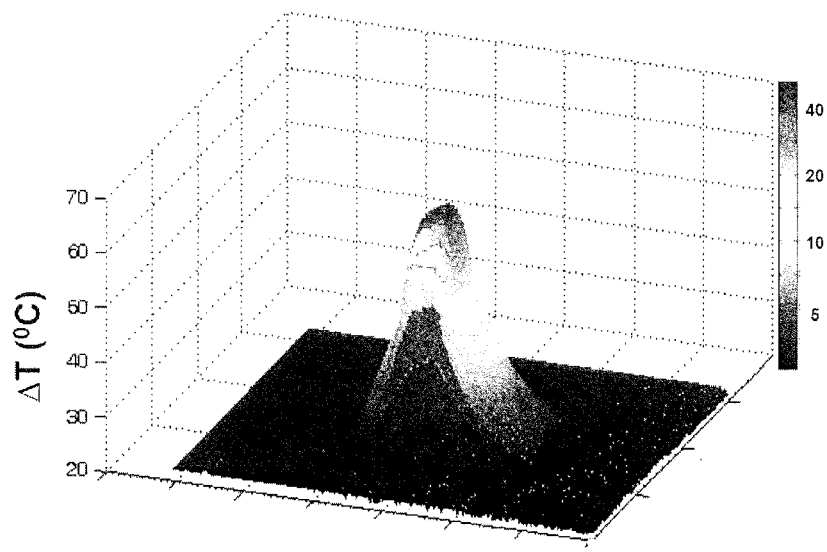
FIG. 29 is an infrared absorbance image of a cuvette containing hollow Au nanoparticles according to some embodiments described herein.
Figure 30:
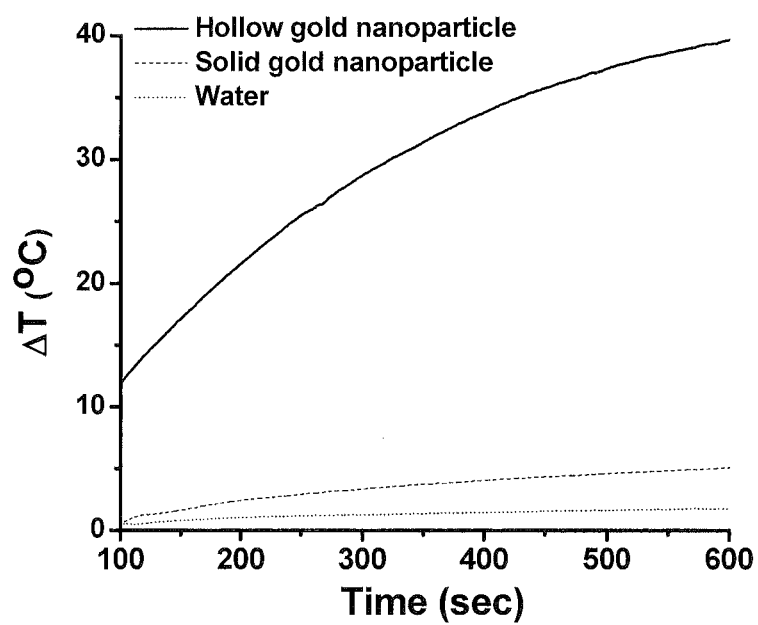
FIG. 30 is a comparison of temperature increases associated with solid Au nanoparticles, hollow Au nanoparticles according to some embodiments described herein, and water.
Figure 31:
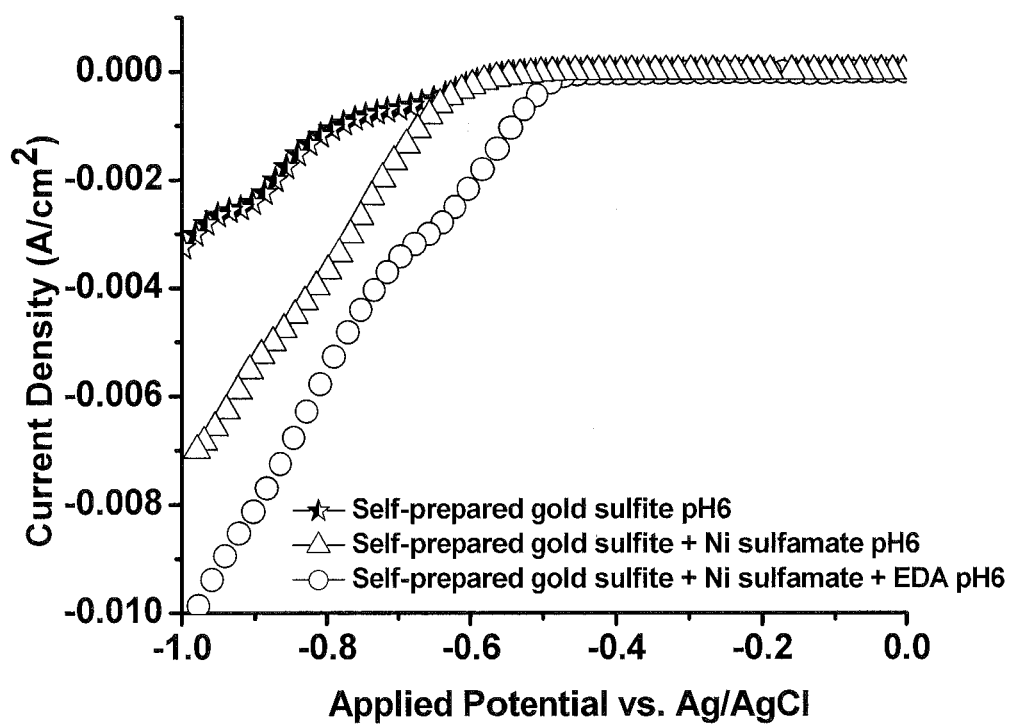
FIG. 31 is a series of cyclic voltammetry measurements. Data was recorded from the open circuit potential to −1.0 V (vs. Ag/AgCl) at a scan rate of 5 mV/s. The measurements were of different electrolytes including 10% sodium gold sulfite ($Na_3Au(SO_3)_2$) (aq.) and exhibiting a pH of about 6. The electrolyte associated with the data marked with triangles further included nickel sulfamate ($Ni(SO_3NH_2)_2$). The electrolyte associated with the data marked with circles further included $Ni(SO_3NH_2)_2$ and ethylenediamine (EDA).
Figure 32:
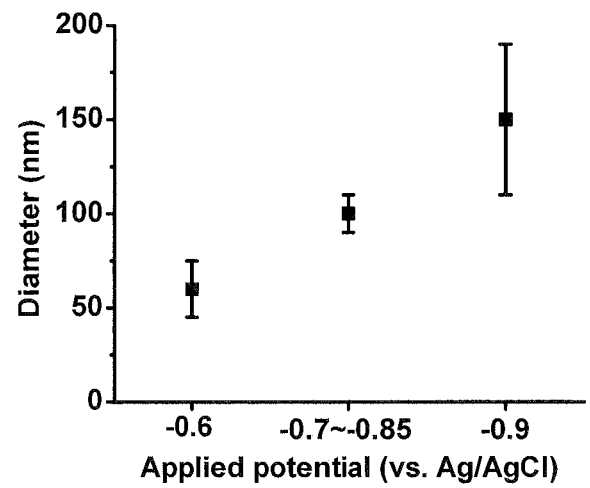
FIG. 32 is a plot of hollow Au nanoparticle size according to some embodiments described herein, against applied potential.
Figure 33:
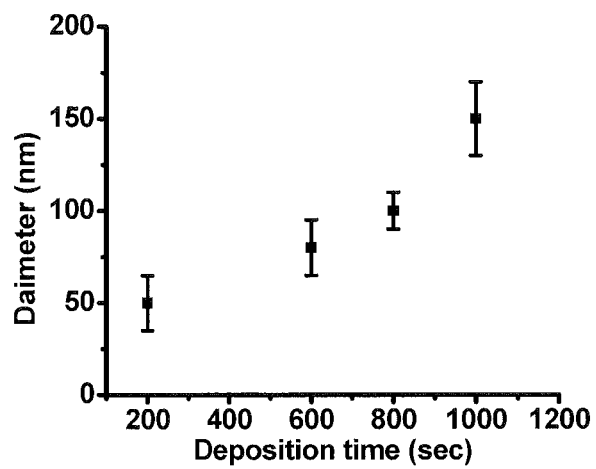
FIG. 33 is a plot of hollow Au nanoparticle size according to some embodiments described herein, against reaction time.
Figure 34:
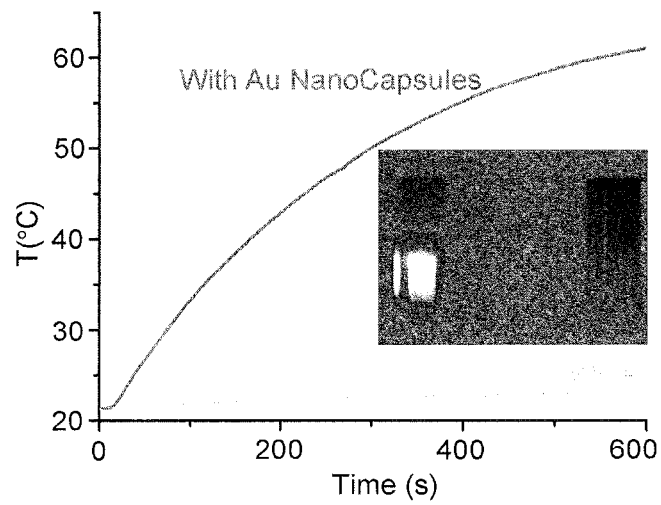
FIG. 34 is a comparison of the measured temperature of a cuvette of water and a cuvette containing an aqueous suspension of hollow Au nanoparticles ($1.9 \times 10^9$ particles per mL) according to some embodiments described herein, as a function of irradiation time, where irradiation was carried out using a near infrared (NIR) laser (800 nm) directed at the center of the cuvette with an incident laser power of 350 mW and a 3 mm diameter collimated Gaussian beam. The incident light flux was 1.2 W/cm$^2$. The temperature increase of the cuvette containing hollow Au nanoparticles according to some embodiments described herein, was 38 degrees after 10 minutes irradiation.
Figures 35A, 35B:
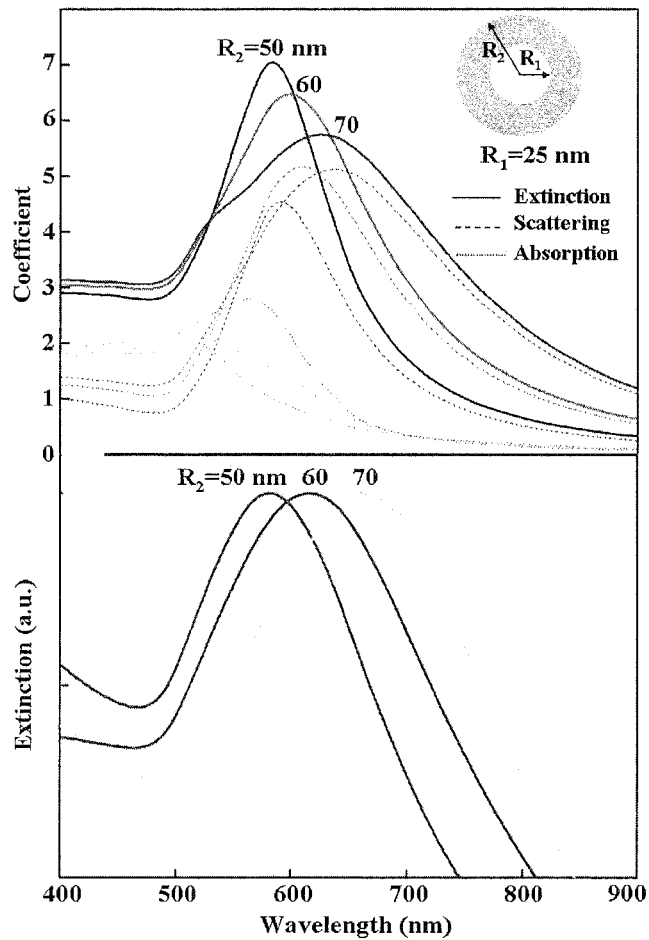
FIG. 35A shows the calculated total extinction, scattering and absorption efficiency for concentric hollow nanospheres using Mie theory.
FIG. 35B shows measured absorption spectra of hollow Au nanoparticles according to some embodiments described herein, having different sizes.

The photothermal properties of hollow Au nanoparticles were also investigated using an infrared focal plane array camera (FLIR model SC6000, 640×513 pixels, 25 µm pitch) with a detection window of 8-9.6 µm. The method compared the photothermal properties of two cuvettes containing two different nanoparticle suspensions: (1) solid spherical gold nanoparticles with a diameter of about 80 nm ($1.0 \times 10^{10}$ particles/mL) and (2) hollow gold nanoparticles with a cavity diameter of about 50 nm and an outer diameter of about 100 nm ($1.0 \times 10^{10}$ particles/mL). Each cuvette was placed at the focal plane of the camera lens, and collimated laser light (centered at 800 nm) was directed onto the center of the cuvette. The incident laser power was 350 mW, and the diameter of the collimated Gaussian beam was 3 mm. The incident light flux at the gold suspension was 1.2 W/cm². The image acquisition rate was 1 frame per second, beginning with the commencement of irradiation. The cuvettes were irradiated for 10 minutes each. Images were recorded for 30 minutes. To correlate temperature to measured infrared intensity for each image pixel, a calibration experiment was conducted. The calibration was carried out by recording images of a cuvette through which water was circulated from a heated water bath. A thermocouple placed in the water bath measured the temperature continuously in synchronization with the image acquisition. FIG. 29 shows the infrared absorbance image of the cuvette filled with hollow gold nanoparticles. The maximum temperature increase occurred at the center of the cuvette. Compared to the solid spherical gold nanoparticles, the temperature increase for the hollow gold nanoparticles was significantly enhanced, as shown in FIG. 30.

EXAMPLE 14

Radioactive Nanoparticles

Radioactive nanoparticles according to some embodiments described herein were prepared as follows.

First, to provide metal nanoparticle cores, hollow Au nanoparticles were prepared as generally described in Example 1. More particularly, anodic aluminum oxide (AAO) membranes having a diameter of 1 cm and 300 nm diameter through channels were used to collect the hollow Au nanoparticles. The resulting hollow Au nanoparticles were monodisperse and had an outer diameter greater than 100 nm. The hollow Au nanoparticles also had a 50-70 nm diameter cavity and a polycrystalline Au shell having a thickness of less than 25 nm.

Next, an inner metal shell and an outer metal shell were sequentially formed on the metal nanoparticle cores, as illustrated schematically in FIG. 36. For illustration purposes, the nanoparticles in FIG. 36 are depicted with cut away views. However, it is to be understood that such a depiction is for illustration purposes only and does not indicate the presence of an incomplete inner metal shell or outer metal shell. As shown in FIG. 36, the hollow Au nanoparticles were first coated with Cu by an electroless deposition process. Specifically, each alumina membrane containing trapped hollow Au nanoparticles was treated with 9 mL of $Cu^{2+}$ plating solution (containing 0.4 M $CuSO_4$ in 5% w/v EDTA, 37% v/v formaldehyde, and 1.0 M NaOH in a 1:1:1 v/v proportion) for 20 min. After 20 minutes, the membrane containing Cu-plated hollow Au nanoparticles was washed with water three times.

Next, the Cu layer was replaced by Pd through a galvanic replacement reaction. More particularly, two sequential galvanic replacement reactions were carried out. In the first galvanic replacement reaction, a solution containing the metallic radioisotope Pd-103 was added to the composition after the electroless plating of copper on the metal nanoparticle cores. In the second galvanic replacement reaction, non-radioactive Pd was added to the composition. Specifically, each AAO membrane was first drained and rinsed using a vacuum filtration setup with 0.1 M citric acid solution (three times) to completely soak the membrane channels with citric acid, and then 3 mL of 0.1 M citric acid solution containing 4.37 mCi Pd-103 was added. Plating of the "hot" Pd-103 was then continued for 24 h, followed by the addition of "cold" Pd plating solution (containing 0.0025 M $PdCl_2$ in 0.4 M citric acid solution). After 1 h, 2 M NaOH was added to dissolve the membrane and the resultant nanoparticle suspension was washed thrice with water by centrifugation (Legend Micro 21, FL, USA) at 14000 rpm for 10 min with sonication (Branson 2510, CT, USA) after each centrifugation run. In this manner, radioactive nanoparticles having a hollow Au nanoparticle core and an outer metal shell comprising Pd-103 and non-radioactive Pd were prepared. These radioactive nanoparticles can be denoted as "$^{103}$Pd@Au nanoseeds." The pellet of $^{103}$Pd@Au nanoseeds was dispersed by sonication in PBS (pH=7.4). The overall process yielded $^{103}$Pd@Au nanoseeds with greater than 80% radiolabeling efficiency as determined by dose calibrator (Capintech Inc, PA, USA), where the percent efficiency is based on the total amount of Pd-103 used. Dynamic light scattering (DLS) assessment confirmed the synthesized $^{103}$Pd@Au nanoseeds to be monodisperse with mean particle size of 140.5±7.6 nm. Additionally, the $^{103}$Pd@Au nanoseeds were highly negatively charged (−25.81±1.8 mV). Further, as illustrated in FIG. 37, TEM microscopy demonstrated the core-shell structure of the nanoparticles. As illustrated in FIG. 38, SEM microscopy indicated a nearly perfect spherical shape and very narrow size distribution for the population of nanoparticles. It should be noted that, for safety and compliance reasons, the microscope images illustrated in FIG. 37 and FIG. 38 are of non-radioactive nanoparticles that are counterparts to the radioactive nanoparticles described in this Example. Specifically, the non-radioactive nanoparticles of FIG. 37 and FIG. 38 were made in the same manner and had the same structure as described herein for radioactive nanoparticles, except without the use of a radioisotope. The $^{103}$Pd@Au nanoseeds were found to be extremely stable and retained their original size even after being stored in solution for 2 months at 8±2° C. Although caking of $^{103}$Pd@Au nanoseeds was observed during the storage, the nanoseeds could be redispersed in PBS by mild sonication for 30 seconds.

For the above procedure, $PdCl_2$ and $CuSO_4.5H_2O$ were obtained from Sigma-Aldrich (St. Louis, Mo.) and Alfa Aesar (Ward Hill, Mass.), respectively. Radioactive Pd-103 was purchased from Nordion (Ontario, Canada). PBS was purchased from Invitrogen Corporation (Carlsbad, Calif.). All other solvents and reagents were of analytical purity grade and were purchased from VWR (Brisbane, Calif.). All aqueous solutions were prepared in Millipore Milli-Q water (18 MΩ-cm) that was obtained from a Millipore Gradient Milli-Q water system (Billerica, Mass.).

EXAMPLE 15

Methods of Performing Brachytherapy

Figure 39:
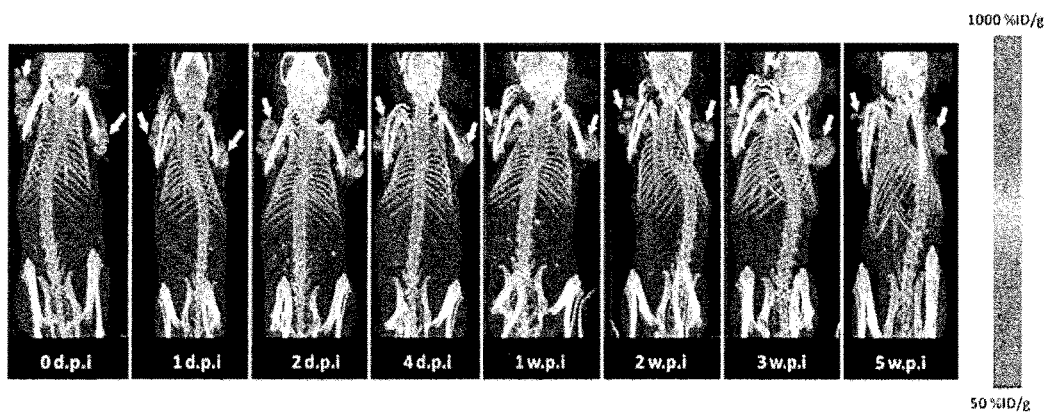
FIG. 39 illustrates serial SPECT/CT imaging of tumor-bearing mice treated with radioactive nanoparticles according to some embodiments described herein. The white arrows in FIG. 39 indicate the locations of tumors.
Figure 40:
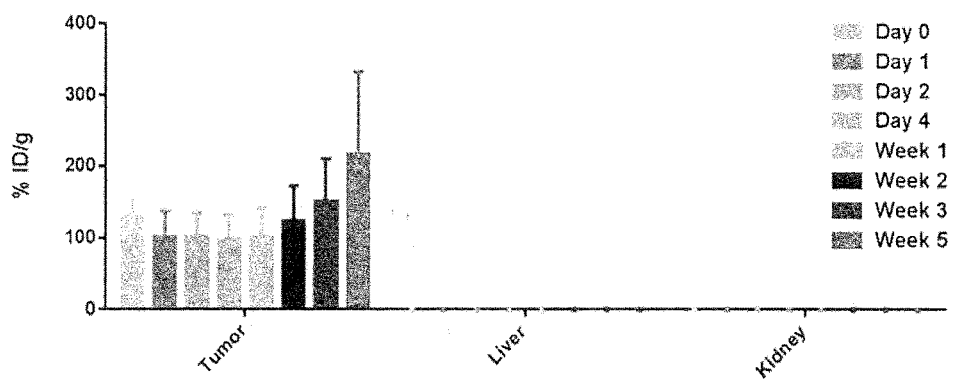
FIG. 40 illustrates the results of quantitative SPECT analysis of radioactivity (quantified as percentage injected dose per gram, % ID/g) from the tumor, liver, and spleen of mice treated with radioactive nanoparticles according to some embodiments described herein.

The use of the radioactive nanoparticles of Example 14 for brachytherapy was evaluated in animal models as follows.
A. Animal Studies For in vivo evaluation of the radioactive nanoparticles or "nanoseeds" of Example 14, including their retention in tumor sites, toxicity, and therapeutic efficacy, SCID mice bearing human prostate cancer tumors were used. Tumor induction was carried out, with slight modifications, according to Matsuno et al., "Induction of lasting complete regression of preformed distinct solid tumors by targeting the tumor vasculature using two new anti-endoglin monoclonal antibodies," *Clinical Cancer Research*, 5, 371-382 (1999); and VanWeelden et al., "Apoptotic regression of MCF-7 xenografts in nude mice treated with the vitamin D3 analog, EB1089," *Endocrinology*, 139, 2102-2110 (1998). Further details are provided below. A cell suspension containing $3 \times 10^6$ PC3 cells was implanted subcutaneously into both shoulders of SCID mice. The tumor was allowed to grow for 4 weeks to reach a palpable size of about 181.67±62.14 $mm^3$. Animals were randomized at day 0 into three groups (n=6), in which (a) PBS solution, (b) "cold" Pd@Au nanoparticle PBS suspension (where such "cold" nanoparticles were the same as the nanoseeds of Example 14, except excluding radioactive Pd-103), or (c) "hot" nanoseed PBS suspension was injected into tumors carried by the SCID mice. Groups (a) and (b) served as controls. Injection was performed at 6-9 randomly selected locations to uniformly distribute the dose in the whole tumorous mass. For the experimental sample (i.e., the hot nanoseed sample), 1.5 mCi of the hot nanoseeds containing Pd-103 was injected into the tumor. The suspension volume was 40 µL, with a nanoparticle concentration of $2.03 \times 10^{10}$ nanoparticles/mL. The same amount of the PBS solution and cold nanoseed compositions were injected into tumors in the two control groups.
B. Retention of Radioactive Nanoparticles in Tumor Sites For the group treated with the hot nanoseeds of Example 14, after the intratumoral injection, SPECT/CT imaging was conducted in a longitudinal manner (at 0, 1, 2, 4 days post injection (d.p.i) and 1, 2, 4, and 5 weeks post injection (w.p.i.)) to noninvasively monitor the retention of the nanoseeds by acquisition of the low energy X-ray emissions of Pd-103 on a small animal SPECT/CT scanner. The results are illustrated in FIG. 39 and FIG. 40. The quantitative SPECT analysis performed at 1 d.p.i. (FIG. 40) showed that the injected dose stayed at the site of administration (101.50±23.72% ID/g) with negligible amounts of radioactivity observed in the liver (0.11±0.06% ID/g) and spleen (0.14±0.01% ID/g). As the study progressed, the uptake level in the tumor determined by quantitative SPECT analysis increased gradually to 274.48±77.62% ID/g at 5 w.p.i, as the tumor volume shrunk due to the radiotherapeutic effect of the nanoseeds.

The biodistribution of the nanoseeds were further investigated by a parallel ex vivo assay. At different time points during the study (1 day, 1 week, 2 weeks, 3 weeks, and 5 weeks after injection), three mice treated with hot nanoseeds were sacrificed, and the organs of interest (blood, heart, lung, muscle, bone, fat, liver, spleen, kidney, stomach, small intestine, large intestine, brain, tail, and tumor) were excised, weighed, and then measured for radioactivity by a γ-counter. Thereafter, the tissues were dissolved using aqua regia and analyzed using ICP-MS to measure the Au and Pd content. There was good consistency between the γ-counter and ICP-MS results (no statistically significant difference, p=0.88), indicating that the radioactive Pd-103 stayed with the nanoseeds during the five weeks of the therapeutic study. The ex vivo biodistribution study demonstrated that 95.19±0.94% of the nanoseeds remained inside the tumor, while 3.31±1.11% and 0.39±0.24% went to the liver and spleen, respectively. No meaningful uptake was observed in other tissues. Further, the tumor uptake remained essentially the same (p 0.35) over the five weeks of the study.
C. Toxicity of Radioactive Nanoparticles Toxicity of the radioactive nanoparticles of Example 14 was assessed and compared with a control group and with the "cold" nanoseeds described above. Over the course of the 5-week treatment period, complete blood count (CBC), alanine transaminase (ALT), aspartate transaminase (AST), blood urea nitrogen (BUN), and creatinine levels were monitored at 10 and 30 d.p.i. Red blood cell (RBC) count and the mean hemoglobin volume per RBC (MCH) remained unaffected throughout the study, suggesting that the therapy elicited no hemolytic effect. It is further noted that the radioactive nanoparticles initially reduced the white blood cell (WBC) count at 10 d.p.i., which is common to radiotherapy. However, the effect was found to be reversible, as seen by the recovery of the WBC count to normal after 30 d.p.i. A similar effect was observed in the case of platelet counts and other parameters. The BUN, ALT, AST and creatinine tests showed no notable changes among the three groups of mice, indicating no kidney and liver related toxicity associated with the radioactive nanoparticles.

D. Therapeutic Efficacy of Radioactive Nanoparticles

Figure 41:
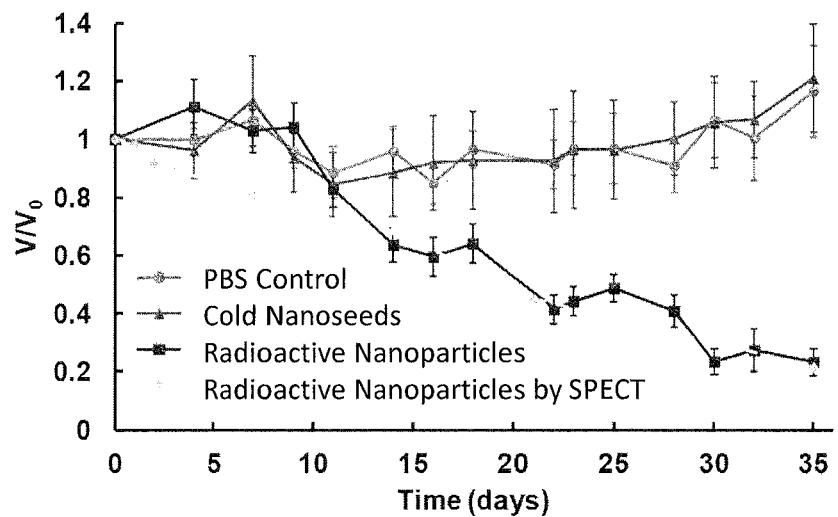
FIG. 41 illustrates tumor volume for mice treated with control compositions and radioactive nanoparticles according to some embodiments described herein.
Figure 42:
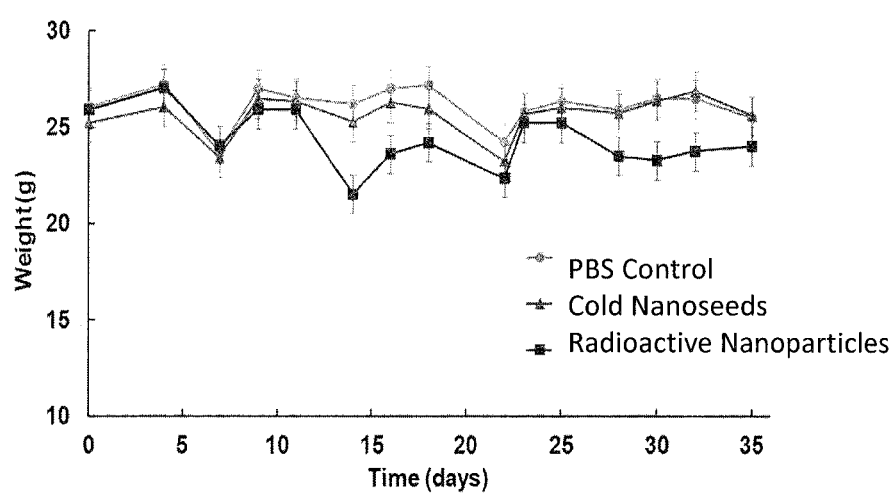
FIG. 42 illustrates body weight for mice treated with control compositions and radioactive nanoparticles according to some embodiments described herein.

The tumor volumes (FIG. 41) of three groups of tumor-bearing mice were measured using a caliper every other day in a double-blinded manner. After 15 d.p.i, a clear separation of tumor growth trend was seen (p<0.0001). A prominent reduction in tumor volume was noted in subjects treated with the radioactive nanoparticles, while a progressive increment in tumor volume was observed in both PBS and cold nanoseed groups. It is noteworthy that the volume of two tumors in two of the mice in the radioactive nanoparticle test group shrank so much that they could not be found after 35 d.p.i. The average tumor size in the PBS and cold nanoseed groups increased from 67.08±30.96 mm$^3$ and 58.75±35.29 mm$^3$ to 187±80.11 mm$^3$ and 122.14±4.082 mm$^3$, respectively. On the other hand, in the radioactive nanoparticle group, a significant tumor size reduction was observed: 82.75±46.25 mm$^3$ to 19.83±20.12 mm$^3$ (p<0.001) after 35 days of treatment.

Figure 43:
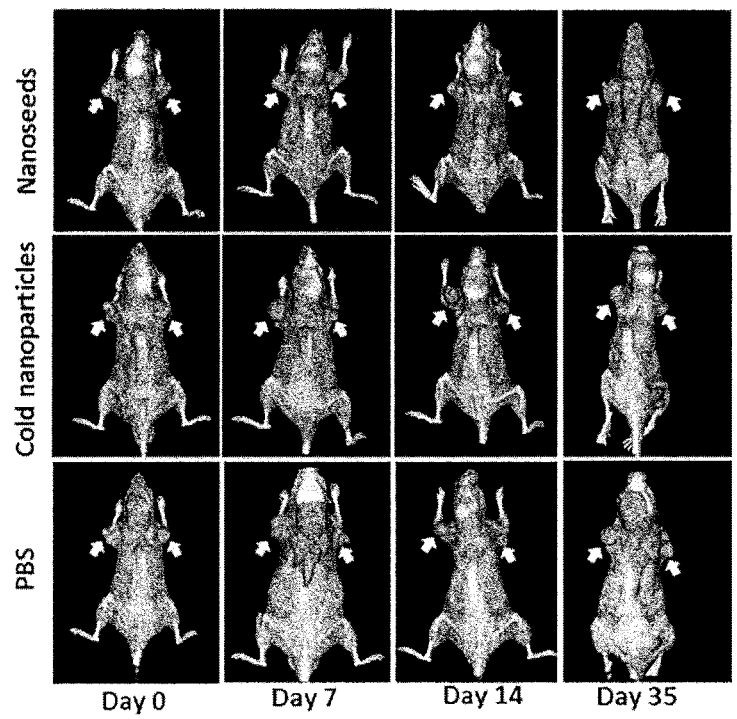
FIG. 43 illustrates serial FDG-PET/CT images for mice treated with control compositions and radioactive nanoparticles according to some embodiments described herein. The white arrows in FIG. 43 indicate tumor sites.
Figure 44:
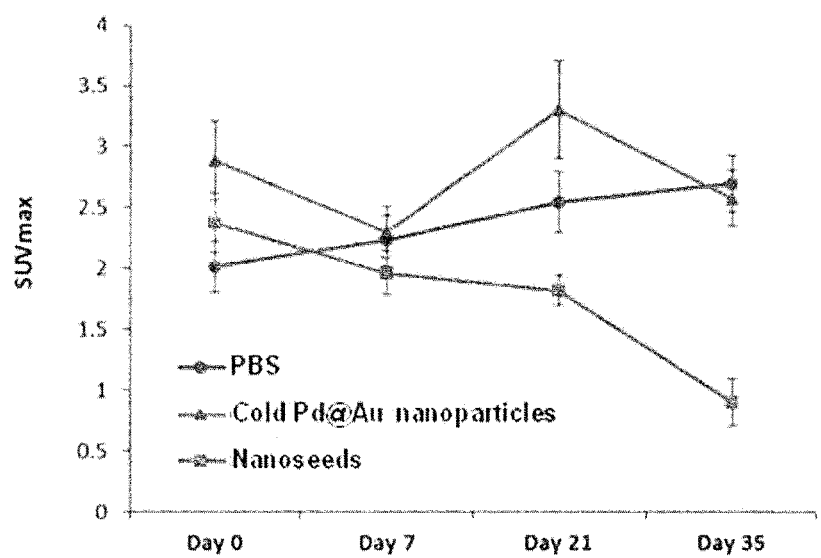
FIG. 44 illustrates the results of quantitative PET analysis for mice treated with control compositions and radioactive nanoparticles according to some embodiments described herein.
Figure 45:
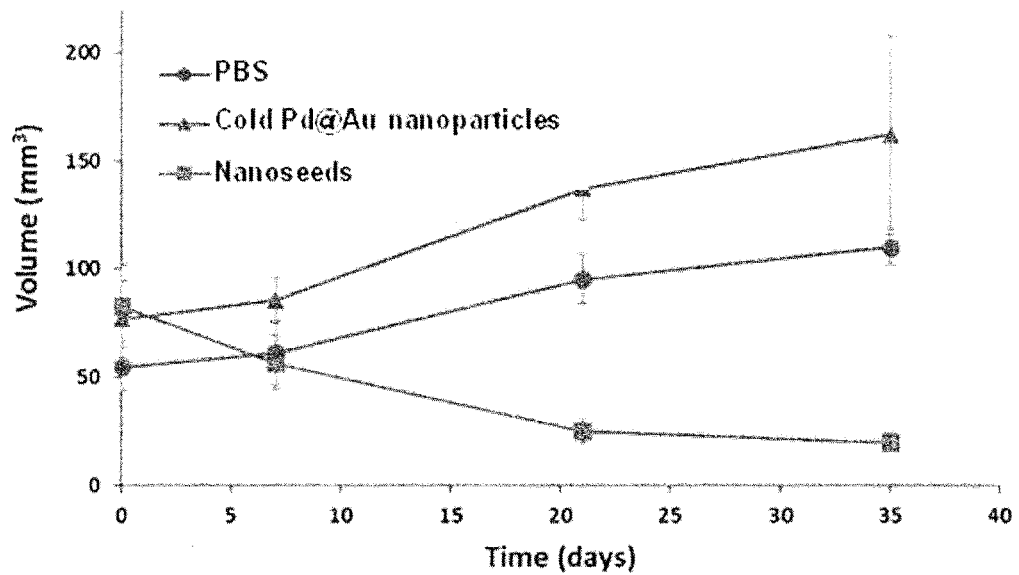
FIG. 45 illustrates tumor volume changes determined by CT scan analysis (mean±SEM) for mice treated with control compositions and radioactive nanoparticles according to some embodiments described herein.

[F18]FDG (2-[$^{18}$F]Fluoro-2-deoxyglucose) positron emission tomography (PET) imaging was also employed for assessing therapeutic efficacy of the radioactive nanoparticles of Example 14. FIG. 43 shows typical FDG-PET/CT scan images for the three studied groups of mice at different time points. It can be seen that at Day 0, the mice from all the three groups had roughly the same tumor sizes with similar FDG uptakes, while as the study progressed for 35 days, a significant tumor FDG uptake reduction was observed in the radioactive nanoparticle treated group (upper panel) as compared to that in the PBS (lower panel) and cold nanoseed (middle panel) treated groups. The quantitative PET analysis is illustrated in FIG. 44 as the maximum standardized uptake value ($SUV_{max}$) versus time. The SUV represents the concentration of radioactivity in the tumor, normalized to the injected FDG dose and the body weight. It shows that $SUV_{max}$ for the mice treated with the radioactive nanoparticles decreased 62% from Day 0 to Day 35 (p=0.00041), and at Day 35 was 65% (p=0.00019) and 66.5% (p=0.00028) less than that in the PBS and cold nanoseed treated groups, respectively. The decrease in the $SUV_{max}$ of the radioactive nanoparticle-treated group to such a low level is evidence of the pathological responses of the tumors to the radiation therapy by the radioactive nanoparticles. CT images were also utilized to determine the tumor volume, as shown in FIG. 45.

E. Methods

SPECT Imaging Method Using the Low Energy Emission of Pd-103

A SPECT imaging method with Pd-103 was developed in a NanoSPECT/CT Plus System (Bioscan, Washington, D.C., USA). The Pd-103 isotope was added to the NanoSPECT/CT Plus isotope library by setting the energy peak and width to 18 keV and 60%, respectively. Quantification calibration was performed subsequently using a 3 mL syringe and 1.2 mCi of Pd-103.

Intratumoral Administration of Radioactive Nanoparticles and SPECT Analysis

A radioactive nanoparticle dose (≈1.5 mCi) was prepared in PBS (pH 7.4) and injected intratumorally in PC3-tumor bearing SCID mice. Intratumoral injection was carefully performed at 6-9 randomly selected locations. After injection, small animal imaging was performed using Nano-SPECT/CT Plus System. After the intratumor injection of each dose, SPECT and CT images were acquired at 0, 1, 2, 4, 7, 14, 21 and 35 d.p.i. The field of view (FOV) of the SPECT/CT was centered at the shoulders of the mouse. The CT imaging was performed using 360 projections per rotation with 55 kVp, 1000 ms exposure, and the binning factor of 1:1. The SPECT data were collected with 4 detector arrays collimated with multi-pinhole apertures giving a post-reconstruction resolution of 0.73 mm. The SPECT image reconstruction was carried out using HiSPECT NG (Scivis wissenschaftliche Bildverarbeitung GmbH, Germany) with 35% smoothing, 100% resolution, and 3×3 iterations (Standard mode). The quantification of the tumor activity was performed using the InVivoScope 2.0 software package (Bioscan, Washington, D.C., USA). After co-registration of the CT and SPECT images, a cylindrical region of interest (ROI) was drawn, encompassing the tumor and liver in all planes containing the organs.

FDG-PET/CT Imaging

Mouse PET/CT imaging was performed using Siemens Inveon PET/CT multimodality system (Siemens Medical Solutions, Knoxville, Tenn.) with effective spatial resolution of 1.4 mm at the center of field of view (FOV). All animals were fasted for 12 hours prior to PET imaging. Each mouse received 150 µCi of FDG in 150 µL in saline intravenously via tail vein injection. The mice were placed on a heat pad before and during image acquisition. PET images were acquired one hour post-injection (P.I.), for 15 minutes, with animals under 2.5% Isoflurane. PET images were reconstructed into a single frame using the 3D Ordered Subsets Expectation Maximization (OSEM3D/MAP) algorithm. CT images were acquired immediately after PET with the FOV centered at the shoulder of the mouse. CT projections (360 steps/rotation) were acquired with a power of 80 kVp, current of 500 µA, exposure time of 145 ms, binning of 4, and effective pixel size of 102 µm. The CT reconstruction protocol used a downsample factor of 2, was set to interpolate bilinearly, and used a Shepp-Logan filter. PET and CT images were co-registered in Inveon Acquisition Workplace (Siemens Medical Solutions, Knoxville, Tenn.) for analysis. Regions of interest (ROI) were drawn manually, encompassing the tumor in all planes containing the tissue. The target activity was calculated as percentage injected dose per gram.

Ex Vivo Measurements of Radioactivities and Au and Pd Contents Among Various Organs At 1 day, 1 week, 2 weeks, 3 weeks, and 5 weeks after the injection of radioactive nanoparticles, three mice were sacrificed, and the desired organs including blood, heart, lung, muscle, bone, fat, liver, spleen, kidney, stomach, small intestine, large intestine, brain, tail, and tumor were collected, weighed and transferred to 20 mL vials. To measure the radioactivity associated with each organ, the activity of each vial was measured in a γ-counter (Perkin Elmer 2480 Wizard) and recorded as counts per minute. Then, aqua regia was added to the vials and left overnight to digest the organs. After 24 h, the aqua regia is boiled off at 150° C. After boiling, 10 mL of 1% HCl solution was added to the vials, which were then sonicated for 30 minutes. The Au and Pd concentration were then measured in an inductively coupled plasma mass spectrometer (ICP-MS, Agilent 7700x). The measurement was repeated at least three times for each sample.

Statistical Analysis

Quantitative data were expressed as mean±standard errors of mean (SEM). Comparison among the means and the significance evaluation were performed by one-way ANOVA, where P values of <0.05 were considered statistically significant. The data from different groups and within each individual group at different time points were compared to determine whether they were statistically distinguishable. All data analysis was carried out using SPSS Ver. 16.0 software (IBM SPSS Statistics).

EXAMPLE 16

Radioactive Nanoparticles and Method of Performing Brachytherapy

Radioactive nanoparticles according to one embodiment described herein are prepared and used to perform brachytherapy as follows.

First, $^{103}$Pd@Au nanoseeds are prepared as described above in Example 14. Next, a thiolated 1,4,7,10-tetraazacyclododecane-1,4,7,10-tetraacetic acid (DOTA) is conjugated to the surface of the nanoseeds. Finally, the conjugated DOTA ligands are radiolabeled with Y-90, resulting in radioactive nanoparticles having a composite radiation profile including two differing radiation profiles from two differing radioisotopes: (1) a more rapid decay profile provided by Y-90 and (2) a slower decay profile provided by Pd-103. These dual-emitting radioactive nanoparticles are then administered intraarterially to the liver. Specifically, the radioactive nanoparticles are injected into the hepatic artery to treat primary liver cancer or hepatocellular cancer (HCC) with both a low dose rate (LDR) and a high dose rate (HDR).

All patent documents referred to herein are incorporated by reference in their entireties. Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A radioactive nanoparticle comprising:
   a metal nanoparticle core;
   an outer metal shell disposed over the metal nanoparticle core;
   a metallic radioisotope disposed within the metal nanoparticle core or within the outer metal shell; and
   an inner metal shell disposed between the metal nanoparticle core and the outer metal shell,
   wherein the radioactive nanoparticle has a size of about 30-500 nm in three dimensions,
   wherein the metal nanoparticle core is formed from Au, the inner metal shell is formed from Cu, and the outer metal shell is formed from Pd, Rh, or Au, and
   wherein radiation emitted by the metallic radioisotope passes through the inner metal shell and/or the outer metal shell into a surrounding environment of the nanoparticle without heating the inner metal shell and/or the outer metal shell.

2. The radioactive nanoparticle of claim 1, wherein the radioactive nanoparticle has a size of about 80-200 nm in three dimensions.

3. The radioactive nanoparticle of claim 1, wherein the metal nanoparticle core and the outer metal shell are formed from the same metal or combination of metals.

4. The radioactive nanoparticle of claim 1, wherein the metallic radioisotope is disposed within the outer metal shell.

5. The radioactive nanoparticle of claim 4, wherein the metallic radioisotope comprises a metal that is the same as a metal of the outer metal shell.

6. The radioactive nanoparticle of claim 4, wherein the metallic radioisotope and the outer metal shell are formed from differing metallic elements.

7. The radioactive nanoparticle of claim 1 further comprising a second metallic radioisotope disposed within the metal nanoparticle core or within the outer metal shell.

8. The radioactive nanoparticle of claim 1, wherein the metallic radioisotope is disposed within the metal nanoparticle core.

9. The radioactive nanoparticle of claim 1, wherein the metallic radioisotope comprises Cu-64, Cu-67, Y-90, Pd-103, Rh-105, Re-186, Re-188, Ir-192, or Au-198.

10. The radioactive nanoparticle of claim 1, wherein the radioactive nanoparticle has a negative surface charge.

11. A method of performing brachytherapy, the method comprising:
    disposing a composition within a biological compartment, wherein the composition comprises a plurality of radioactive nanoparticles, at least one of the plurality of radioactive nanoparticles comprising:
    a metal nanoparticle core;
    an outer metal shell disposed over the metal nanoparticle core;
    a metallic radioisotope disposed within the metal nanoparticle core or within the outer metal shell; and
    an inner metal shell disposed between the metal nanoparticle core and the outer metal shell,
    wherein the radioactive nanoparticle has a size of about 30-500 nm in three dimensions,
    wherein the metal nanoparticle core is formed from Au, the inner metal shell is formed from Cu, and the outer metal shell is formed from Pd, Rh, or Au, and
    wherein radiation emitted by the metallic radioisotope passes through the inner metal shell and/or the outer metal shell into a surrounding environment of the nanoparticle without heating the inner metal shell and/or the outer metal shell.

12. The method of claim 11, wherein the metallic radioisotope is a β-emitter.

13. The method of claim 11, wherein the biological compartment is a tumor.

14. The method of claim 13, wherein at least about 80% of the radioactive nanoparticles are retained within the tumor for at least 3 weeks.

15. The method of claim 11 further comprising:
    irradiating the biological compartment with an external beam of ionizing radiation.

16. The radioactive nanoparticle of claim 1, wherein the metallic radioisotope is a β-emitter.

17. The radioactive nanoparticle of claim 1, wherein the radioactive nanoparticle has a radioactivity of about 0.4 to 400 Bq.

* * * * *